US006723506B2

(12) United States Patent
Fletcher et al.

(10) Patent No.: US 6,723,506 B2
(45) Date of Patent: Apr. 20, 2004

(54) METHOD OF IDENTIFYING PAX8-PPAR GAMMA-NUCLEIC ACID MOLECULES

(75) Inventors: Jonathan A. Fletcher, Brookline, MA (US); Todd G. Kroll, Newton Highlands, MA (US)

(73) Assignee: Brigham and Women's Hospital, Boston, MA (US)

( * ) Notice: Subject to any disclaimer, the term of this patent is extended or adjusted under 35 U.S.C. 154(b) by 0 days.

(21) Appl. No.: 09/765,111

(22) Filed: Jan. 18, 2001

(65) Prior Publication Data

US 2002/0106796 A1 Aug. 8, 2002

Related U.S. Application Data

(60) Provisional application No. 60/177,109, filed on Jan. 20, 2000, and provisional application No. 60/225,079, filed on Aug. 14, 2000.

(51) Int. Cl.[7] .......................... C12Q 1/68; C12P 19/34; C07H 21/02; C07H 21/04
(52) U.S. Cl. ..................... 435/6; 435/91.2; 536/23.5; 536/24.31; 536/24.33
(58) Field of Search .................... 435/6, 91.1, 91.2; 536/23.1, 23.5, 24.31, 24.33

(56) References Cited

U.S. PATENT DOCUMENTS

| 4,444,779 A | 4/1984 | Kawamatsu et al. |
| 5,686,596 A | 11/1997 | Mukherjee |
| 5,696,104 A | 12/1997 | Demarchez et al. |
| 5,730,975 A | 3/1998 | Hotamisligil et al. |
| 5,747,250 A | 5/1998 | Gruss et al. |
| 5,814,647 A | 9/1998 | Urban et al. |
| 5,861,274 A | 1/1999 | Evans et al. |
| 5,902,726 A | 5/1999 | Kliewer et al. |
| 5,925,657 A | 7/1999 | Seed et al. |
| 5,968,960 A | 10/1999 | Schwartz |

FOREIGN PATENT DOCUMENTS

| WO | WO 95/10271 | 4/1995 |
| WO | WO 95/35108 | 12/1995 |
| WO | WO 96/33724 | 10/1996 |
| WO | WO 96/34943 | 11/1996 |
| WO | WO 97/17091 | 5/1997 |
| WO | WO 98/25598 | 6/1998 |

OTHER PUBLICATIONS

Sozzi, G. et al "A t(2;3)(q12–13;p24–25) in Follicular THyroid Adenomas" Cancer Genet. Cytogenet. 64:38–41 (1992).*
Poleev, Andrej et al, "Distinct functional properties of three human paired–box–protein, PAX8, isoforms generated by alternative splicing in thyroid, kidney and Wilms' tumors," Eur. J. Biochem., 1995, vol. 228, pp. 899–911.
Maulbecker, Catharina C. et al., "The oncogenic potential of Pax genes," The EMBO Journal, 1993, vol. 12, No. 6, pp. 2361–2367.

Motojima K., "Peroxisome proliferator–activated receptor (PPAR): structure, mechanisms of activation and diverse functions," Cell Struct Funct., Oct. 1993, 18(5):267–77—Abstract.
Bogazzi, F. et al., "A novel heterodimerization partner for thyroid hormone receptor. Peroxisome proliferator–activated receptor," J. Biol. Chem., Apr. 22, 1994, 269(16):11683–6—Abstract.
Tell, G. et al., "structural defects of a Pax8 mutant that give rise to congenital hypothyroidism," Biochem. J., Jul. 1, 1999, 341 (Pt 1):89–93—Abstract.
Macchia, P.E. et al., "PAX8 mutations associated with congenital hypothyroidism caused by thyroid dysgenesis," Nat. Genet., May 1998, 19(1):83–6—Abstract.
Damante, G., "Thyroid defects due to Pax8 gene mutations," Eur. J. Endocrinol., Dec. 1998, 139(6):563–6.
Poleev, A. et al., "Distinct functional properties of three human paired–box–protein, PAX8, isoforms generated by alternative splicing in thyroid, kidney and Wilms' tumors," Eur. J. Biochem., Mar. 15, 1995, 228(3):899–911—Abstract.
Poleev, A. et al., "PAX8, a human paired box gene: isolation and expression in developing thyroid, kidney and Wilms' tumors," Development, Nov. 1992, 116(3):611–23—Abstract.
Plachov, D. et al., "Pax8, a murine paired box gene expressed in he developing excretory system and thyroid gland," Development, Oct. 1990, 110(2):643–51—Abstract.
Kozmik, Z. et al., "Alternative splicing of Pax–8 gene transcripts is developmentally regulated and generates isoforms with different transactivation properties," Mol. Cell Biol., Oct. 1993, 13(10):6024–35—Abstract.
Peraldi, P. et al., "Thiazolidinediones block tumor necrosis factor–alpha–induced inhibition of insulin signaling," J. Clin. Invest., Oct. 1, 1997, 100(7):1863–9—Abstract.
Devchand, P.R. et al., "Chemical probes that differentially modulate peroxisome proliferator–activated receptor alpha and BLTR, nuclear and cell surface receptors for leukotriene B(4)," J. Biol. Chem., Aug. 13, 1999, 274(33):23341–8—Abstract.
Tontonoz, P. et al., "Terminal differentiation of human liposarcoma cells induced y ligands for peroxisome proliferator–activated receptor γ and the retinoid X receptor," Medical Sciences, Jan. 1997, vol. 94, pp. 237–241.

(List continued on next page.)

Primary Examiner—Carla J. Myers
Assistant Examiner—Sally A Sakelaris
(74) Attorney, Agent, or Firm—Wolf, Greenfield & Sacks, P.C.

(57) ABSTRACT

An oncogene designated PAX8-PPARγ1 contains a PAX8 coding region fused to PPARγ coding region. Molecular characterization of PAX8-PPARγ1 molecules provides nucleotide and amino acid sequences useful for detection and treatment of certain tumors, particularly thyroid follicular carcinomas.

8 Claims, 9 Drawing Sheets

OTHER PUBLICATIONS

Kubota, Tetsuya et al., "Ligand for Peroxisome Proliferator-activated Receptor γ(Troglitazone) Has Potent Antitumor Effect against Human Prostate Cancer Both in Vitro and In Vivo," *Cancer Research*, Aug. 1, 1998, vol. 58, pp. 3344–3352.

Editorial, "PPAR–the good news and the bad," *Nature Medicine*, Sep. 1998, vol. 4, No. 9, pp. 981.

Lefebvre, Anne–Marie et al., "Activation of the peroxisome proliferator–activated receptorγ promotes the development of colon tumors in C57BL/6J–APC$^{min}$/+mice," *Nature Medicine*, Sep. 1998, vol. 4, No. 9, pp. 1053–1057.

Saez, Enrique et al., "Activators of the nuclear receptor PPARγ enhance colon polyp formation," *Nature Medicine*, Sep. 1998, vol. 4, No. 9, pp. 1058–1061.

Mueller, Elisabetta et al., "Terminal Differentiation of Human Breast Cancer through PPARγ," *Molecular Cell*, Feb. 1998, vol. 1, pp. 465–470.

Sarraf, Pasha et al., "Loss–of–Function Mutations in PPARγ Associated with Human Colon Cancer," Molecular Cell, Jun. 1999, vol. 3(6), pp. 799–804.

Sarraf, Pasha et al., Differentiation and reversal of malignant changes in colon cancer through PPARγ, Sep. 1998, vol. 4, No. 9, pp. 1046–1052.

Elstner, Elena et al., "Ligands for peroxisome proliferator–activated receptor γ and retinoic acid receptor inhibit growth and induce apoptosis of human breast cancer cells in vitro and in BNX mice," *Proc. Natl. Acad. Sci. USA*, Jul. 1998, vol. 95, pp. 8806–8811.

Tong–Chuan, He et al., "PPARδ Is an APC–Regulated Target of Nonsteroidal Anti–Inflammatory Drugs," *Cell*, Oct. 29, 1999, vol. 99, pp. 335–345.

Seed, Brian, "PPARγ and colorectal carcinoma: conflicts in a nuclear family," *Nature Medicine*, Sep. 1998, vol. 4, No. 9, pp. 1004–1005.

Kitamura, S. et al., "PPARgamma Inhibits the Expression of c–MET in Human Gastric Cancer Cells through the Suppression of Ets," *Biochem. Biophys. Res. Commun.*, Nov. 19, 1999, 265(2):453–456—Abstract.

Hirase, N. et al., "Thiazolidinedione Induces Apoptosis and Monocytic Differentiation in the Promyelocytic Leukemia Cell Line HL60," *Oncology*, Oct. 1999, 57 Suppl. S2:17–26—Abstract.

Takahashi, N. et al., "Activation of PPARgamma inhibits cell growth and induces apoptosis in human gastric cancer cells," *FEBS Lett*, Jul. 16, 1999, 455(1–2):135–9—Abstract.

Yee, L.D. et al., "Peroxisome proliferator–activated receptor gamma activation in human breast cancer," *Int. J. Oncol.*, Nov. 1999, 15(5):967–73—Abstract.

Asou, H. et al., "Growth inhibition of myeloid leukemia cells by troglitazone, a ligand for peroxisome proliferator activated receptor gamma, and retinoids," *Int. J. Oncol.*, Nov. 1999, 15(5):1027–31—Abstract.

Kubota, T. et al., "Ligand for peroxisome proliferator–activated receptor gamma (troglitazone) has potent antitumor effect against human prostate cancer both in vitro and in vivo," *Cancer Res.*, Aug. 1, 1998, 58(15):3344–52—Abstract.

Elstner, E. et al., "Ligands for peroxisome proliferator–activated receptorgamma and retinoic acid receptor inhibit growth and induce apoptosis of human breast cancer cells in vitro and in BNX mice," *Proc. Natl. Acad. Sci. USA*, Jul. 21, 1998, 95(15):8806–11—Abstract.

Lefebvre, A.M. et al., "Activation of the peroxisome proliferator–activated receptor gamma promotes the development of colon tumors in C57BL/6J–APCMin/+mice," *Nat. Med.*, Sep. 1998, 4(9):1053–7—Abstract.

Saez, E. et al., "Activators of the nuclear receptor PPAR-gamma enhance colon polyp formation," *Nat. Med.*, Sep. 1998, 4(9):1058–61—Abstract.

Mansen, A. et al., "Expression of the peroxisome proliferator–activated receptor (PPAR) in the mouse colonic mucosa," *Biochem. Biophys. Res. Commun.*, May 24, 1996, 222(3):844–51—Abstract.

Brockman, J.A. et al., Activation of PPARgamma leads to inhibition of anchorage–independent growth of human colorectal cancer cells, *Gastroenterology*, Nov. 1999, 115(5):1049–55.

DuBoise, R.N. et al., "The nuclear eicosanoid receptor, PPARgamma, is aberrantly expressed in colonic cancers," *Carcinogenesis*, Jan. 1998, 19(1):49–53—Abstract.

Fujimura, S. et al., "Effects of troglitazone on the growth and differentiation of hematopoietic cell lines," *Int. J. Oncol.*, Dec. 1998, 13(6):1263–7—Abstract.

Kitamura, S. et al., "Peroxisome proliferator–activated receptor gamma induces growth arrest and differentiation markers of human colon cancer cells," *Jpn. J. Cancer Res.*, Jan. 1999, 90(1):75–80 —Abstract.

Demetri, G.D. et al., "Induction of solid tumor differentiation by the peroxisome proliferator–activated receptor-gamma ligand troglitazone in patients with liposarcoma," *Proc. Natl. Acad. Sci. USA*, Mar. 30, 1999, 96(7):3951–6—Abstract.

Sarraf, P. et al., "Differentiation and reversal of malignant changes in colon cancer through PPARgamma," *Nat. Med.*, Sep. 1998, 4(9):1046–52—Abstract.

Ricote, M. et al., "The peroxisome proliferator–activated receptor–gamma is a negative regulator of macrophage activation," *Nature*, Jan. 1998, 391(6662):79–82—Abstract.

Su, C.G. et al., "A novel therapy for colitis utilizing PPAR-gamma ligands to inhibit the epithelial inflammatory response," *J. Clin. Invest.*, Aug. 1999, 104(4):383–9—Abstract.

Iijima, K. et al., "Expression of peroxisome proliferator–activated receptor gamma (PPARgamma) in rat aortic smooth muscle cells," *Biochem. Biophys. Res. Commun.*, Jun. 18, 1998, 247(2):353–6—Abstract.

Forman, B.M. et al., "15–Deoxy–delta 12, 14–prostaglandin J2 is a ligand for the adipocyte determination factor PPAR gamma," *Cell*, Dec. 1, 1995, 83(5):803–12—Abstract.

Schulman, I.G. et al., "Transactivation by retinoid X receptor–peroxisome proliferator–activated receptor gamma (PPARgamma) heterodimers: intermolecular synergy requires only the PPARgamma hormone–dependent activation function," *Mol. Cell Biol.*, Jun. 1998, 18(6):3483–94—Abstract.

Spiegelman, B.M. et al., "PPAR gamma and the control of adipogenesis," *Biochimie*, Feb.–Mar. 1997, 79(2–3):111–2—Abstract.

Freake, H.C., "A genetic mutation in PPAR gamma is associated with enhanced fat cell differentiation: implications for human obesity," *Nutr. Rev.*, May 1999, 57(5 Pt 1):154–6—Abstract.

Gorla–Bajszczak, A. et al., "Conserved amino acids in the ligand–binding and tau(i) domains of the peroxisome proliferator–activated receptor alpha are necessary for heterodimerization with RXR," *Mol. Cell Endocrinol.*, Jan. 25, 1999, 147(1–2):37–47—Abstract.

Robinson, C.E. et al., "DNA bending is induced by binding of the peroxisome proliferator–activated receptor gamma 2 heterodimer to its response element in the urine lipoprotein lipase promoter," *Biochem. Biophys. Res. Commun.*, Mar. 27, 1998, 244(3):671–7—Abstract.

Oberfield, J.L. et al., "A peroxisome proliferator–activated receptor gamma ligand inhibits adipocyte differentiation," *Proc. Natl. Acad. Sci. USA*, May 25, 1999, 96(11):6102–6—Abstract.

Palmer, C.N. et al., "Peroxisome proliferator activated receptor–alpha expression in human liver," *Mol. Pharmacol.*, Jan. 1998, 53(1):14–22—Abstract.

Grindflek, E. et al., "Characterisation of porcine peroxisome proliferator–activated receptors gamma 1 and gamma 2: detection of breed and age differences in gene expression," *Biochem. Biophys. Res. Common.*, Aug. 28, 1998, 249(3):713–8—Abstract.

Sundvold, H. et al., "Characterisation of bovine peroxisome proliferator–activated receptors gamma 1 and gamma 2: genetic mapping and differential expression of the two isoforms," *Biochem. Biophys. Res. Commun.*, Oct. 29, 1997, 239(3):857–61—Abstract.

Braissant, O. et al., "Differential expression of peroxisome proliferator–activated receptors (PRARs): tissue distribution of PPAR–alpha, –beta, and –gamma in the adult rat," *Endocrinology*, Jan. 1996, 137(1):354–66—Abstract.

Elbrecht, A. et al., "Molecular cloning, expression and characterization of human peroxisome proliferator activated receptors gamma 1 and gamma 2," *Biochem. Biophys. Res. Commun.*, Jul. 16, 1996, 224(2):431–7—Abstract.

Werman, A. et al., "Ligand–independent activation domain in the N terminus of peroxisome proliferator–activated receptor gamma (PPARgamma). Differential activity of PPARgamma1 and –2 isoforms and influence of insulin," *J. Biol. Chem.*, Aug. 8, 1997, 272(32):20230–5—Abstract.

Westin, S. et al., "Interactions controlling the assembly of nuclear–receptor heterodimers and co–activators," *Nature*, Sep. 10, 1998, 395(6698):199–202—Abstract.

Lehmann, J.M. et al., "An antidiabetic thiazolidinedione is a high affinity ligand for peroxisome proliferator–activated receptor gamma (PPAR gamma)," *J. Biol. Chem.*, Jun. 2, 1995, 270(22):12953–6—Abstract.

Kliewer, S.A. et al., "Differential expression and activation of a family of murine peroxisome proliferator–activated receptors," *Proc. Natl. Acad. Sci. USA*, Jul. 19, 1994, 91(15):7355–9—Abstract.

DiRenzo, J. et al., "Peroxisome proliferator–activated receptors and retinoic acid receptors differentially control the interactions of retinoid X receptor heterodimers with ligands, coactivators, and corepressors," *Mol. Cell Biol.*, Apr. 1997, 17(4):2166–76—Abstract.

Mizukami, J. et al., "The antidiabetic agent thiazolidenidione stimulates the interaction between PPAR gamma and CBP," *Biochem. Biophys. Res. Commun.*, Nov. 7, 1997, 240(1):61–4—Abstract.

Hsu, M.H. et al., "A carboxyl–terminal extension of the zinc finger domain contributes to the specificty and polarity of peroxisome proliferator–activated receptor DNA binding," *J. Biol. Chem.*, Oct. 23, 1998, 273(43):27988–97—Abstract.

Gelman, L. et al., "p300 interacts with the N– and C–terminal part of PPARgamma 2 in a ligand–independent and –dependent manner, respectively," *J. Biol. Chem.*, Mar. 19, 1999, 274(12):7681–8 —Abstract.

Wilson, T.M. et al., "Peroxisome proliferator–activated receptor agonists," *Curr. Opin. Chem. Biol.*, Aug. 1997, 1(2):235–41—Abstract.

Dowell, P. et al., "Identification of nuclear receptor corepressor as a peroxisome proliferator–activated receptor alpha interacting protein," *J. Biol. Chem.*, May 28, 1999, 274(22):15901–7—Abstract.

Auwerx, J. et al., "Regulation of triglyceride metabolism by PPARs: fibrates and thiazolidinediones have distinct effects," *J. Atheroscler. Thromb.*, 1996, 3(2):81–9—Abstract.

Berger, J. et al., "Novel peroxisome proliferator–activated receptor (PPAR) gamma and PPARdelta ligands produce distinct biological effects," *J. Biol. Chem.*, Mar. 5, 1999, 274(10):6718–25—Abstract.

Willson, T.M. et al., "Discovery of ligands for the nuclear peroxisome proliferator–activated receptors," *Ann. N.Y. Acad. Sci.*, Dec. 27, 1996, 804:276–83—Abstract.

Spiegelman, B.M., "PPAR–gamma: adipogenic regulator and thiazolidinedione receptor," *Diabetes*, Apr. 1998, 47(4):507–14—Abstract.

Spencer, C.M. et al., "Troglitazone," *Drugs*, Jul. 1997, 54(1):89–101, discussion 102—Abstract.

Shao, D. et al., "Interdomain communication regulating ligand binding by PPAR–gamma," *Nature*, Nov. 26, 1998, 396(6709):377–80—Abstract.

Nolte, R.T. et al., "Ligand binding and co–activator assembly of the peroxisome proliferator–activated receptor–gamma," *Nature*, Sep. 10, 1998, 395(6698):137–43—Abstract.

Schoonjans, K. et al., "Peroxisome proliferator–activated receptors, orphans with ligands and functions," *Curr. Opin. Lipidol.*, Jun. 1997, 8(3):159–66—Abstract.

Lin, Q. et al., "Ligand selectivity of the peroxisome proliferator–activated receptor alpha," *Biochemistry*, Jan. 5, 1999, 38(1):185–90—Abstract.

Kroll, T.G., et al, "PAX8–PPARγ1 fusion oncogen in human thyroid carcinoma," Science, 2000, vol. 289, No. 5483, pp. 1357–1360.

Mueller, E., et al, "Effects of ligand activation of peroxisome proliferator–activated receptor–γ in human prostate cancer," Proceedings of the National Academy of Sciences USA, 2000, vol. 97, No. 20, pp. 10990–10995.

Sidransky, D. "Nucleic acid–based methods for the detection of cancer," Science, 1997, vol. 278, pp. 1054–1058.

* cited by examiner

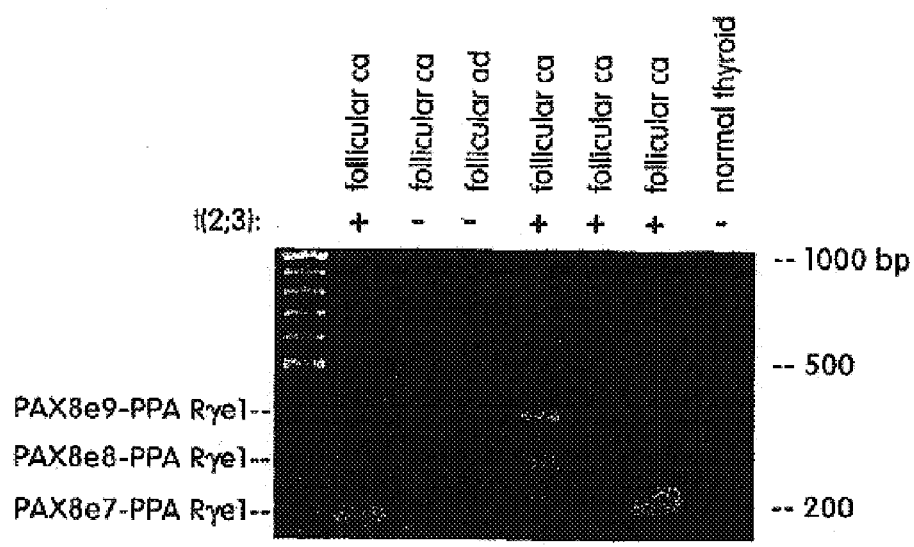
Fig. 4A
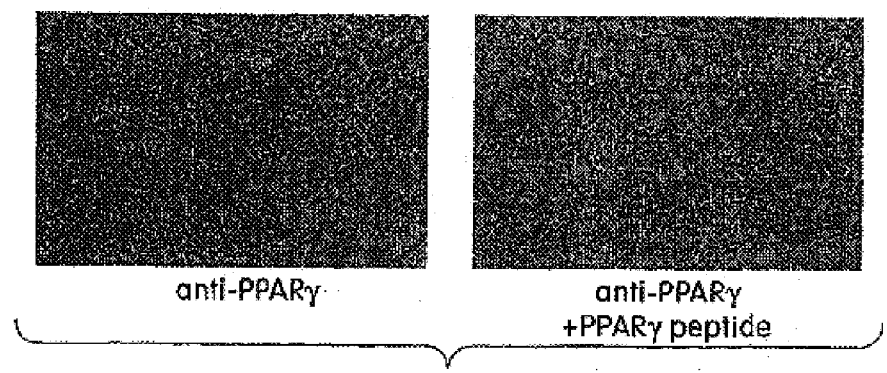
Fig. 4B
| THYROID NEOPLASM | RT-PCR | IMH |
|---|---|---|
| Follicular Carcinoma | 5/8 | 7/8 |
| Follicular Adenoma | 0/20 | 0/20 |
| Papillary Carcinoma | 0/10 | 0/10 |
| Multi-nodular Hyperplasia | 0/10 | 0/10 |
Fig. 4C

SEQUENCE LISTING

<160> NUMBER OF SEQ ID NOS: 47

<210> SEQ ID NO 1
<211> LENGTH: 2334
<212> TYPE: DNA
<213> ORGANISM: Homo Sapiens
<220> FEATURE:
<221> NAME/KEY: CDS
<222> LOCATION: (1)...(2334)

<400> SEQUENCE: 1

```
atg cct cac aac tcc atc aga tct ggc cat gga ggg ctg aac cag ctg      48
Met Pro His Asn Ser Ile Arg Ser Gly His Gly Gly Leu Asn Gln Leu
 1               5                  10                  15 gga ggg gcc ttt gtg aat ggc aga cct ctg ccg gaa gtg gtc cgc cag      96
Gly Gly Ala Phe Val Asn Gly Arg Pro Leu Pro Glu Val Val Arg Gln
             20                  25                  30 cgc atc gta gac ctg gcc cac cag ggt gta agg ccc tgc gac atc tct     144
Arg Ile Val Asp Leu Ala His Gln Gly Val Arg Pro Cys Asp Ile Ser
         35                  40                  45 cgc cag ctc cgc gtc agc cat ggc tgc gtc agc aag atc ctt ggc agg     192
Arg Gln Leu Arg Val Ser His Gly Cys Val Ser Lys Ile Leu Gly Arg
     50                  55                  60 tac tac gag act ggc agc atc cgg cct gga gtg ata ggg ggc tcc aag     240
Tyr Tyr Glu Thr Gly Ser Ile Arg Pro Gly Val Ile Gly Gly Ser Lys
 65                  70                  75                  80
```

| | | | | | | | | | | | | |
|---|---|---|---|---|---|---|---|---|---|---|---|---|
| ccc | aag | gtg | gcc | acc | ccc | aag | gtg | gtg | gag | aag | att | ggg | gac | tac | aaa | 288 |
| Pro | Lys | Val | Ala | Thr | Pro | Lys | Val | Val | Glu | Lys | Ile | Gly | Asp | Tyr | Lys |
| | | | | 85 | | | | | 90 | | | | | 95 | |

| cgc | cag | aac | cct | acc | atg | ttt | gcc | tgg | gag | atc | cga | gac | cgg | ctc | ctg | 336 |
| Arg | Gln | Asn | Pro | Thr | Met | Phe | Ala | Trp | Glu | Ile | Arg | Asp | Arg | Leu | Leu |
| | | | 100 | | | | | 105 | | | | | 110 | | |

| gct | gag | ggc | gtc | tgt | gac | aat | gac | act | gtg | ccc | agt | gtc | agc | tcc | att | 384 |
| Ala | Glu | Gly | Val | Cys | Asp | Asn | Asp | Thr | Val | Pro | Ser | Val | Ser | Ser | Ile |
| | | | 115 | | | | | 120 | | | | | 125 | | |

| aat | aga | atc | atc | cgg | acc | aaa | gtg | cag | caa | cca | ttc | aac | ctc | cct | atg | 432 |
| Asn | Arg | Ile | Ile | Arg | Thr | Lys | Val | Gln | Gln | Pro | Phe | Asn | Leu | Pro | Met |
| | 130 | | | | | 135 | | | | | 140 | | | | |

| gac | agc | tgc | gtg | gcc | acc | aag | tcc | ctg | agt | ccc | gga | cac | acg | ctg | atc | 480 |
| Asp | Ser | Cys | Val | Ala | Thr | Lys | Ser | Leu | Ser | Pro | Gly | His | Thr | Leu | Ile |
| 145 | | | | | 150 | | | | | 155 | | | | | 160 |

| ccc | agc | tca | gct | gta | act | ccc | ccg | gag | tca | ccc | cag | tcg | gat | tcc | ctg | 528 |
| Pro | Ser | Ser | Ala | Val | Thr | Pro | Pro | Glu | Ser | Pro | Gln | Ser | Asp | Ser | Leu |
| | | | | 165 | | | | | 170 | | | | | 175 | |

| ggc | tcc | acc | tac | tcc | atc | aat | ggg | ctc | ctg | ggc | atc | gct | cag | cct | ggc | 576 |
| Gly | Ser | Thr | Tyr | Ser | Ile | Asn | Gly | Leu | Leu | Gly | Ile | Ala | Gln | Pro | Gly |
| | | | 180 | | | | | 185 | | | | | 190 | | |

| agc | gac | aag | agg | aaa | atg | gat | gac | agt | gat | cag | gat | agc | tgc | cga | cta | 624 |
| Ser | Asp | Lys | Arg | Lys | Met | Asp | Asp | Ser | Asp | Gln | Asp | Ser | Cys | Arg | Leu |
| | | 195 | | | | | 200 | | | | | 205 | | | |

| agc | att | gac | tca | cag | agc | agc | agc | gga | ccc | cga | aag | cac | ctt | cgc | 672 |
| Ser | Ile | Asp | Ser | Gln | Ser | Ser | Ser | Gly | Pro | Arg | Lys | His | Leu | Arg |
| | 210 | | | | | 215 | | | | | 220 | | | | |

| acg | gat | gcc | ttc | agc | cag | cac | cac | ctc | gag | ccg | ctc | gag | tgc | cca | ttt | 720 |
| Thr | Asp | Ala | Phe | Ser | Gln | His | His | Leu | Glu | Pro | Leu | Glu | Cys | Pro | Phe |
| 225 | | | | | 230 | | | | | 235 | | | | | 240 |

| gag | cgg | cag | cac | tac | cca | gag | gcc | tat | gcc | tcc | ccc | agc | cac | acc | aaa | 768 |
| Glu | Arg | Gln | His | Tyr | Pro | Glu | Ala | Tyr | Ala | Ser | Pro | Ser | His | Thr | Lys |
| | | | | 245 | | | | | 250 | | | | | 255 | |

| ggc | gag | cag | ggc | ctc | tac | ccg | ctg | ccc | ttg | ctc | aac | agc | acc | ctg | gac | 816 |
| Gly | Glu | Gln | Gly | Leu | Tyr | Pro | Leu | Pro | Leu | Leu | Asn | Ser | Thr | Leu | Asp |
| | | | 260 | | | | | 265 | | | | | 270 | | |

| gac | ggg | aag | gcc | acc | ctg | acc | cct | tcc | aac | acg | cca | ctg | ggg | cgc | aac | 864 |
| Asp | Gly | Lys | Ala | Thr | Leu | Thr | Pro | Ser | Asn | Thr | Pro | Leu | Gly | Arg | Asn |
| | | 275 | | | | | 280 | | | | | 285 | | | |

| ctc | tcg | act | cac | cag | acc | tac | ccc | gtg | gtg | gca | gaa | atg | acc | atg | gtt | 912 |
| Leu | Ser | Thr | His | Gln | Thr | Tyr | Pro | Val | Val | Ala | Glu | Met | Thr | Met | Val |
| | 290 | | | | | 295 | | | | | 300 | | | | |

| gac | aca | gag | atg | cca | ttc | tgg | ccc | acc | aac | ttt | ggg | atc | agc | tcc | gtg | 960 |
| Asp | Thr | Glu | Met | Pro | Phe | Trp | Pro | Thr | Asn | Phe | Gly | Ile | Ser | Ser | Val |
| 305 | | | | | 310 | | | | | 315 | | | | | 320 |

| gat | ctc | tcc | gta | atg | gaa | gac | cac | tcc | cac | tcc | ttt | gat | atc | aag | ccc | 1008 |
| Asp | Leu | Ser | Val | Met | Glu | Asp | His | Ser | His | Ser | Phe | Asp | Ile | Lys | Pro |
| | | | | 325 | | | | | 330 | | | | | 335 | |

| ttc | act | act | gtt | gac | ttc | tcc | agc | att | tct | act | cca | cat | tac | gaa | gac | 1056 |
| Phe | Thr | Thr | Val | Asp | Phe | Ser | Ser | Ile | Ser | Thr | Pro | His | Tyr | Glu | Asp |
| | | | 340 | | | | | 345 | | | | | 350 | | |

| att | cca | ttc | aca | aga | aca | gat | cca | gtg | gtt | gca | gat | tac | aag | tat | gac | 1104 |
| Ile | Pro | Phe | Thr | Arg | Thr | Asp | Pro | Val | Val | Ala | Asp | Tyr | Lys | Tyr | Asp |
| | | 355 | | | | | 360 | | | | | 365 | | | |

| ctg | aaa | ctt | caa | gag | tac | caa | agt | gca | atc | aaa | gtg | gag | cct | gca | tct | 1152 |
| Leu | Lys | Leu | Gln | Glu | Tyr | Gln | Ser | Ala | Ile | Lys | Val | Glu | Pro | Ala | Ser |
| 370 | | | | | 375 | | | | | 380 | | | | | |

| cca | cct | tat | tat | tct | gag | aag | act | cag | ctc | tac | aat | aag | cct | cat | gaa | 1200 |
| Pro | Pro | Tyr | Tyr | Ser | Glu | Lys | Thr | Gln | Leu | Tyr | Asn | Lys | Pro | His | Glu |

```
                385                 390                 395                 400
gag cct tcc aac tcc ctc atg gca att gaa tgt cgt gtc tgt gga gat        1248
Glu Pro Ser Asn Ser Leu Met Ala Ile Glu Cys Arg Val Cys Gly Asp
                    405                 410                 415 aaa gct tct gga ttt cac tat gga gtt cat gct tgt gaa gga tgc aag        1296
Lys Ala Ser Gly Phe His Tyr Gly Val His Ala Cys Glu Gly Cys Lys
                420                 425                 430 ggt ttc ttc cgg aga aca atc aga ttg aag ctt atc tat gac aga tgt        1344
Gly Phe Phe Arg Arg Thr Ile Arg Leu Lys Leu Ile Tyr Asp Arg Cys
            435                 440                 445 gat ctt aac tgt cgg atc cac aaa aaa agt aga aat aaa tgt cag tac        1392
Asp Leu Asn Cys Arg Ile His Lys Lys Ser Arg Asn Lys Cys Gln Tyr
        450                 455                 460 tgt cgg ttt cag aaa tgc ctt gca gtg ggg atg tct cat aat gcc atc        1440
Cys Arg Phe Gln Lys Cys Leu Ala Val Gly Met Ser His Asn Ala Ile
465                 470                 475                 480 agg ttt ggg cgg atg cca cag gcc gag aag gag aag ctg ttg gcg gag        1488
Arg Phe Gly Arg Met Pro Gln Ala Glu Lys Glu Lys Leu Leu Ala Glu
                    485                 490                 495 atc tcc agt gat atc gac cag ctg aat cca gag tcc gct gac ctc cgg        1536
Ile Ser Ser Asp Ile Asp Gln Leu Asn Pro Glu Ser Ala Asp Leu Arg
                500                 505                 510 gcc ctg gca aaa cat ttg tat gac tca tac ata aag tcc ttc ccg ctg        1584
Ala Leu Ala Lys His Leu Tyr Asp Ser Tyr Ile Lys Ser Phe Pro Leu
            515                 520                 525 acc aaa gca aag gcg agg gcg atc ttg aca gga aag aca aca gac aaa        1632
Thr Lys Ala Lys Ala Arg Ala Ile Leu Thr Gly Lys Thr Thr Asp Lys
        530                 535                 540 tca cca ttc gtt atc tat gac atg aat tcc tta atg atg gga gaa gat        1680
Ser Pro Phe Val Ile Tyr Asp Met Asn Ser Leu Met Met Gly Glu Asp
545                 550                 555                 560 aaa atc aag ttc aaa cac atc acc ccc ctg cag gag cag agc aaa gag        1728
Lys Ile Lys Phe Lys His Ile Thr Pro Leu Gln Glu Gln Ser Lys Glu
                    565                 570                 575 gtg gcc atc cgc atc ttt cag ggc tgc cag ttt cgc tcc gtg gag gct        1776
Val Ala Ile Arg Ile Phe Gln Gly Cys Gln Phe Arg Ser Val Glu Ala
                580                 585                 590 gtg cag gag atc aca gag tat gcc aaa agc att cct ggt ttt gta aat        1824
Val Gln Glu Ile Thr Glu Tyr Ala Lys Ser Ile Pro Gly Phe Val Asn
            595                 600                 605 ctt gac ttg aac gac caa gta act ctc ctc aaa tat gga gtc cac gag        1872
Leu Asp Leu Asn Asp Gln Val Thr Leu Leu Lys Tyr Gly Val His Glu
        610                 615                 620 atc att tac aca atg ctg gcc tcc ttg atg aat aaa gat ggg gtt ctc        1920
Ile Ile Tyr Thr Met Leu Ala Ser Leu Met Asn Lys Asp Gly Val Leu
625                 630                 635                 640 ata tcc gag ggc caa ggc ttc atg aca agg gag ttt cta aag agc ctg        1968
Ile Ser Glu Gly Gln Gly Phe Met Thr Arg Glu Phe Leu Lys Ser Leu
                    645                 650                 655 cga aag cct ttt ggt gac ttt atg gag ccc aag ttt gag ttt gct gtg        2016
Arg Lys Pro Phe Gly Asp Phe Met Glu Pro Lys Phe Glu Phe Ala Val
                660                 665                 670 aag ttc aat gca ctg gaa tta gat gac agc gac ttg gca ata ttt att        2064
Lys Phe Asn Ala Leu Glu Leu Asp Asp Ser Asp Leu Ala Ile Phe Ile
            675                 680                 685 gct gtc att att ctc agt gga gac cgc cca ggt ttg ctg aat gtg aag        2112
Ala Val Ile Ile Leu Ser Gly Asp Arg Pro Gly Leu Leu Asn Val Lys
        690                 695                 700 ccc att gaa gac att caa gac aac ctg cta caa gcc ctg gag ctc cag        2160
```

```
Pro Ile Glu Asp Ile Gln Asp Asn Leu Leu Gln Ala Leu Glu Leu Gln
705                 710                 715                 720 ctg aag ctg aac cac cct gag tcc tca cag ctg ttt gcc aag ctg ctc    2208
Leu Lys Leu Asn His Pro Glu Ser Ser Gln Leu Phe Ala Lys Leu Leu
                725                 730                 735 cag aaa atg aca gac ctc aga cag att gtc acg gaa cac gtg cag cta    2256
Gln Lys Met Thr Asp Leu Arg Gln Ile Val Thr Glu His Val Gln Leu
            740                 745                 750 ctg cag gtg atc aag aag acg gag aca gac atg agt ctt cac ccg ctc    2304
Leu Gln Val Ile Lys Lys Thr Glu Thr Asp Met Ser Leu His Pro Leu
        755                 760                 765 ctg cag gag atc tac aag gac ttg tac tag                            2334
Leu Gln Glu Ile Tyr Lys Asp Leu Tyr *
    770                 775
```

<210> SEQ ID NO 2
<211> LENGTH: 777
<212> TYPE: PRT
<213> ORGANISM: Homo Sapiens

<400> SEQUENCE: 2

```
Met Pro His Asn Ser Ile Arg Ser Gly His Gly Gly Leu Asn Gln Leu
1               5                   10                  15

Gly Gly Ala Phe Val Asn Gly Arg Pro Leu Pro Glu Val Val Arg Gln
            20                  25                  30

Arg Ile Val Asp Leu Ala His Gln Gly Val Arg Pro Cys Asp Ile Ser
        35                  40                  45

Arg Gln Leu Arg Val Ser His Gly Cys Val Ser Lys Ile Leu Gly Arg
    50                  55                  60

Tyr Tyr Glu Thr Gly Ser Ile Arg Pro Gly Val Ile Gly Gly Ser Lys
65                  70                  75                  80

Pro Lys Val Ala Thr Pro Lys Val Val Glu Lys Ile Gly Asp Tyr Lys
                85                  90                  95

Arg Gln Asn Pro Thr Met Phe Ala Trp Glu Ile Arg Asp Arg Leu Leu
            100                 105                 110

Ala Glu Gly Val Cys Asp Asn Asp Thr Val Pro Ser Val Ser Ser Ile
        115                 120                 125

Asn Arg Ile Ile Arg Thr Lys Val Gln Gln Pro Phe Asn Leu Pro Met
    130                 135                 140

Asp Ser Cys Val Ala Thr Lys Ser Leu Ser Pro Gly His Thr Leu Ile
145                 150                 155                 160

Pro Ser Ser Ala Val Thr Pro Pro Glu Ser Pro Gln Ser Asp Ser Leu
                165                 170                 175

Gly Ser Thr Tyr Ser Ile Asn Gly Leu Leu Gly Ile Ala Gln Pro Gly
            180                 185                 190

Ser Asp Lys Arg Lys Met Asp Asp Ser Asp Gln Asp Ser Cys Arg Leu
        195                 200                 205

Ser Ile Asp Ser Gln Ser Ser Ser Ser Gly Pro Arg Lys His Leu Arg
    210                 215                 220

Thr Asp Ala Phe Ser Gln His His Leu Glu Pro Leu Glu Cys Pro Phe
225                 230                 235                 240

Glu Arg Gln His Tyr Pro Glu Ala Tyr Ala Ser Pro Ser His Thr Lys
                245                 250                 255

Gly Glu Gln Gly Leu Tyr Pro Leu Pro Leu Leu Asn Ser Thr Leu Asp
            260                 265                 270

Asp Gly Lys Ala Thr Leu Thr Pro Ser Asn Thr Pro Leu Gly Arg Asn
```

-continued

```
                275                 280                 285
Leu Ser Thr His Gln Thr Tyr Pro Val Ala Glu Met Thr Met Val
    290                 295                 300
Asp Thr Glu Met Pro Phe Trp Pro Thr Asn Phe Gly Ile Ser Ser Val
305                 310                 315                 320
Asp Leu Ser Val Met Glu Asp His Ser His Ser Phe Asp Ile Lys Pro
                325                 330                 335
Phe Thr Thr Val Asp Phe Ser Ser Ile Ser Thr Pro His Tyr Glu Asp
                340                 345                 350
Ile Pro Phe Thr Arg Thr Asp Pro Val Val Ala Asp Tyr Lys Tyr Asp
                355                 360                 365
Leu Lys Leu Gln Glu Tyr Gln Ser Ala Ile Lys Val Glu Pro Ala Ser
    370                 375                 380
Pro Pro Tyr Tyr Ser Glu Lys Thr Gln Leu Tyr Asn Lys Pro His Glu
385                 390                 395                 400
Glu Pro Ser Asn Ser Leu Met Ala Ile Glu Cys Arg Val Cys Gly Asp
                405                 410                 415
Lys Ala Ser Gly Phe His Tyr Gly Val His Ala Cys Glu Gly Cys Lys
                420                 425                 430
Gly Phe Phe Arg Arg Thr Ile Arg Leu Lys Leu Ile Tyr Asp Arg Cys
                435                 440                 445
Asp Leu Asn Cys Arg Ile His Lys Lys Ser Arg Asn Lys Cys Gln Tyr
    450                 455                 460
Cys Arg Phe Gln Lys Cys Leu Ala Val Gly Met Ser His Asn Ala Ile
465                 470                 475                 480
Arg Phe Gly Arg Met Pro Gln Ala Glu Lys Glu Lys Leu Leu Ala Glu
                485                 490                 495
Ile Ser Ser Asp Ile Asp Gln Leu Asn Pro Glu Ser Ala Asp Leu Arg
                500                 505                 510
Ala Leu Ala Lys His Leu Tyr Asp Ser Tyr Ile Lys Ser Phe Pro Leu
                515                 520                 525
Thr Lys Ala Lys Ala Arg Ala Ile Leu Thr Gly Lys Thr Thr Asp Lys
    530                 535                 540
Ser Pro Phe Val Ile Tyr Asp Met Asn Ser Leu Met Met Gly Glu Asp
545                 550                 555                 560
Lys Ile Lys Phe Lys His Ile Thr Pro Leu Gln Glu Gln Ser Lys Glu
                565                 570                 575
Val Ala Ile Arg Ile Phe Gln Gly Cys Gln Phe Arg Ser Val Glu Ala
                580                 585                 590
Val Gln Glu Ile Thr Glu Tyr Ala Lys Ser Ile Pro Gly Phe Val Asn
    595                 600                 605
Leu Asp Leu Asn Asp Gln Val Thr Leu Leu Lys Tyr Gly Val His Glu
    610                 615                 620
Ile Ile Tyr Thr Met Leu Ala Ser Leu Met Asn Lys Asp Gly Val Leu
625                 630                 635                 640
Ile Ser Glu Gly Gln Gly Phe Met Thr Arg Glu Phe Leu Lys Ser Leu
                645                 650                 655
Arg Lys Pro Phe Gly Asp Phe Met Glu Pro Lys Phe Glu Phe Ala Val
                660                 665                 670
Lys Phe Asn Ala Leu Glu Leu Asp Asp Ser Asp Leu Ala Ile Phe Ile
                675                 680                 685
Ala Val Ile Ile Leu Ser Gly Asp Arg Pro Gly Leu Leu Asn Val Lys
    690                 695                 700
```

```
Pro Ile Glu Asp Ile Gln Asp Asn Leu Leu Gln Ala Leu Glu Leu Gln
705                 710                 715                 720

Leu Lys Leu Asn His Pro Glu Ser Ser Gln Leu Phe Ala Lys Leu Leu
            725                 730                 735

Gln Lys Met Thr Asp Leu Arg Gln Ile Val Thr Glu His Val Gln Leu
        740                 745                 750

Leu Gln Val Ile Lys Lys Thr Glu Thr Asp Met Ser Leu His Pro Leu
    755                 760                 765

Leu Gln Glu Ile Tyr Lys Asp Leu Tyr
    770                 775

<210> SEQ ID NO 3
<211> LENGTH: 2523
<212> TYPE: DNA
<213> ORGANISM: Homo Sapiens
<220> FEATURE:
<221> NAME/KEY: CDS
<222> LOCATION: (1)...(2523)

<400> SEQUENCE: 3 atg cct cac aac tcc atc aga tct ggc cat gga ggg ctg aac cag ctg       48
Met Pro His Asn Ser Ile Arg Ser Gly His Gly Gly Leu Asn Gln Leu
1               5                   10                  15 gga ggg gcc ttt gtg aat ggc aga cct ctg ccg gaa gtg gtc cgc cag       96
Gly Gly Ala Phe Val Asn Gly Arg Pro Leu Pro Glu Val Val Arg Gln
            20                  25                  30 cgc atc gta gac ctg gcc cac cag ggt gta agg ccc tgc gac atc tct      144
Arg Ile Val Asp Leu Ala His Gln Gly Val Arg Pro Cys Asp Ile Ser
        35                  40                  45 cgc cag ctc cgc gtc agc cat ggc tgc gtc agc aag atc ctt ggc agg      192
Arg Gln Leu Arg Val Ser His Gly Cys Val Ser Lys Ile Leu Gly Arg
    50                  55                  60 tac tac gag act ggc agc atc cgg cct gga gtg ata ggg ggc tcc aag      240
Tyr Tyr Glu Thr Gly Ser Ile Arg Pro Gly Val Ile Gly Gly Ser Lys
65                  70                  75                  80 ccc aag gtg gcc acc ccc aag gtg gtg gag aag att ggg gac tac aaa      288
Pro Lys Val Ala Thr Pro Lys Val Val Glu Lys Ile Gly Asp Tyr Lys
                85                  90                  95 cgc cag aac cct acc atg ttt gcc tgg gag atc cga gac cgg ctc ctg      336
Arg Gln Asn Pro Thr Met Phe Ala Trp Glu Ile Arg Asp Arg Leu Leu
            100                 105                 110 gct gag ggc gtc tgt gac aat gac act gtg ccc agt gtc agc tcc att      384
Ala Glu Gly Val Cys Asp Asn Asp Thr Val Pro Ser Val Ser Ser Ile
        115                 120                 125 aat aga atc atc cgg acc aaa gtg cag caa cca ttc aac ctc cct atg      432
Asn Arg Ile Ile Arg Thr Lys Val Gln Gln Pro Phe Asn Leu Pro Met
    130                 135                 140 gac agc tgc gtg gcc acc aag tcc ctg agt ccc gga cac acg ctg atc      480
Asp Ser Cys Val Ala Thr Lys Ser Leu Ser Pro Gly His Thr Leu Ile
145                 150                 155                 160 ccc agc tca gct gta act ccc ccg gag tca ccc cag tcg gat tcc ctg      528
Pro Ser Ser Ala Val Thr Pro Pro Glu Ser Pro Gln Ser Asp Ser Leu
                165                 170                 175 ggc tcc acc tac tcc atc aat ggg ctc ctg ggc atc gct cag cct ggc      576
Gly Ser Thr Tyr Ser Ile Asn Gly Leu Leu Gly Ile Ala Gln Pro Gly
            180                 185                 190 agc gac aag agg aaa atg gat gac agt gat cag gat agc tgc cga cta      624
Ser Asp Lys Arg Lys Met Asp Asp Ser Asp Gln Asp Ser Cys Arg Leu
        195                 200                 205
```

-continued

```
agc att gac tca cag agc agc agc gga ccc cga aag cac ctt cgc        672
Ser Ile Asp Ser Gln Ser Ser Ser Gly Pro Arg Lys His Leu Arg
    210                 215                 220 acg gat gcc ttc agc cag cac cac ctc gag ccg ctc gag tgc cca ttt    720
Thr Asp Ala Phe Ser Gln His His Leu Glu Pro Leu Glu Cys Pro Phe
225                 230                 235                 240 gag cgg cag cac tac cca gag gcc tat gcc tcc ccc agc cac acc aaa    768
Glu Arg Gln His Tyr Pro Glu Ala Tyr Ala Ser Pro Ser His Thr Lys
                245                 250                 255 ggc gag cag ggc ctc tac ccg ctg ccc ttg ctc aac agc acc ctg gac    816
Gly Glu Gln Gly Leu Tyr Pro Leu Pro Leu Leu Asn Ser Thr Leu Asp
            260                 265                 270 gac ggg aag gcc acc ctg acc cct tcc aac acg cca ctg ggg cgc aac    864
Asp Gly Lys Ala Thr Leu Thr Pro Ser Asn Thr Pro Leu Gly Arg Asn
        275                 280                 285 ctc tcg act cac cag acc tac ccc gtg gtg gca gat cct cac tca ccc    912
Leu Ser Thr His Gln Thr Tyr Pro Val Val Ala Asp Pro His Ser Pro
    290                 295                 300 ttg gcc ata aag cag gaa acc ccc gag gtg tcc agt tct agc tcc acc    960
Leu Ala Ile Lys Gln Glu Thr Pro Glu Val Ser Ser Ser Ser Ser Thr
305                 310                 315                 320 cct tgc tct tta tct agc tcc gcc ctt ttg gat ctg cag caa gtc ggc    1008
Pro Cys Ser Leu Ser Ser Ser Ala Leu Leu Asp Leu Gln Gln Val Gly
                325                 330                 335 tcc ggg gtc ccg ccc ttc aat gcc ttt ccc cat gct gcc tcc gtg tac    1056
Ser Gly Val Pro Pro Phe Asn Ala Phe Pro His Ala Ala Ser Val Tyr
            340                 345                 350 ggg cag ttc acg ggc cag gcc ctc ctc tca gaa atg acc atg gtt gac    1104
Gly Gln Phe Thr Gly Gln Ala Leu Leu Ser Glu Met Thr Met Val Asp
        355                 360                 365 aca gag atg cca ttc tgg ccc acc aac ttt ggg atc agc tcc gtg gat    1152
Thr Glu Met Pro Phe Trp Pro Thr Asn Phe Gly Ile Ser Ser Val Asp
    370                 375                 380 ctc tcc gta atg gaa gac cac tcc cac tcc ttt gat atc aag ccc ttc    1200
Leu Ser Val Met Glu Asp His Ser His Ser Phe Asp Ile Lys Pro Phe
385                 390                 395                 400 act act gtt gac ttc tcc agc att tct act cca cat tac gaa gac att    1248
Thr Thr Val Asp Phe Ser Ser Ile Ser Thr Pro His Tyr Glu Asp Ile
                405                 410                 415 cca ttc aca aga aca gat cca gtg gtt gca gat tac aag tat gac ctg    1296
Pro Phe Thr Arg Thr Asp Pro Val Val Ala Asp Tyr Lys Tyr Asp Leu
            420                 425                 430 aaa ctt caa gag tac caa agt gca atc aaa gtg gag cct gca tct cca    1344
Lys Leu Gln Glu Tyr Gln Ser Ala Ile Lys Val Glu Pro Ala Ser Pro
        435                 440                 445 cct tat tat tct gag aag act cag ctc tac aat aag cct cat gaa gag    1392
Pro Tyr Tyr Ser Glu Lys Thr Gln Leu Tyr Asn Lys Pro His Glu Glu
    450                 455                 460 cct tcc aac tcc ctc atg gca att gaa tgt cgt gtc tgt gga gat aaa    1440
Pro Ser Asn Ser Leu Met Ala Ile Glu Cys Arg Val Cys Gly Asp Lys
465                 470                 475                 480 gct tct gga ttt cac tat gga gtt cat gct tgt gaa gga tgc aag ggt    1488
Ala Ser Gly Phe His Tyr Gly Val His Ala Cys Glu Gly Cys Lys Gly
                485                 490                 495 ttc ttc cgg aga aca atc aga ttg aag ctt atc tat gac aga tgt gat    1536
Phe Phe Arg Arg Thr Ile Arg Leu Lys Leu Ile Tyr Asp Arg Cys Asp
            500                 505                 510 ctt aac tgt cgg atc cac aaa aaa agt aga aat aaa tgt cag tac tgt    1584
Leu Asn Cys Arg Ile His Lys Lys Ser Arg Asn Lys Cys Gln Tyr Cys
        515                 520                 525
```

```
cgg ttt cag aaa tgc ctt gca gtg ggg atg tct cat aat gcc atc agg         1632
Arg Phe Gln Lys Cys Leu Ala Val Gly Met Ser His Asn Ala Ile Arg
        530                 535                 540 ttt ggg cgg atg cca cag gcc gag aag gag aag ctg ttg gcg gag atc         1680
Phe Gly Arg Met Pro Gln Ala Glu Lys Glu Lys Leu Leu Ala Glu Ile
545                 550                 555                 560 tcc agt gat atc gac cag ctg aat cca gag tcc gct gac ctc cgg gcc         1728
Ser Ser Asp Ile Asp Gln Leu Asn Pro Glu Ser Ala Asp Leu Arg Ala
                565                 570                 575 ctg gca aaa cat ttg tat gac tca tac ata aag tcc ttc ccg ctg acc         1776
Leu Ala Lys His Leu Tyr Asp Ser Tyr Ile Lys Ser Phe Pro Leu Thr
                580                 585                 590 aaa gca aag gcg agg gcg atc ttg aca gga aag aca aca gac aaa tca         1824
Lys Ala Lys Ala Arg Ala Ile Leu Thr Gly Lys Thr Thr Asp Lys Ser
            595                 600                 605 cca ttc gtt atc tat gac atg aat tcc tta atg atg gga gaa gat aaa         1872
Pro Phe Val Ile Tyr Asp Met Asn Ser Leu Met Met Gly Glu Asp Lys
610                 615                 620 atc aag ttc aaa cac atc acc ccc ctg cag gag cag agc aaa gag gtg         1920
Ile Lys Phe Lys His Ile Thr Pro Leu Gln Glu Gln Ser Lys Glu Val
625                 630                 635                 640 gcc atc cgc atc ttt cag ggc tgc cag ttt cgc tcc gtg gag gct gtg         1968
Ala Ile Arg Ile Phe Gln Gly Cys Gln Phe Arg Ser Val Glu Ala Val
                645                 650                 655 cag gag atc aca gag tat gcc aaa agc att cct ggt ttt gta aat ctt         2016
Gln Glu Ile Thr Glu Tyr Ala Lys Ser Ile Pro Gly Phe Val Asn Leu
                660                 665                 670 gac ttg aac gac caa gta act ctc ctc aaa tat gga gtc cac gag atc         2064
Asp Leu Asn Asp Gln Val Thr Leu Leu Lys Tyr Gly Val His Glu Ile
            675                 680                 685 att tac aca atg ctg gcc tcc ttg atg aat aaa gat ggg gtt ctc ata         2112
Ile Tyr Thr Met Leu Ala Ser Leu Met Asn Lys Asp Gly Val Leu Ile
690                 695                 700 tcc gag ggc caa ggc ttc atg aca agg gag ttt cta aag agc ctg cga         2160
Ser Glu Gly Gln Gly Phe Met Thr Arg Glu Phe Leu Lys Ser Leu Arg
705                 710                 715                 720 aag cct ttt ggt gac ttt atg gag ccc aag ttt gag ttt gct gtg aag         2208
Lys Pro Phe Gly Asp Phe Met Glu Pro Lys Phe Glu Phe Ala Val Lys
                725                 730                 735 ttc aat gca ctg gaa tta gat gac agc gac ttg gca ata ttt att gct         2256
Phe Asn Ala Leu Glu Leu Asp Asp Ser Asp Leu Ala Ile Phe Ile Ala
            740                 745                 750 gtc att att ctc agt gga gac cgc cca ggt ttg ctg aat gtg aag ccc         2304
Val Ile Ile Leu Ser Gly Asp Arg Pro Gly Leu Leu Asn Val Lys Pro
755                 760                 765 att gaa gac att caa gac aac ctg cta caa gcc ctg gag ctc cag ctg         2352
Ile Glu Asp Ile Gln Asp Asn Leu Leu Gln Ala Leu Glu Leu Gln Leu
770                 775                 780 aag ctg aac cac cct gag tcc tca cag ctg ttt gcc aag ctg ctc cag         2400
Lys Leu Asn His Pro Glu Ser Ser Gln Leu Phe Ala Lys Leu Leu Gln
785                 790                 795                 800 aaa atg aca gac ctc aga cag att gtc acg gaa cac gtg cag cta ctg         2448
Lys Met Thr Asp Leu Arg Gln Ile Val Thr Glu His Val Gln Leu Leu
                805                 810                 815 cag gtg atc aag aag acg gag aca gac atg agt ctt cac ccg ctc ctg         2496
Gln Val Ile Lys Lys Thr Glu Thr Asp Met Ser Leu His Pro Leu Leu
            820                 825                 830 cag gag atc tac aag gac ttg tac tag                                     2523
Gln Glu Ile Tyr Lys Asp Leu Tyr *
```

```
                835                 840

<210> SEQ ID NO 4
<211> LENGTH: 840
<212> TYPE: PRT
<213> ORGANISM: Homo Sapiens

<400> SEQUENCE: 4

Met Pro His Asn Ser Ile Arg Ser Gly His Gly Leu Asn Gln Leu
 1               5                  10                  15

Gly Gly Ala Phe Val Asn Gly Arg Pro Leu Pro Glu Val Val Arg Gln
                20                  25                  30

Arg Ile Val Asp Leu Ala His Gln Gly Val Arg Pro Cys Asp Ile Ser
                35                  40                  45

Arg Gln Leu Arg Val Ser His Gly Cys Val Ser Lys Ile Leu Gly Arg
            50                  55                  60

Tyr Tyr Glu Thr Gly Ser Ile Arg Pro Gly Val Ile Gly Gly Ser Lys
65                  70                  75                  80

Pro Lys Val Ala Thr Pro Lys Val Val Glu Lys Ile Gly Asp Tyr Lys
                85                  90                  95

Arg Gln Asn Pro Thr Met Phe Ala Trp Glu Ile Arg Asp Arg Leu Leu
                100                 105                 110

Ala Glu Gly Val Cys Asp Asn Asp Thr Val Pro Ser Val Ser Ser Ile
                115                 120                 125

Asn Arg Ile Ile Arg Thr Lys Val Gln Gln Pro Phe Asn Leu Pro Met
            130                 135                 140

Asp Ser Cys Val Ala Thr Lys Ser Leu Ser Pro Gly His Thr Leu Ile
145                 150                 155                 160

Pro Ser Ser Ala Val Thr Pro Pro Glu Ser Pro Gln Ser Asp Ser Leu
                165                 170                 175

Gly Ser Thr Tyr Ser Ile Asn Gly Leu Leu Gly Ile Ala Gln Pro Gly
                180                 185                 190

Ser Asp Lys Arg Lys Met Asp Asp Ser Asp Gln Asp Ser Cys Arg Leu
                195                 200                 205

Ser Ile Asp Ser Gln Ser Ser Ser Ser Gly Pro Arg Lys His Leu Arg
            210                 215                 220

Thr Asp Ala Phe Ser Gln His His Leu Glu Pro Leu Glu Cys Pro Phe
225                 230                 235                 240

Glu Arg Gln His Tyr Pro Glu Ala Tyr Ala Ser Pro Ser His Thr Lys
                245                 250                 255

Gly Glu Gln Gly Leu Tyr Pro Leu Pro Leu Leu Asn Ser Thr Leu Asp
                260                 265                 270

Asp Gly Lys Ala Thr Leu Thr Pro Ser Asn Thr Pro Leu Gly Arg Asn
            275                 280                 285

Leu Ser Thr His Gln Thr Tyr Pro Val Val Ala Asp Pro His Ser Pro
    290                 295                 300

Leu Ala Ile Lys Gln Glu Thr Pro Glu Val Ser Ser Ser Ser Ser Thr
305                 310                 315                 320

Pro Cys Ser Leu Ser Ser Ser Ala Leu Leu Asp Leu Gln Gln Val Gly
                325                 330                 335

Ser Gly Val Pro Pro Phe Asn Ala Phe Pro His Ala Ala Ser Val Tyr
                340                 345                 350

Gly Gln Phe Thr Gly Gln Ala Leu Leu Ser Glu Met Thr Met Val Asp
                355                 360                 365
```

-continued

```
Thr Glu Met Pro Phe Trp Pro Thr Asn Phe Gly Ile Ser Ser Val Asp
    370                 375                 380

Leu Ser Val Met Glu Asp His Ser His Ser Phe Asp Ile Lys Pro Phe
385                 390                 395                 400

Thr Thr Val Asp Phe Ser Ser Ile Ser Thr Pro His Tyr Glu Asp Ile
                    405                 410                 415

Pro Phe Thr Arg Thr Asp Pro Val Val Ala Asp Tyr Lys Tyr Asp Leu
                420                 425                 430

Lys Leu Gln Glu Tyr Gln Ser Ala Ile Lys Val Glu Pro Ala Ser Pro
            435                 440                 445

Pro Tyr Tyr Ser Glu Lys Thr Gln Leu Tyr Asn Lys Pro His Glu Glu
        450                 455                 460

Pro Ser Asn Ser Leu Met Ala Ile Glu Cys Arg Val Cys Gly Asp Lys
465                 470                 475                 480

Ala Ser Gly Phe His Tyr Gly Val His Ala Cys Glu Gly Cys Lys Gly
                    485                 490                 495

Phe Phe Arg Arg Thr Ile Arg Leu Lys Leu Ile Tyr Asp Arg Cys Asp
                500                 505                 510

Leu Asn Cys Arg Ile His Lys Lys Ser Arg Asn Lys Cys Gln Tyr Cys
            515                 520                 525

Arg Phe Gln Lys Cys Leu Ala Val Gly Met Ser His Asn Ala Ile Arg
        530                 535                 540

Phe Gly Arg Met Pro Gln Ala Glu Lys Glu Lys Leu Leu Ala Glu Ile
545                 550                 555                 560

Ser Ser Asp Ile Asp Gln Leu Asn Pro Glu Ser Ala Asp Leu Arg Ala
                    565                 570                 575

Leu Ala Lys His Leu Tyr Asp Ser Tyr Ile Lys Ser Phe Pro Leu Thr
                580                 585                 590

Lys Ala Lys Ala Arg Ala Ile Leu Thr Gly Lys Thr Thr Asp Lys Ser
            595                 600                 605

Pro Phe Val Ile Tyr Asp Met Asn Ser Leu Met Met Gly Glu Asp Lys
        610                 615                 620

Ile Lys Phe Lys His Ile Thr Pro Leu Gln Glu Gln Ser Lys Glu Val
625                 630                 635                 640

Ala Ile Arg Ile Phe Gln Gly Cys Gln Phe Arg Ser Val Glu Ala Val
                    645                 650                 655

Gln Glu Ile Thr Glu Tyr Ala Lys Ser Ile Pro Gly Phe Val Asn Leu
                660                 665                 670

Asp Leu Asn Asp Gln Val Thr Leu Leu Lys Tyr Gly Val His Glu Ile
            675                 680                 685

Ile Tyr Thr Met Leu Ala Ser Leu Met Asn Lys Asp Gly Val Leu Ile
        690                 695                 700

Ser Glu Gly Gln Gly Phe Met Thr Arg Glu Phe Leu Lys Ser Leu Arg
705                 710                 715                 720

Lys Pro Phe Gly Asp Phe Met Glu Pro Lys Phe Glu Phe Ala Val Lys
                    725                 730                 735

Phe Asn Ala Leu Glu Leu Asp Asp Ser Asp Leu Ala Ile Phe Ile Ala
                740                 745                 750

Val Ile Ile Leu Ser Gly Asp Arg Pro Gly Leu Leu Asn Val Lys Pro
            755                 760                 765

Ile Glu Asp Ile Gln Asp Asn Leu Leu Gln Ala Leu Glu Leu Gln Leu
        770                 775                 780

Lys Leu Asn His Pro Glu Ser Ser Gln Leu Phe Ala Lys Leu Leu Gln
```

```
                    785                 790                  795                 800
           Lys Met Thr Asp Leu Arg Gln Ile Val Thr Glu His Val Gln Leu Leu
                           805                  810                 815

Gln Val Ile Lys Lys Thr Glu Thr Asp Met Ser Leu His Pro Leu Leu
                           820                  825                 830

Gln Glu Ile Tyr Lys Asp Leu Tyr
                           835                  840

<210> SEQ ID NO 5
<211> LENGTH: 2625
<212> TYPE: DNA
<213> ORGANISM: Homo Sapiens
<220> FEATURE:
<221> NAME/KEY: CDS
<222> LOCATION: (1)...(2625)

<400> SEQUENCE: 5 atg cct cac aac tcc atc aga tct ggc cat gga ggg ctg aac cag ctg          48
Met Pro His Asn Ser Ile Arg Ser Gly His Gly Gly Leu Asn Gln Leu
 1               5                  10                  15 gga ggg gcc ttt gtg aat ggc aga cct ctg ccg gaa gtg gtc cgc cag          96
Gly Gly Ala Phe Val Asn Gly Arg Pro Leu Pro Glu Val Val Arg Gln
             20                  25                  30 cgc atc gta gac ctg gcc cac cag ggt gta agg ccc tgc gac atc tct         144
Arg Ile Val Asp Leu Ala His Gln Gly Val Arg Pro Cys Asp Ile Ser
         35                  40                  45 cgc cag ctc cgc gtc agc cat ggc tgc gtc agc aag atc ctt ggc agg         192
Arg Gln Leu Arg Val Ser His Gly Cys Val Ser Lys Ile Leu Gly Arg
     50                  55                  60 tac tac gag act ggc agc atc cgg cct gga gtg ata ggg ggc tcc aag         240
Tyr Tyr Glu Thr Gly Ser Ile Arg Pro Gly Val Ile Gly Gly Ser Lys
 65                  70                  75                  80 ccc aag gtg gcc acc ccc aag gtg gtg gag aag att ggg gac tac aaa         288
Pro Lys Val Ala Thr Pro Lys Val Val Glu Lys Ile Gly Asp Tyr Lys
                 85                  90                  95 cgc cag aac cct acc atg ttt gcc tgg gag atc cga gac cgg ctc ctg         336
Arg Gln Asn Pro Thr Met Phe Ala Trp Glu Ile Arg Asp Arg Leu Leu
            100                 105                 110 gct gag ggc gtc tgt gac aat gac act gtg ccc agt gtc agc tcc att         384
Ala Glu Gly Val Cys Asp Asn Asp Thr Val Pro Ser Val Ser Ser Ile
        115                 120                 125 aat aga atc atc cgg acc aaa gtg cag caa cca ttc aac ctc cct atg         432
Asn Arg Ile Ile Arg Thr Lys Val Gln Gln Pro Phe Asn Leu Pro Met
    130                 135                 140 gac agc tgc gtg gcc acc aag tcc ctg agt ccc gga cac acg ctg atc         480
Asp Ser Cys Val Ala Thr Lys Ser Leu Ser Pro Gly His Thr Leu Ile
145                 150                 155                 160 ccc agc tca gct gta act ccc ccg gag tca ccc cag tcg gat tcc ctg         528
Pro Ser Ser Ala Val Thr Pro Pro Glu Ser Pro Gln Ser Asp Ser Leu
                165                 170                 175 ggc tcc acc tac tcc atc aat ggg ctc ctg ggc atc gct cag cct ggc         576
Gly Ser Thr Tyr Ser Ile Asn Gly Leu Leu Gly Ile Ala Gln Pro Gly
            180                 185                 190 agc gac aag agg aaa atg gat gac agt gat cag gat agc tgc cga cta         624
Ser Asp Lys Arg Lys Met Asp Asp Ser Asp Gln Asp Ser Cys Arg Leu
        195                 200                 205 agc att gac tca cag agc agc agc agc gga ccc cga aag cac ctt cgc         672
Ser Ile Asp Ser Gln Ser Ser Ser Ser Gly Pro Arg Lys His Leu Arg
    210                 215                 220 acg gat gcc ttc agc cag cac cac ctc gag ccg ctc gag tgc cca ttt         720
```

```
                                                                    -continued Thr Asp Ala Phe Ser Gln His His Leu Glu Pro Leu Glu Cys Pro Phe
225                 230                 235                 240 gag cgg cag cac tac cca gag gcc tat gcc tcc ccc agc cac acc aaa        768
Glu Arg Gln His Tyr Pro Glu Ala Tyr Ala Ser Pro Ser His Thr Lys
                    245                 250                 255 ggc gag cag ggc ctc tac ccg ctg ccc ttg ctc aac agc acc ctg gac        816
Gly Glu Gln Gly Leu Tyr Pro Leu Pro Leu Leu Asn Ser Thr Leu Asp
                260                 265                 270 gac ggg aag gcc acc ctg acc cct tcc aac acg cca ctg ggg cgc aac        864
Asp Gly Lys Ala Thr Leu Thr Pro Ser Asn Thr Pro Leu Gly Arg Asn
            275                 280                 285 ctc tcg act cac cag acc tac ccc gtg gtg gca gat cct cac tca ccc        912
Leu Ser Thr His Gln Thr Tyr Pro Val Val Ala Asp Pro His Ser Pro
        290                 295                 300 ttg gcc ata aag cag gaa acc ccc gag gtg tcc agt tct agc tcc acc        960
Leu Ala Ile Lys Gln Glu Thr Pro Glu Val Ser Ser Ser Ser Ser Thr
305                 310                 315                 320 cct tgc tct tta tct agc tcc gcc ctt ttg gat ctg cag caa gtc ggc       1008
Pro Cys Ser Leu Ser Ser Ser Ala Leu Leu Asp Leu Gln Gln Val Gly
                    325                 330                 335 tcc ggg gtc ccg ccc ttc aat gcc ttt ccc cat gct gcc tcc gtg tac       1056
Ser Gly Val Pro Pro Phe Asn Ala Phe Pro His Ala Ala Ser Val Tyr
                340                 345                 350 ggg cag ttc acg ggc cag gcc ctc ctc tca ggg cga gag atg gtg ggg       1104
Gly Gln Phe Thr Gly Gln Ala Leu Leu Ser Gly Arg Glu Met Val Gly
            355                 360                 365 ccc acg ctg ccc gga tac cca ccc cac atc ccc acc agc gga cag ggc       1152
Pro Thr Leu Pro Gly Tyr Pro Pro His Ile Pro Thr Ser Gly Gln Gly
        370                 375                 380 agc tat gcc tcc tct gcc atc gca ggc atg gtg gca gaa atg acc atg       1200
Ser Tyr Ala Ser Ser Ala Ile Ala Gly Met Val Ala Glu Met Thr Met
385                 390                 395                 400 gtt gac aca gag atg cca ttc tgg ccc acc aac ttt ggg atc agc tcc       1248
Val Asp Thr Glu Met Pro Phe Trp Pro Thr Asn Phe Gly Ile Ser Ser
                    405                 410                 415 gtg gat ctc tcc gta atg gaa gac cac tcc cac tcc ttt gat atc aag       1296
Val Asp Leu Ser Val Met Glu Asp His Ser His Ser Phe Asp Ile Lys
                420                 425                 430 ccc ttc act act gtt gac ttc tcc agc att tct act cca cat tac gaa       1344
Pro Phe Thr Thr Val Asp Phe Ser Ser Ile Ser Thr Pro His Tyr Glu
            435                 440                 445 gac att cca ttc aca aga aca gat cca gtg gtt gca gat tac aag tat       1392
Asp Ile Pro Phe Thr Arg Thr Asp Pro Val Val Ala Asp Tyr Lys Tyr
        450                 455                 460 gac ctg aaa ctt caa gag tac caa agt gca atc aaa gtg gag cct gca       1440
Asp Leu Lys Leu Gln Glu Tyr Gln Ser Ala Ile Lys Val Glu Pro Ala
465                 470                 475                 480 tct cca cct tat tat tct gag aag act cag ctc tac aat aag cct cat       1488
Ser Pro Pro Tyr Tyr Ser Glu Lys Thr Gln Leu Tyr Asn Lys Pro His
                    485                 490                 495 gaa gag cct tcc aac tcc ctc atg gca att gaa tgt cgt gtc tgt gga       1536
Glu Glu Pro Ser Asn Ser Leu Met Ala Ile Glu Cys Arg Val Cys Gly
                500                 505                 510 gat aaa gct tct gga ttt cac tat gga gtt cat gct tgt gaa gga tgc       1584
Asp Lys Ala Ser Gly Phe His Tyr Gly Val His Ala Cys Glu Gly Cys
            515                 520                 525 aag ggt ttc ttc cgg aga aca atc aga ttg aag ctt atc tat gac aga       1632
Lys Gly Phe Phe Arg Arg Thr Ile Arg Leu Lys Leu Ile Tyr Asp Arg
        530                 535                 540
```

-continued

| | | |
|---|---|---|
| tgt gat ctt aac tgt cgg atc cac aaa aaa agt aga aat aaa tgt cag<br>Cys Asp Leu Asn Cys Arg Ile His Lys Lys Ser Arg Asn Lys Cys Gln<br>545                                550                            555                            560 | | 1680 |
| tac tgt cgg ttt cag aaa tgc ctt gca gtg ggg atg tct cat aat gcc<br>Tyr Cys Arg Phe Gln Lys Cys Leu Ala Val Gly Met Ser His Asn Ala<br>                          565                            570                            575 | | 1728 |
| atc agg ttt ggg cgg atg cca cag gcc gag aag gag aag ctg ttg gcg<br>Ile Arg Phe Gly Arg Met Pro Gln Ala Glu Lys Glu Lys Leu Leu Ala<br>                580                            585                            590 | | 1776 |
| gag atc tcc agt gat atc gac cag ctg aat cca gag tcc gct gac ctc<br>Glu Ile Ser Ser Asp Ile Asp Gln Leu Asn Pro Glu Ser Ala Asp Leu<br>               595                            600                          605 | | 1824 |
| cgg gcc ctg gca aaa cat ttg tat gac tca tac ata aag tcc ttc ccg<br>Arg Ala Leu Ala Lys His Leu Tyr Asp Ser Tyr Ile Lys Ser Phe Pro<br>610                                615                            620 | | 1872 |
| ctg acc aaa gca aag gcg agg gcg atc ttg aca gga aag aca aca gac<br>Leu Thr Lys Ala Lys Ala Arg Ala Ile Leu Thr Gly Lys Thr Thr Asp<br>625                                630                            635                          640 | | 1920 |
| aaa tca cca ttc gtt atc tat gac atg aat tcc tta atg atg gga gaa<br>Lys Ser Pro Phe Val Ile Tyr Asp Met Asn Ser Leu Met Met Gly Glu<br>                          645                            650                            655 | | 1968 |
| gat aaa atc aag ttc aaa cac atc acc ccc ctg cag gag cag agc aaa<br>Asp Lys Ile Lys Phe Lys His Ile Thr Pro Leu Gln Glu Gln Ser Lys<br>                660                            665                            670 | | 2016 |
| gag gtg gcc atc cgc atc ttt cag ggc tgc cag ttt cgc tcc gtg gag<br>Glu Val Ala Ile Arg Ile Phe Gln Gly Cys Gln Phe Arg Ser Val Glu<br>675                                680                            685 | | 2064 |
| gct gtg cag gag atc aca gag tat gcc aaa agc att cct ggt ttt gta<br>Ala Val Gln Glu Ile Thr Glu Tyr Ala Lys Ser Ile Pro Gly Phe Val<br>               690                            695                          700 | | 2112 |
| aat ctt gac ttg aac gac caa gta act ctc ctc aaa tat gga gtc cac<br>Asn Leu Asp Leu Asn Asp Gln Val Thr Leu Leu Lys Tyr Gly Val His<br>705                                710                            715                          720 | | 2160 |
| gag atc att tac aca atg ctg gcc tcc ttg atg aat aaa gat ggg gtt<br>Glu Ile Ile Tyr Thr Met Leu Ala Ser Leu Met Asn Lys Asp Gly Val<br>                          725                            730                            735 | | 2208 |
| ctc ata tcc gag ggc caa ggc ttc atg aca agg gag ttt cta aag agc<br>Leu Ile Ser Glu Gly Gln Gly Phe Met Thr Arg Glu Phe Leu Lys Ser<br>               740                            745                          750 | | 2256 |
| ctg cga aag cct ttt ggt gac ttt atg gag ccc aag ttt gag ttt gct<br>Leu Arg Lys Pro Phe Gly Asp Phe Met Glu Pro Lys Phe Glu Phe Ala<br>                          755                            760                          765 | | 2304 |
| gtg aag ttc aat gca ctg gaa tta gat gac agc gac ttg gca ata ttt<br>Val Lys Phe Asn Ala Leu Glu Leu Asp Asp Ser Asp Leu Ala Ile Phe<br>770                                775                            780 | | 2352 |
| att gct gtc att att ctc agt gga gac cgc cca ggt ttg ctg aat gtg<br>Ile Ala Val Ile Ile Leu Ser Gly Asp Arg Pro Gly Leu Leu Asn Val<br>785                                790                            795                          800 | | 2400 |
| aag ccc att gaa gac att caa gac aac ctg cta caa gcc ctg gag ctc<br>Lys Pro Ile Glu Asp Ile Gln Asp Asn Leu Leu Gln Ala Leu Glu Leu<br>                          805                            810                            815 | | 2448 |
| cag ctg aag ctg aac cac cct gag tcc tca cag ctg ttt gcc aag ctg<br>Gln Leu Lys Leu Asn His Pro Glu Ser Ser Gln Leu Phe Ala Lys Leu<br>               820                            825                          830 | | 2496 |
| ctc cag aaa atg aca gac ctc aga cag att gtc acg gaa cac gtg cag<br>Leu Gln Lys Met Thr Asp Leu Arg Gln Ile Val Thr Glu His Val Gln<br>835                                840                            845 | | 2544 |
| cta ctg cag gtg atc aag aag acg gag aca gac atg agt ctt cac ccg<br>Leu Leu Gln Val Ile Lys Lys Thr Glu Thr Asp Met Ser Leu His Pro<br>               850                            855                          860 | | 2592 |

```
ctc ctg cag gag atc tac aag gac ttg tac tag                          2625
Leu Leu Gln Glu Ile Tyr Lys Asp Leu Tyr  *
865                 870
```

<210> SEQ ID NO 6
<211> LENGTH: 874
<212> TYPE: PRT
<213> ORGANISM: Homo Sapiens

<400> SEQUENCE: 6

```
Met Pro His Asn Ser Ile Arg Ser Gly His Gly Gly Leu Asn Gln Leu
 1               5                  10                  15

Gly Gly Ala Phe Val Asn Gly Arg Pro Leu Pro Glu Val Val Arg Gln
             20                  25                  30

Arg Ile Val Asp Leu Ala His Gln Gly Val Arg Pro Cys Asp Ile Ser
         35                  40                  45

Arg Gln Leu Arg Val Ser His Gly Cys Val Ser Lys Ile Leu Gly Arg
     50                  55                  60

Tyr Tyr Glu Thr Gly Ser Ile Arg Pro Gly Val Ile Gly Gly Ser Lys
 65                  70                  75                  80

Pro Lys Val Ala Thr Pro Lys Val Val Glu Lys Ile Gly Asp Tyr Lys
                 85                  90                  95

Arg Gln Asn Pro Thr Met Phe Ala Trp Glu Ile Arg Asp Arg Leu Leu
            100                 105                 110

Ala Glu Gly Val Cys Asp Asn Asp Thr Val Pro Ser Val Ser Ser Ile
        115                 120                 125

Asn Arg Ile Ile Arg Thr Lys Val Gln Gln Pro Phe Asn Leu Pro Met
    130                 135                 140

Asp Ser Cys Val Ala Thr Lys Ser Leu Ser Pro Gly His Thr Leu Ile
145                 150                 155                 160

Pro Ser Ser Ala Val Thr Pro Pro Glu Ser Pro Gln Ser Asp Ser Leu
                165                 170                 175

Gly Ser Thr Tyr Ser Ile Asn Gly Leu Leu Gly Ile Ala Gln Pro Gly
            180                 185                 190

Ser Asp Lys Arg Lys Met Asp Asp Ser Asp Gln Asp Ser Cys Arg Leu
        195                 200                 205

Ser Ile Asp Ser Gln Ser Ser Ser Gly Pro Arg Lys His Leu Arg
    210                 215                 220

Thr Asp Ala Phe Ser Gln His His Leu Glu Pro Leu Glu Cys Pro Phe
225                 230                 235                 240

Glu Arg Gln His Tyr Pro Glu Ala Tyr Ala Ser Pro Ser His Thr Lys
                245                 250                 255

Gly Glu Gln Gly Leu Tyr Pro Leu Pro Leu Leu Asn Ser Thr Leu Asp
            260                 265                 270

Asp Gly Lys Ala Thr Leu Thr Pro Ser Asn Thr Pro Leu Gly Arg Asn
        275                 280                 285

Leu Ser Thr His Gln Thr Tyr Pro Val Val Ala Asp Pro His Ser Pro
    290                 295                 300

Leu Ala Ile Lys Gln Glu Thr Pro Glu Val Ser Ser Ser Ser Ser Thr
305                 310                 315                 320

Pro Cys Ser Leu Ser Ser Ser Ala Leu Leu Asp Leu Gln Gln Val Gly
                325                 330                 335

Ser Gly Val Pro Pro Phe Asn Ala Phe Pro His Ala Ala Ser Val Tyr
            340                 345                 350
```

-continued

```
Gly Gln Phe Thr Gly Gln Ala Leu Leu Ser Gly Arg Glu Met Val Gly
        355                 360                 365

Pro Thr Leu Pro Gly Tyr Pro Pro His Ile Pro Thr Ser Gly Gln Gly
    370                 375                 380

Ser Tyr Ala Ser Ser Ala Ile Ala Gly Met Val Ala Glu Met Thr Met
385                 390                 395                 400

Val Asp Thr Glu Met Pro Phe Trp Pro Thr Asn Phe Gly Ile Ser Ser
                405                 410                 415

Val Asp Leu Ser Val Met Glu Asp His Ser His Ser Phe Asp Ile Lys
            420                 425                 430

Pro Phe Thr Thr Val Asp Phe Ser Ile Ser Thr Pro His Tyr Glu
            435                 440                 445

Asp Ile Pro Phe Thr Arg Thr Asp Pro Val Val Ala Asp Tyr Lys Tyr
    450                 455                 460

Asp Leu Lys Leu Gln Glu Tyr Gln Ser Ala Ile Lys Val Glu Pro Ala
465                 470                 475                 480

Ser Pro Pro Tyr Tyr Ser Glu Lys Thr Gln Leu Tyr Asn Lys Pro His
                485                 490                 495

Glu Glu Pro Ser Asn Ser Leu Met Ala Ile Glu Cys Arg Val Cys Gly
            500                 505                 510

Asp Lys Ala Ser Gly Phe His Tyr Gly Val His Ala Cys Glu Gly Cys
            515                 520                 525

Lys Gly Phe Phe Arg Arg Thr Ile Arg Leu Lys Leu Ile Tyr Asp Arg
    530                 535                 540

Cys Asp Leu Asn Cys Arg Ile His Lys Lys Ser Arg Asn Lys Cys Gln
545                 550                 555                 560

Tyr Cys Arg Phe Gln Lys Cys Leu Ala Val Gly Met Ser His Asn Ala
                565                 570                 575

Ile Arg Phe Gly Arg Met Pro Gln Ala Glu Lys Glu Lys Leu Leu Ala
            580                 585                 590

Glu Ile Ser Ser Asp Ile Asp Gln Leu Asn Pro Glu Ser Ala Asp Leu
            595                 600                 605

Arg Ala Leu Ala Lys His Leu Tyr Asp Ser Tyr Ile Lys Ser Phe Pro
    610                 615                 620

Leu Thr Lys Ala Lys Ala Arg Ala Ile Leu Thr Gly Lys Thr Thr Asp
625                 630                 635                 640

Lys Ser Pro Phe Val Ile Tyr Asp Met Asn Ser Leu Met Met Gly Glu
                645                 650                 655

Asp Lys Ile Lys Phe Lys His Ile Thr Pro Leu Gln Glu Gln Ser Lys
            660                 665                 670

Glu Val Ala Ile Arg Ile Phe Gln Gly Cys Gln Phe Arg Ser Val Glu
            675                 680                 685

Ala Val Gln Glu Ile Thr Glu Tyr Ala Lys Ser Ile Pro Gly Phe Val
    690                 695                 700

Asn Leu Asp Leu Asn Asp Gln Val Thr Leu Leu Lys Tyr Gly Val His
705                 710                 715                 720

Glu Ile Ile Tyr Thr Met Leu Ala Ser Leu Met Asn Lys Asp Gly Val
                725                 730                 735

Leu Ile Ser Glu Gly Gln Gly Phe Met Thr Arg Glu Phe Leu Lys Ser
            740                 745                 750

Leu Arg Lys Pro Phe Gly Asp Phe Met Glu Pro Lys Phe Glu Phe Ala
    755                 760                 765

Val Lys Phe Asn Ala Leu Glu Leu Asp Asp Ser Asp Leu Ala Ile Phe
```

```
                     770               775               780
Ile Ala Val Ile Ile Leu Ser Gly Asp Arg Pro Gly Leu Leu Asn Val
785                 790               795               800

Lys Pro Ile Glu Asp Ile Gln Asp Asn Leu Leu Gln Ala Leu Glu Leu
                805               810               815

Gln Leu Lys Leu Asn His Pro Glu Ser Ser Gln Leu Phe Ala Lys Leu
                820               825               830

Leu Gln Lys Met Thr Asp Leu Arg Gln Ile Val Thr Glu His Val Gln
                835               840               845

Leu Leu Gln Val Ile Lys Lys Thr Glu Thr Asp Met Ser Leu His Pro
    850               855               860

Leu Leu Gln Glu Ile Tyr Lys Asp Leu Tyr
865             870
```

```
<210> SEQ ID NO 7
<211> LENGTH: 42
<212> TYPE: DNA
<213> ORGANISM: Homo Sapiens
<220> FEATURE:
<221> NAME/KEY: CDS
<222> LOCATION: (3)...(41)

<400> SEQUENCE: 7 ag acc tac ccc gtg gtg gca gaa atg acc atg gtt gac aca g         42
   Thr Tyr Pro Val Val Ala Glu Met Thr Met Val Asp Thr
   1               5                   10
```

```
<210> SEQ ID NO 8
<211> LENGTH: 13
<212> TYPE: PRT
<213> ORGANISM: Homo Sapiens

<400> SEQUENCE: 8

Thr Tyr Pro Val Val Ala Glu Met Thr Met Val Asp Thr
1               5                   10
```

```
<210> SEQ ID NO 9
<211> LENGTH: 42
<212> TYPE: DNA
<213> ORGANISM: Homo Sapiens
<220> FEATURE:
<221> NAME/KEY: CDS
<222> LOCATION: (3)...(41)

<400> SEQUENCE: 9 cg ggc cag gcc ctc ctc tca gaa atg acc atg gtt gac aca g         42
   Gly Gln Ala Leu Leu Ser Glu Met Thr Met Val Asp Thr
   1               5                   10
```

```
<210> SEQ ID NO 10
<211> LENGTH: 13
<212> TYPE: PRT
<213> ORGANISM: Homo Sapiens

<400> SEQUENCE: 10

Gly Gln Ala Leu Leu Ser Glu Met Thr Met Val Asp Thr
1               5                   10
```

```
<210> SEQ ID NO 11
<211> LENGTH: 42
<212> TYPE: DNA
<213> ORGANISM: Homo Sapiens
<220> FEATURE:
<221> NAME/KEY: CDS
```

<222> LOCATION: (3)...(41)

<400> SEQUENCE: 11

```
cc atc gca ggc atg gtg gca gaa atg acc atg gtt gac aca g          42
   Ile Ala Gly Met Val Ala Glu Met Thr Met Val Asp Thr
   1               5                   10
```

<210> SEQ ID NO 12
<211> LENGTH: 13
<212> TYPE: PRT
<213> ORGANISM: Homo Sapiens

<400> SEQUENCE: 12

```
Ile Ala Gly Met Val Ala Glu Met Thr Met Val Asp Thr
1               5                   10
```

<210> SEQ ID NO 13
<211> LENGTH: 1372
<212> TYPE: DNA
<213> ORGANISM: Homo Sapiens
<220> FEATURE:
<221> NAME/KEY: CDS
<222> LOCATION: (11)...(1363)

<400> SEQUENCE: 13

```
gaattcggcg atg cct cac aac tcc atc aga tct ggc cat gga ggg ctg     49
           Met Pro His Asn Ser Ile Arg Ser Gly His Gly Gly Leu
           1               5                   10 aac cag ctg gga ggg gcc ttt gtg aat ggc aga cct ctg ccg gaa gtg    97
Asn Gln Leu Gly Gly Ala Phe Val Asn Gly Arg Pro Leu Pro Glu Val
15                  20                  25 gtc cgc cag cgc atc gta gac ctg gcc cac cag ggt gta agg ccc tgc   145
Val Arg Gln Arg Ile Val Asp Leu Ala His Gln Gly Val Arg Pro Cys
30                  35                  40                  45 gac atc tct cgc cag ctc cgc gtc agc cat ggt tgc gtc agc aag atc   193
Asp Ile Ser Arg Gln Leu Arg Val Ser His Gly Cys Val Ser Lys Ile
                50                  55                  60 ctt ggc agg tac tac gag act ggc agc atc cgg cct gga gtg ata ggg   241
Leu Gly Arg Tyr Tyr Glu Thr Gly Ser Ile Arg Pro Gly Val Ile Gly
            65                  70                  75 ggc tcc aag ccc aag gtg gcc acc ccc aag gtg gtg gag aag att ggg   289
Gly Ser Lys Pro Lys Val Ala Thr Pro Lys Val Val Glu Lys Ile Gly
        80                  85                  90 gac tac aaa cgc cag aac cct acc atg ttt gcc tgg gag atc cga gac   337
Asp Tyr Lys Arg Gln Asn Pro Thr Met Phe Ala Trp Glu Ile Arg Asp
    95                  100                 105 cgg ctc ctg gct gag ggc gtc tgt gac aat gac act gtg ccc agt gtc   385
Arg Leu Leu Ala Glu Gly Val Cys Asp Asn Asp Thr Val Pro Ser Val
110                 115                 120                 125 agc tcc att aat aga atc atc cgg acc aaa gtg cag caa cca ttc aac   433
Ser Ser Ile Asn Arg Ile Ile Arg Thr Lys Val Gln Gln Pro Phe Asn
                130                 135                 140 ctc cct atg gac agc tgc gtg gcc acc aag tcc ctg agt ccc gga cac   481
Leu Pro Met Asp Ser Cys Val Ala Thr Lys Ser Leu Ser Pro Gly His
            145                 150                 155 acg ctg atc ccc agc tca gct gta act ccc ccg gag tca ccc cag tcg   529
Thr Leu Ile Pro Ser Ser Ala Val Thr Pro Pro Glu Ser Pro Gln Ser
        160                 165                 170 gat tcc ctg ggc tcc acc tac tcc atc aat ggg ctc ctg ggc atc gct   577
Asp Ser Leu Gly Ser Thr Tyr Ser Ile Asn Gly Leu Leu Gly Ile Ala
    175                 180                 185 cag cct ggc agc gac aag agg aaa atg gat gac agt gat cag gat agc   625
```

```
Gln Pro Gly Ser Asp Lys Arg Lys Met Asp Asp Ser Asp Gln Asp Ser
190                 195                 200                 205 tgc cga cta agc att gac tca cag agc agc agc gga ccc cga aag         673
Cys Arg Leu Ser Ile Asp Ser Gln Ser Ser Ser Gly Pro Arg Lys
                210                 215                 220 cac ctt cgc acg gat gcc ttc agc cag cac cac ctc gag ccg ctc gag     721
His Leu Arg Thr Asp Ala Phe Ser Gln His His Leu Glu Pro Leu Glu
            225                 230                 235 tgc cca ttt gag cgg cag cac tac cca gag gcc tat gcc tcc ccc agc     769
Cys Pro Phe Glu Arg Gln His Tyr Pro Glu Ala Tyr Ala Ser Pro Ser
        240                 245                 250 cac acc aaa ggc gag cag ggc ctc tac ccg ctg ccc ttg ctc aac agc     817
His Thr Lys Gly Glu Gln Gly Leu Tyr Pro Leu Pro Leu Leu Asn Ser
    255                 260                 265 acc ctg gac gac ggg aag gcc acc ctg acc cct tcc aac acg cca ctg     865
Thr Leu Asp Asp Gly Lys Ala Thr Leu Thr Pro Ser Asn Thr Pro Leu
270                 275                 280                 285 ggg cgc aac ctc tcg act cac cag acc tac ccc gtg gtg gca gat cct     913
Gly Arg Asn Leu Ser Thr His Gln Thr Tyr Pro Val Val Ala Asp Pro
                290                 295                 300 cac tca ccc ttc gcc ata aag cag gaa acc ccc gag gtg tcc agt tct     961
His Ser Pro Phe Ala Ile Lys Gln Glu Thr Pro Glu Val Ser Ser Ser
            305                 310                 315 agc tcc acc cct tcc tct tta tct agc tcc gcc ttt ttg gat ctg cag     1009
Ser Ser Thr Pro Ser Ser Leu Ser Ser Ser Ala Phe Leu Asp Leu Gln
        320                 325                 330 caa gtc ggc tcc ggg gtc ccg ccc ttc aat gcc ttt ccc cat gct gcc     1057
Gln Val Gly Ser Gly Val Pro Pro Phe Asn Ala Phe Pro His Ala Ala
    335                 340                 345 tcc gtg tac ggg cag ttc acg ggc cag gcc ctc ctc tca ggg cga gag     1105
Ser Val Tyr Gly Gln Phe Thr Gly Gln Ala Leu Leu Ser Gly Arg Glu
350                 355                 360                 365 atg gtg ggg ccc acg ctg ccc gga tac cca ccc cac atc ccc acc agc     1153
Met Val Gly Pro Thr Leu Pro Gly Tyr Pro Pro His Ile Pro Thr Ser
                370                 375                 380 gga cag ggc agc tat gcc tcc tct gcc atc gca ggc atg gtg gca gga     1201
Gly Gln Gly Ser Tyr Ala Ser Ser Ala Ile Ala Gly Met Val Ala Gly
            385                 390                 395 agt gaa tac tct ggc aat gcc tat ggc cac acc ccc tac tcc tcc tac     1249
Ser Glu Tyr Ser Gly Asn Ala Tyr Gly His Thr Pro Tyr Ser Ser Tyr
        400                 405                 410 agc gag gcc tgg cgc ttc ccc aac tcc agc ttg ctg agt tcc cca tat     1297
Ser Glu Ala Trp Arg Phe Pro Asn Ser Ser Leu Leu Ser Ser Pro Tyr
    415                 420                 425 tat tac agt tcc aca tca agg ccg agt gca ccg ccc acc act gcc acg     1345
Tyr Tyr Ser Ser Thr Ser Arg Pro Ser Ala Pro Pro Thr Thr Ala Thr
430                 435                 440                 445 gcc ttt gac cat ctg tag ttgaagctt                                   1372
Ala Phe Asp His Leu *
                450

<210> SEQ ID NO 14
<211> LENGTH: 450
<212> TYPE: PRT
<213> ORGANISM: Homo Sapiens

<400> SEQUENCE: 14

Met Pro His Asn Ser Ile Arg Ser Gly His Gly Gly Leu Asn Gln Leu
1               5                   10                  15

Gly Gly Ala Phe Val Asn Gly Arg Pro Leu Pro Glu Val Val Arg Gln
```

-continued

```
                 20                  25                  30
Arg Ile Val Asp Leu Ala His Gln Gly Val Arg Pro Cys Asp Ile Ser
             35                  40                  45
Arg Gln Leu Arg Val Ser His Gly Cys Val Ser Lys Ile Leu Gly Arg
 50                  55                  60
Tyr Tyr Glu Thr Gly Ser Ile Arg Pro Gly Val Ile Gly Gly Ser Lys
 65                  70                  75                  80
Pro Lys Val Ala Thr Pro Lys Val Glu Lys Ile Gly Asp Tyr Lys
                 85                  90                  95
Arg Gln Asn Pro Thr Met Phe Ala Trp Glu Ile Arg Asp Arg Leu Leu
                100                 105                 110
Ala Glu Gly Val Cys Asp Asn Asp Thr Val Pro Ser Val Ser Ser Ile
            115                 120                 125
Asn Arg Ile Ile Arg Thr Lys Val Gln Gln Pro Phe Asn Leu Pro Met
130                 135                 140
Asp Ser Cys Val Ala Thr Lys Ser Leu Ser Pro Gly His Thr Leu Ile
145                 150                 155                 160
Pro Ser Ser Ala Val Thr Pro Pro Glu Ser Pro Gln Ser Asp Ser Leu
                165                 170                 175
Gly Ser Thr Tyr Ser Ile Asn Gly Leu Leu Gly Ile Ala Gln Pro Gly
            180                 185                 190
Ser Asp Lys Arg Lys Met Asp Asp Ser Asp Gln Asp Ser Cys Arg Leu
            195                 200                 205
Ser Ile Asp Ser Gln Ser Ser Ser Gly Pro Arg Lys His Leu Arg
    210                 215                 220
Thr Asp Ala Phe Ser Gln His His Leu Glu Pro Leu Glu Cys Pro Phe
225                 230                 235                 240
Glu Arg Gln His Tyr Pro Glu Ala Tyr Ala Ser Pro Ser His Thr Lys
                245                 250                 255
Gly Glu Gln Gly Leu Tyr Pro Leu Pro Leu Leu Asn Ser Thr Leu Asp
            260                 265                 270
Asp Gly Lys Ala Thr Leu Thr Pro Ser Asn Thr Pro Leu Gly Arg Asn
            275                 280                 285
Leu Ser Thr His Gln Thr Tyr Pro Val Val Ala Asp Pro His Ser Pro
    290                 295                 300
Phe Ala Ile Lys Gln Glu Thr Pro Glu Val Ser Ser Ser Ser Thr
305                 310                 315                 320
Pro Ser Ser Leu Ser Ser Ser Ala Phe Leu Asp Leu Gln Gln Val Gly
                325                 330                 335
Ser Gly Val Pro Pro Phe Asn Ala Phe Pro His Ala Ala Ser Val Tyr
            340                 345                 350
Gly Gln Phe Thr Gly Gln Ala Leu Leu Ser Gly Arg Glu Met Val Gly
            355                 360                 365
Pro Thr Leu Pro Gly Tyr Pro Pro His Ile Pro Thr Ser Gly Gln Gly
    370                 375                 380
Ser Tyr Ala Ser Ser Ala Ile Ala Gly Met Val Ala Gly Ser Glu Tyr
385                 390                 395                 400
Ser Gly Asn Ala Tyr Gly His Thr Pro Tyr Ser Ser Tyr Ser Glu Ala
                405                 410                 415
Trp Arg Phe Pro Asn Ser Ser Leu Leu Ser Ser Pro Tyr Tyr Tyr Ser
            420                 425                 430
Ser Thr Ser Arg Pro Ser Ala Pro Pro Thr Thr Ala Thr Ala Phe Asp
            435                 440                 445
```

His Leu
   450

<210> SEQ ID NO 15
<211> LENGTH: 1608
<212> TYPE: DNA
<213> ORGANISM: Homo Sapiens
<220> FEATURE:
<221> NAME/KEY: CDS
<222> LOCATION: (91)...(1608)

<400> SEQUENCE: 15

```
tccggttttt ttctttaac ggattgatct tttgctagat agagacaaaa tatcagtgtg        60
aattacagca aaccctatt ccatgctgtt atg ggt gaa act ctg gga gat tct       114
                                  Met Gly Glu Thr Leu Gly Asp Ser
                                    1               5 cct att gac cca gaa agc gat tcc ttc act gat aca ctg tct gca aac       162
Pro Ile Asp Pro Glu Ser Asp Ser Phe Thr Asp Thr Leu Ser Ala Asn
 10                  15                  20 ata tca caa gaa atg acc atg gtt gac aca gag atg cca ttc tgg ccc       210
Ile Ser Gln Glu Met Thr Met Val Asp Thr Glu Met Pro Phe Trp Pro
 25                  30                  35                  40 acc aac ttt ggg atc agc tcc gtg gat ctc tcc gta atg gaa gac cac       258
Thr Asn Phe Gly Ile Ser Ser Val Asp Leu Ser Val Met Glu Asp His
                 45                  50                  55 tcc cac tcc ttt gat atc aag ccc ttc act act gtt gac ttc tcc agc       306
Ser His Ser Phe Asp Ile Lys Pro Phe Thr Thr Val Asp Phe Ser Ser
             60                  65                  70 att tct act cca cat tac gaa gac att cca ttc aca aga aca gat cca       354
Ile Ser Thr Pro His Tyr Glu Asp Ile Pro Phe Thr Arg Thr Asp Pro
         75                  80                  85 gtg gtt gca gat tac aag tat gac ctg aaa ctt caa gag tac caa agt       402
Val Val Ala Asp Tyr Lys Tyr Asp Leu Lys Leu Gln Glu Tyr Gln Ser
     90                  95                 100 gca atc aaa gtg gag cct gca tct cca cct tat tat tct gag aag act       450
Ala Ile Lys Val Glu Pro Ala Ser Pro Pro Tyr Tyr Ser Glu Lys Thr
105                 110                 115                 120 cag ctc tac aat aag cct cat gaa gag cct tcc aac tcc ctc atg gca       498
Gln Leu Tyr Asn Lys Pro His Glu Glu Pro Ser Asn Ser Leu Met Ala
                125                 130                 135 att gaa tgt cgt gtc tgt gga gat aaa gct tct gga ttt cac tat gga       546
Ile Glu Cys Arg Val Cys Gly Asp Lys Ala Ser Gly Phe His Tyr Gly
            140                 145                 150 gtt cat gct tgt gaa gga tgc aag ggt ttc ttc cgg aga aca atc aga       594
Val His Ala Cys Glu Gly Cys Lys Gly Phe Phe Arg Arg Thr Ile Arg
        155                 160                 165 ttg aag ctt atc tat gac aga tgt gat ctt aac tgt cgg atc cac aaa       642
Leu Lys Leu Ile Tyr Asp Arg Cys Asp Leu Asn Cys Arg Ile His Lys
    170                 175                 180 aaa agt aga aat aaa tgt cag tac tgt cgg ttt cag aaa tgc ctt gca       690
Lys Ser Arg Asn Lys Cys Gln Tyr Cys Arg Phe Gln Lys Cys Leu Ala
185                 190                 195                 200 gtg ggg atg tct cat aat gcc atc agg ttt ggg cgg atg cca cag gcc       738
Val Gly Met Ser His Asn Ala Ile Arg Phe Gly Arg Met Pro Gln Ala
                205                 210                 215 gag aag gag aag ctg ttg gcg gag atc tcc agt gat atc gac cag ctg       786
Glu Lys Glu Lys Leu Leu Ala Glu Ile Ser Ser Asp Ile Asp Gln Leu
            220                 225                 230 aat cca gag tcc gct gac ctc cgg gcc ctg gca aaa cat ttg tat gac       834
Asn Pro Glu Ser Ala Asp Leu Arg Ala Leu Ala Lys His Leu Tyr Asp
```

-continued

| | | | | | | | | | | | | | | | | |
|---|---|---|---|---|---|---|---|---|---|---|---|---|---|---|---|---|
| | | | | | 235 | | | | 240 | | | | | 245 | | |
| tca | tac | ata | aag | tcc | ttc | ccg | ctg | acc | aaa | gca | aag | gcg | agg | gcg | atc | 882 |
| Ser | Tyr | Ile | Lys | Ser | Phe | Pro | Leu | Thr | Lys | Ala | Lys | Ala | Arg | Ala | Ile | |
| | 250 | | | | | 255 | | | | | 260 | | | | | |
| ttg | aca | gga | aag | aca | aca | gac | aaa | tca | cca | ttc | gtt | atc | tat | gac | atg | 930 |
| Leu | Thr | Gly | Lys | Thr | Thr | Asp | Lys | Ser | Pro | Phe | Val | Ile | Tyr | Asp | Met | |
| 265 | | | | | 270 | | | | | 275 | | | | | 280 | |
| aat | tcc | tta | atg | atg | gga | gaa | gat | aaa | atc | aag | ttc | aaa | cac | atc | acc | 978 |
| Asn | Ser | Leu | Met | Met | Gly | Glu | Asp | Lys | Ile | Lys | Phe | Lys | His | Ile | Thr | |
| | | | | 285 | | | | | 290 | | | | | 295 | | |
| ccc | ctg | cag | gag | cag | agc | aaa | gag | gtg | gcc | atc | cgc | atc | ttt | cag | ggc | 1026 |
| Pro | Leu | Gln | Glu | Gln | Ser | Lys | Glu | Val | Ala | Ile | Arg | Ile | Phe | Gln | Gly | |
| | | | 300 | | | | | 305 | | | | | 310 | | | |
| tgc | cag | ttt | cgc | tcc | gtg | gag | gct | gtg | cag | gag | atc | aca | gag | tat | gcc | 1074 |
| Cys | Gln | Phe | Arg | Ser | Val | Glu | Ala | Val | Gln | Glu | Ile | Thr | Glu | Tyr | Ala | |
| | | 315 | | | | | 320 | | | | | 325 | | | | |
| aaa | agc | att | cct | ggt | ttt | gta | aat | ctt | gac | ttg | aac | gac | caa | gta | act | 1122 |
| Lys | Ser | Ile | Pro | Gly | Phe | Val | Asn | Leu | Asp | Leu | Asn | Asp | Gln | Val | Thr | |
| | 330 | | | | | 335 | | | | | 340 | | | | | |
| ctc | ctc | aaa | tat | gga | gtc | cac | gag | atc | att | tac | aca | atg | ctg | gcc | tcc | 1170 |
| Leu | Leu | Lys | Tyr | Gly | Val | His | Glu | Ile | Ile | Tyr | Thr | Met | Leu | Ala | Ser | |
| 345 | | | | | 350 | | | | | 355 | | | | | 360 | |
| ttg | atg | aat | aaa | gat | ggg | gtt | ctc | ata | tcc | gag | ggc | caa | ggc | ttc | atg | 1218 |
| Leu | Met | Asn | Lys | Asp | Gly | Val | Leu | Ile | Ser | Glu | Gly | Gln | Gly | Phe | Met | |
| | | | | 365 | | | | | 370 | | | | | 375 | | |
| aca | agg | gag | ttt | cta | aag | agc | ctg | cga | aag | cct | ttt | ggt | gac | ttt | atg | 1266 |
| Thr | Arg | Glu | Phe | Leu | Lys | Ser | Leu | Arg | Lys | Pro | Phe | Gly | Asp | Phe | Met | |
| | | | 380 | | | | | 385 | | | | | 390 | | | |
| gag | ccc | aag | ttt | gag | ttt | gct | gtg | aag | ttc | aat | gca | ctg | gaa | tta | gat | 1314 |
| Glu | Pro | Lys | Phe | Glu | Phe | Ala | Val | Lys | Phe | Asn | Ala | Leu | Glu | Leu | Asp | |
| | | 395 | | | | | 400 | | | | | 405 | | | | |
| gac | agc | gac | ttg | gca | ata | ttt | att | gct | gtc | att | att | ctc | agt | gga | gac | 1362 |
| Asp | Ser | Asp | Leu | Ala | Ile | Phe | Ile | Ala | Val | Ile | Ile | Leu | Ser | Gly | Asp | |
| | 410 | | | | | 415 | | | | | 420 | | | | | |
| cgc | cca | ggt | ttg | ctg | aat | gtg | aag | ccc | att | gaa | gac | att | caa | gac | aac | 1410 |
| Arg | Pro | Gly | Leu | Leu | Asn | Val | Lys | Pro | Ile | Glu | Asp | Ile | Gln | Asp | Asn | |
| 425 | | | | | 430 | | | | | 435 | | | | | 440 | |
| ctg | cta | caa | gcc | ctg | gag | ctc | cag | ctg | aag | ctg | aac | cac | cct | gag | tcc | 1458 |
| Leu | Leu | Gln | Ala | Leu | Glu | Leu | Gln | Leu | Lys | Leu | Asn | His | Pro | Glu | Ser | |
| | | | | 445 | | | | | 450 | | | | | 455 | | |
| tca | cag | ctg | ttt | gcc | aag | ctg | ctc | cag | aaa | atg | aca | gac | ctc | aga | cag | 1506 |
| Ser | Gln | Leu | Phe | Ala | Lys | Leu | Leu | Gln | Lys | Met | Thr | Asp | Leu | Arg | Gln | |
| | | | 460 | | | | | 465 | | | | | 470 | | | |
| att | gtc | acg | gaa | cac | gtg | cag | cta | ctg | cag | gtg | atc | aag | aag | acg | gag | 1554 |
| Ile | Val | Thr | Glu | His | Val | Gln | Leu | Leu | Gln | Val | Ile | Lys | Lys | Thr | Glu | |
| | | 475 | | | | | 480 | | | | | 485 | | | | |
| aca | gac | atg | agt | ctt | cac | ccg | ctc | ctg | cag | gag | atc | tac | aag | gac | ttg | 1602 |
| Thr | Asp | Met | Ser | Leu | His | Pro | Leu | Leu | Gln | Glu | Ile | Tyr | Lys | Asp | Leu | |
| | 490 | | | | | 495 | | | | | 500 | | | | | |
| tac | tag | | | | | | | | | | | | | | | 1608 |
| Tyr | * | | | | | | | | | | | | | | | |
| 505 | | | | | | | | | | | | | | | | |

<210> SEQ ID NO 16
<211> LENGTH: 505
<212> TYPE: PRT
<213> ORGANISM: Homo Sapiens

<400> SEQUENCE: 16

Met Gly Glu Thr Leu Gly Asp Ser Pro Ile Asp Pro Glu Ser Asp Ser

```
  1               5                   10                  15
Phe Thr Asp Thr Leu Ser Ala Asn Ile Ser Gln Glu Met Thr Met Val
                    20                  25                  30
Asp Thr Glu Met Pro Phe Trp Pro Thr Asn Phe Gly Ile Ser Ser Val
                35                  40                  45
Asp Leu Ser Val Met Glu Asp His Ser His Ser Phe Asp Ile Lys Pro
            50                  55                  60
Phe Thr Thr Val Asp Phe Ser Ser Ile Ser Thr Pro His Tyr Glu Asp
65                      70                  75                  80
Ile Pro Phe Thr Arg Thr Asp Pro Val Val Ala Asp Tyr Lys Tyr Asp
                    85                  90                  95
Leu Lys Leu Gln Glu Tyr Gln Ser Ala Ile Lys Val Glu Pro Ala Ser
                100                 105                 110
Pro Pro Tyr Tyr Ser Glu Lys Thr Gln Leu Tyr Asn Lys Pro His Glu
            115                 120                 125
Glu Pro Ser Asn Ser Leu Met Ala Ile Glu Cys Arg Val Cys Gly Asp
            130                 135                 140
Lys Ala Ser Gly Phe His Tyr Gly Val His Ala Cys Glu Gly Cys Lys
145                 150                 155                 160
Gly Phe Phe Arg Arg Thr Ile Arg Leu Lys Leu Ile Tyr Asp Arg Cys
                165                 170                 175
Asp Leu Asn Cys Arg Ile His Lys Lys Ser Arg Asn Lys Cys Gln Tyr
                180                 185                 190
Cys Arg Phe Gln Lys Cys Leu Ala Val Gly Met Ser His Asn Ala Ile
            195                 200                 205
Arg Phe Gly Arg Met Pro Gln Ala Glu Lys Glu Lys Leu Leu Ala Glu
            210                 215                 220
Ile Ser Ser Asp Ile Asp Gln Leu Asn Pro Glu Ser Ala Asp Leu Arg
225                 230                 235                 240
Ala Leu Ala Lys His Leu Tyr Asp Ser Tyr Ile Lys Ser Phe Pro Leu
                245                 250                 255
Thr Lys Ala Lys Ala Arg Ala Ile Leu Thr Gly Lys Thr Thr Asp Lys
                260                 265                 270
Ser Pro Phe Val Ile Tyr Asp Met Asn Ser Leu Met Met Gly Glu Asp
            275                 280                 285
Lys Ile Lys Phe Lys His Ile Thr Pro Leu Gln Glu Gln Ser Lys Glu
290                 295                 300
Val Ala Ile Arg Ile Phe Gln Gly Cys Gln Phe Arg Ser Val Glu Ala
305                 310                 315                 320
Val Gln Glu Ile Thr Glu Tyr Ala Lys Ser Ile Pro Gly Phe Val Asn
                325                 330                 335
Leu Asp Leu Asn Asp Gln Val Thr Leu Leu Lys Tyr Gly Val His Glu
                340                 345                 350
Ile Ile Tyr Thr Met Leu Ala Ser Leu Met Asn Lys Asp Gly Val Leu
                355                 360                 365
Ile Ser Glu Gly Gln Gly Phe Met Thr Arg Glu Phe Leu Lys Ser Leu
            370                 375                 380
Arg Lys Pro Phe Gly Asp Phe Met Glu Pro Lys Phe Glu Phe Ala Val
385                 390                 395                 400
Lys Phe Asn Ala Leu Glu Leu Asp Asp Ser Asp Leu Ala Ile Phe Ile
                405                 410                 415
Ala Val Ile Ile Leu Ser Gly Asp Arg Pro Gly Leu Leu Asn Val Lys
                420                 425                 430
```

```
Pro Ile Glu Asp Ile Gln Asp Asn Leu Leu Gln Ala Leu Glu Leu Gln
        435                 440                 445

Leu Lys Leu Asn His Pro Glu Ser Ser Gln Leu Phe Ala Lys Leu Leu
    450                 455                 460

Gln Lys Met Thr Asp Leu Arg Gln Ile Val Thr Glu His Val Gln Leu
465                 470                 475                 480

Leu Gln Val Ile Lys Lys Thr Glu Thr Asp Met Ser Leu His Pro Leu
                485                 490                 495

Leu Gln Glu Ile Tyr Lys Asp Leu Tyr
            500                 505

<210> SEQ ID NO 17
<211> LENGTH: 21
<212> TYPE: DNA
<213> ORGANISM: Homo Sapiens

<400> SEQUENCE: 17
gcattgactc acagagcagc a                                           21

<210> SEQ ID NO 18
<211> LENGTH: 18
<212> TYPE: DNA
<213> ORGANISM: Homo Sapiens

<400> SEQUENCE: 18
gctcaacagc accctgga                                               18

<210> SEQ ID NO 19
<211> LENGTH: 20
<212> TYPE: DNA
<213> ORGANISM: Homo Sapiens

<400> SEQUENCE: 19
gcaacctctc gactcaccag                                             20

<210> SEQ ID NO 20
<211> LENGTH: 20
<212> TYPE: DNA
<213> ORGANISM: Homo Sapiens

<400> SEQUENCE: 20
caaaggagtg ggagtggtct                                             20

<210> SEQ ID NO 21
<211> LENGTH: 20
<212> TYPE: DNA
<213> ORGANISM: Homo Sapiens

<400> SEQUENCE: 21
cattacggag agatccacgg                                             20

<210> SEQ ID NO 22
<211> LENGTH: 2596
<212> TYPE: DNA
<213> ORGANISM: Homo Sapiens
<220> FEATURE:
<221> NAME/KEY: CDS
<222> LOCATION: (161)...(2596)

<400> SEQUENCE: 22
ttcagaagga ggagagacac cgggcccagg gcaccctcgc gggcgggcgg acccaagcag    60
```

-continued

```
tgagggcctg cagccggccg gccagggcag cggcaggcgc ggcccggacc tacgggagga      120
agccccgagc cctcggcggg ctgcgagcga ctccccggcg atg cct cac aac tcc       175
                                             Met Pro His Asn Ser
                                              1               5 atc aga tct ggc cat gga ggg ctg aac cag ctg gga ggg gcc ttt gtg       223
Ile Arg Ser Gly His Gly Gly Leu Asn Gln Leu Gly Gly Ala Phe Val
                10              15                  20 aat ggc aga cct ctg ccg gaa gtg gtc cgc cag cgc atc gta gac ctg       271
Asn Gly Arg Pro Leu Pro Glu Val Val Arg Gln Arg Ile Val Asp Leu
            25                  30                  35 gcc cac cag ggt gta agg ccc tgc gac atc tct cgc cag ctc cgc gtc       319
Ala His Gln Gly Val Arg Pro Cys Asp Ile Ser Arg Gln Leu Arg Val
        40                  45                  50 agc cat ggc tgc gtc agc aag atc ctt ggc agg tac tac gag act ggc       367
Ser His Gly Cys Val Ser Lys Ile Leu Gly Arg Tyr Tyr Glu Thr Gly
    55                  60                  65 agc atc cgg cct gga gtg ata ggg ggc tcc aag ccc aag gtg gcc acc       415
Ser Ile Arg Pro Gly Val Ile Gly Gly Ser Lys Pro Lys Val Ala Thr
70                  75                  80                      85 ccc aag gtg gtg gag aag att ggg gac tac aaa cgc cag aac cct acc       463
Pro Lys Val Val Glu Lys Ile Gly Asp Tyr Lys Arg Gln Asn Pro Thr
                90                  95                  100 atg ttt gcc tgg gag atc cga gac cgg ctc ctg gct gag ggc gtc tgt       511
Met Phe Ala Trp Glu Ile Arg Asp Arg Leu Leu Ala Glu Gly Val Cys
            105                 110                 115 gac aat gac act gtg ccc agt gtc agc tcc att aat aga atc atc cgg       559
Asp Asn Asp Thr Val Pro Ser Val Ser Ser Ile Asn Arg Ile Ile Arg
        120                 125                 130 acc aaa gtg cag caa cca ttc aac ctc cct atg gac agc tgc gtg gcc       607
Thr Lys Val Gln Gln Pro Phe Asn Leu Pro Met Asp Ser Cys Val Ala
    135                 140                 145 acc aag tcc ctg agt ccc gga cac acg ctg atc ccc agc tca gct gta       655
Thr Lys Ser Leu Ser Pro Gly His Thr Leu Ile Pro Ser Ser Ala Val
150                 155                 160                     165 act ccc ccg gag tca ccc cag tcg gat tcc ctg ggc tcc acc tac tcc       703
Thr Pro Pro Glu Ser Pro Gln Ser Asp Ser Leu Gly Ser Thr Tyr Ser
                170                 175                 180 atc aat ggg ctc ctg ggc atc gct cag cct ggc agc gac aag agg aaa       751
Ile Asn Gly Leu Leu Gly Ile Ala Gln Pro Gly Ser Asp Lys Arg Lys
            185                 190                 195 atg gat gac agt gat cag gat agc tgc cga cta agc att gac tca cag       799
Met Asp Asp Ser Asp Gln Asp Ser Cys Arg Leu Ser Ile Asp Ser Gln
        200                 205                 210 agc agc agc agc gga ccc cga aag cac ctt cgc acg gat gcc ttc agc       847
Ser Ser Ser Ser Gly Pro Arg Lys His Leu Arg Thr Asp Ala Phe Ser
    215                 220                 225 cag cac cac ctc gag ccg ctc gag tgc cca ttt gag cgg cag cac tac       895
Gln His His Leu Glu Pro Leu Glu Cys Pro Phe Glu Arg Gln His Tyr
230                 235                 240                     245 cca gag gcc tat gcc tcc ccc agc cac acc aaa ggc gag cag ggc ctc       943
Pro Glu Ala Tyr Ala Ser Pro Ser His Thr Lys Gly Glu Gln Gly Leu
                250                 255                 260 tac ccg ctg ccc ttg ctc aac agc acc ctg gac gac ggg aag gcc acc       991
Tyr Pro Leu Pro Leu Leu Asn Ser Thr Leu Asp Asp Gly Lys Ala Thr
            265                 270                 275 ctg acc cct tcc aac acg cca ctg ggg cgc aac ctc tcg act cac cag       1039
Leu Thr Pro Ser Asn Thr Pro Leu Gly Arg Asn Leu Ser Thr His Gln
        280                 285                 290 acc tac ccc gtg gtg gca ggg cga gag atg gtg ggg ccc acg ctg ccc       1087
Thr Tyr Pro Val Val Ala Gly Arg Glu Met Val Gly Pro Thr Leu Pro
```

```
                                                                    -continued Thr Tyr Pro Val Val Ala Gly Arg Glu Met Val Gly Pro Thr Leu Pro
    295                 300                 305 gga tac cca ccc cac atc ccc acc agc gga cag ggc agc tat gcc tcc    1135
Gly Tyr Pro Pro His Ile Pro Thr Ser Gly Gln Gly Ser Tyr Ala Ser
310                 315                 320                 325 tct gcc atc gca ggc atg gtg gca gaa atg acc atg gtt gac aca gag    1183
Ser Ala Ile Ala Gly Met Val Ala Glu Met Thr Met Val Asp Thr Glu
                330                 335                 340 atg cca ttc tgg ccc acc aac ttt ggg atc agc tcc gtg gat ctc tcc    1231
Met Pro Phe Trp Pro Thr Asn Phe Gly Ile Ser Ser Val Asp Leu Ser
            345                 350                 355 gta atg gaa gac cac tcc cac tcc ttt gat atc aag ccc ttc act act    1279
Val Met Glu Asp His Ser His Ser Phe Asp Ile Lys Pro Phe Thr Thr
        360                 365                 370 gtt gac ttc tcc agc att tct act cca cat tac gaa gac att cca ttc    1327
Val Asp Phe Ser Ser Ile Ser Thr Pro His Tyr Glu Asp Ile Pro Phe
    375                 380                 385 aca aga aca gat cca gtg gtt gca gat tac aag tat gac ctg aaa ctt    1375
Thr Arg Thr Asp Pro Val Val Ala Asp Tyr Lys Tyr Asp Leu Lys Leu
390                 395                 400                 405 caa gag tac caa agt gca atc aaa gtg gag cct gca tct cca cct tat    1423
Gln Glu Tyr Gln Ser Ala Ile Lys Val Glu Pro Ala Ser Pro Pro Tyr
                410                 415                 420 tat tct gag aag act cag ctc tac aat aag cct cat gaa gag cct tcc    1471
Tyr Ser Glu Lys Thr Gln Leu Tyr Asn Lys Pro His Glu Glu Pro Ser
            425                 430                 435 aac tcc ctc atg gca att gaa tgt cgt gtc tgt gga gat aaa gct tct    1519
Asn Ser Leu Met Ala Ile Glu Cys Arg Val Cys Gly Asp Lys Ala Ser
        440                 445                 450 gga ttt cac tat gga gtt cat gct tgt gaa gga tgc aag ggt ttc ttc    1567
Gly Phe His Tyr Gly Val His Ala Cys Glu Gly Cys Lys Gly Phe Phe
    455                 460                 465 cgg aga aca atc aga ttg aag ctt atc tat gac aga tgt gat ctt aac    1615
Arg Arg Thr Ile Arg Leu Lys Leu Ile Tyr Asp Arg Cys Asp Leu Asn
470                 475                 480                 485 tgt cgg atc cac aaa aaa agt aga aat aaa tgt cag tac tgt cgg ttt    1663
Cys Arg Ile His Lys Lys Ser Arg Asn Lys Cys Gln Tyr Cys Arg Phe
                490                 495                 500 cag aaa tgc ctt gca gtg ggg atg tct cat aat gcc atc agg ttt ggg    1711
Gln Lys Cys Leu Ala Val Gly Met Ser His Asn Ala Ile Arg Phe Gly
            505                 510                 515 cgg atg cca cag gcc gag aag gag aag ctg ttg gcg gag atc tcc agt    1759
Arg Met Pro Gln Ala Glu Lys Glu Lys Leu Leu Ala Glu Ile Ser Ser
        520                 525                 530 gat atc gac cag ctg aat cca gag tcc gct gac ctc cgg gcc ctg gca    1807
Asp Ile Asp Gln Leu Asn Pro Glu Ser Ala Asp Leu Arg Ala Leu Ala
    535                 540                 545 aaa cat ttg tat gac tca tac ata aag tcc ttc ccg ctg acc aaa gca    1855
Lys His Leu Tyr Asp Ser Tyr Ile Lys Ser Phe Pro Leu Thr Lys Ala
550                 555                 560                 565 aag gcg agg gcg atc ttg aca gga aag aca aca gac aaa tca cca ttc    1903
Lys Ala Arg Ala Ile Leu Thr Gly Lys Thr Thr Asp Lys Ser Pro Phe
                570                 575                 580 gtt atc tat gac atg aat tcc tta atg atg gga gaa gat aaa atc aag    1951
Val Ile Tyr Asp Met Asn Ser Leu Met Met Gly Glu Asp Lys Ile Lys
            585                 590                 595 ttc aaa cac atc acc ccc ctg cag gag cag agc aaa gag gtg gcc atc    1999
Phe Lys His Ile Thr Pro Leu Gln Glu Gln Ser Lys Glu Val Ala Ile
        600                 605                 610
```

```
cgc atc ttt cag ggc tgc cag ttt cgc tcc gtg gag gct gtg cag gag    2047
Arg Ile Phe Gln Gly Cys Gln Phe Arg Ser Val Glu Ala Val Gln Glu
    615                 620                 625 atc aca gag tat gcc aaa agc att cct ggt ttt gta aat ctt gac ttg    2095
Ile Thr Glu Tyr Ala Lys Ser Ile Pro Gly Phe Val Asn Leu Asp Leu
630                 635                 640                 645 aac gac caa gta act ctc ctc aaa tat gga gtc cac gag atc att tac    2143
Asn Asp Gln Val Thr Leu Leu Lys Tyr Gly Val His Glu Ile Ile Tyr
                650                 655                 660 aca atg ctg gcc tcc ttg atg aat aaa gat ggg gtt ctc ata tcc gag    2191
Thr Met Leu Ala Ser Leu Met Asn Lys Asp Gly Val Leu Ile Ser Glu
            665                 670                 675 ggc caa ggc ttc atg aca agg gag ttt cta aag agc ctg cga aag cct    2239
Gly Gln Gly Phe Met Thr Arg Glu Phe Leu Lys Ser Leu Arg Lys Pro
        680                 685                 690 ttt ggt gac ttt atg gag ccc aag ttt gag ttt gct gtg aag ttc aat    2287
Phe Gly Asp Phe Met Glu Pro Lys Phe Glu Phe Ala Val Lys Phe Asn
    695                 700                 705 gca ctg gaa tta gat gac agc gac ttg gca ata ttt att gct gtc att    2335
Ala Leu Glu Leu Asp Asp Ser Asp Leu Ala Ile Phe Ile Ala Val Ile
710                 715                 720                 725 att ctc agt gga gac cgc cca ggt ttg ctg aat gtg aag ccc att gaa    2383
Ile Leu Ser Gly Asp Arg Pro Gly Leu Leu Asn Val Lys Pro Ile Glu
                730                 735                 740 gac att caa gac aac ctg cta caa gcc ctg gag ctc cag ctg aag ctg    2431
Asp Ile Gln Asp Asn Leu Leu Gln Ala Leu Glu Leu Gln Leu Lys Leu
            745                 750                 755 aac cac cct gag tcc tca cag ctg ttt gcc aag ctg ctc cag aaa atg    2479
Asn His Pro Glu Ser Ser Gln Leu Phe Ala Lys Leu Leu Gln Lys Met
        760                 765                 770 aca gac ctc aga cag att gtc acg gaa cac gtg cag cta ctg cag gtg    2527
Thr Asp Leu Arg Gln Ile Val Thr Glu His Val Gln Leu Leu Gln Val
    775                 780                 785 atc aag aag acg gag aca gac atg agt ctt cac ccg ctc ctg cag gag    2575
Ile Lys Lys Thr Glu Thr Asp Met Ser Leu His Pro Leu Leu Gln Glu
790                 795                 800                 805 atc tac aag gac ttg tac tag                                        2596
Ile Tyr Lys Asp Leu Tyr *
                810

<210> SEQ ID NO 23
<211> LENGTH: 811
<212> TYPE: PRT
<213> ORGANISM: Homo Sapiens

<400> SEQUENCE: 23

Met Pro His Asn Ser Ile Arg Ser Gly His Gly Gly Leu Asn Gln Leu
1               5                   10                  15

Gly Gly Ala Phe Val Asn Gly Arg Pro Leu Pro Glu Val Val Arg Gln
            20                  25                  30

Arg Ile Val Asp Leu Ala His Gln Gly Val Arg Pro Cys Asp Ile Ser
        35                  40                  45

Arg Gln Leu Arg Val Ser His Gly Cys Val Ser Lys Ile Leu Gly Arg
    50                  55                  60

Tyr Tyr Glu Thr Gly Ser Ile Arg Pro Gly Val Ile Gly Gly Ser Lys
65                  70                  75                  80

Pro Lys Val Ala Thr Pro Lys Val Val Glu Lys Ile Gly Asp Tyr Lys
                85                  90                  95

Arg Gln Asn Pro Thr Met Phe Ala Trp Glu Ile Arg Asp Arg Leu Leu
```

-continued

```
            100                 105                 110
Ala Glu Gly Val Cys Asp Asn Asp Thr Val Pro Ser Val Ser Ser Ile
            115                 120                 125

Asn Arg Ile Ile Arg Thr Lys Val Gln Gln Pro Phe Asn Leu Pro Met
            130                 135                 140

Asp Ser Cys Val Ala Thr Lys Ser Leu Ser Pro Gly His Thr Leu Ile
145                 150                 155                 160

Pro Ser Ser Ala Val Thr Pro Pro Glu Ser Pro Gln Ser Asp Ser Leu
                165                 170                 175

Gly Ser Thr Tyr Ser Ile Asn Gly Leu Leu Gly Ile Ala Gln Pro Gly
                180                 185                 190

Ser Asp Lys Arg Lys Met Asp Asp Ser Asp Gln Asp Ser Cys Arg Leu
            195                 200                 205

Ser Ile Asp Ser Gln Ser Ser Ser Gly Pro Arg Lys His Leu Arg
            210                 215                 220

Thr Asp Ala Phe Ser Gln His His Leu Glu Pro Leu Glu Cys Pro Phe
225                 230                 235                 240

Glu Arg Gln His Tyr Pro Glu Ala Tyr Ala Ser Pro Ser His Thr Lys
                245                 250                 255

Gly Glu Gln Gly Leu Tyr Pro Leu Pro Leu Leu Asn Ser Thr Leu Asp
                260                 265                 270

Asp Gly Lys Ala Thr Leu Thr Pro Ser Asn Thr Pro Leu Gly Arg Asn
            275                 280                 285

Leu Ser Thr His Gln Thr Tyr Pro Val Val Ala Gly Arg Glu Met Val
            290                 295                 300

Gly Pro Thr Leu Pro Gly Tyr Pro Pro His Ile Pro Thr Ser Gly Gln
305                 310                 315                 320

Gly Ser Tyr Ala Ser Ser Ala Ile Ala Gly Met Val Ala Glu Met Thr
                325                 330                 335

Met Val Asp Thr Glu Met Pro Phe Trp Pro Thr Asn Phe Gly Ile Ser
                340                 345                 350

Ser Val Asp Leu Ser Val Met Glu Asp His Ser His Ser Phe Asp Ile
            355                 360                 365

Lys Pro Phe Thr Thr Val Asp Phe Ser Ser Ile Ser Thr Pro His Tyr
            370                 375                 380

Glu Asp Ile Pro Phe Thr Arg Thr Asp Pro Val Val Ala Asp Tyr Lys
385                 390                 395                 400

Tyr Asp Leu Lys Leu Gln Glu Tyr Gln Ser Ala Ile Lys Val Glu Pro
                405                 410                 415

Ala Ser Pro Pro Tyr Tyr Ser Glu Lys Thr Gln Leu Tyr Asn Lys Pro
                420                 425                 430

His Glu Glu Pro Ser Asn Ser Leu Met Ala Ile Glu Cys Arg Val Cys
            435                 440                 445

Gly Asp Lys Ala Ser Gly Phe His Tyr Gly Val His Ala Cys Glu Gly
            450                 455                 460

Cys Lys Gly Phe Phe Arg Arg Thr Ile Arg Leu Lys Leu Ile Tyr Asp
465                 470                 475                 480

Arg Cys Asp Leu Asn Cys Arg Ile His Lys Lys Ser Arg Asn Lys Cys
                485                 490                 495

Gln Tyr Cys Arg Phe Gln Lys Cys Leu Ala Val Gly Met Ser His Asn
                500                 505                 510

Ala Ile Arg Phe Gly Arg Met Pro Gln Ala Glu Lys Glu Lys Leu Leu
            515                 520                 525
```

-continued

```
Ala Glu Ile Ser Ser Asp Ile Asp Gln Leu Asn Pro Glu Ser Ala Asp
        530                 535                 540

Leu Arg Ala Leu Ala Lys His Leu Tyr Asp Ser Tyr Ile Lys Ser Phe
545                 550                 555                 560

Pro Leu Thr Lys Ala Lys Ala Arg Ala Ile Leu Thr Gly Lys Thr Thr
                565                 570                 575

Asp Lys Ser Pro Phe Val Ile Tyr Asp Met Asn Ser Leu Met Met Gly
            580                 585                 590

Glu Asp Lys Ile Lys Phe Lys His Ile Thr Pro Leu Gln Glu Gln Ser
        595                 600                 605

Lys Glu Val Ala Ile Arg Ile Phe Gln Gly Cys Gln Phe Arg Ser Val
610                 615                 620

Glu Ala Val Gln Glu Ile Thr Glu Tyr Ala Lys Ser Ile Pro Gly Phe
625                 630                 635                 640

Val Asn Leu Asp Leu Asn Asp Gln Val Thr Leu Leu Lys Tyr Gly Val
                645                 650                 655

His Glu Ile Ile Tyr Thr Met Leu Ala Ser Leu Met Asn Lys Asp Gly
                660                 665                 670

Val Leu Ile Ser Glu Gly Gln Gly Phe Met Thr Arg Glu Phe Leu Lys
            675                 680                 685

Ser Leu Arg Lys Pro Phe Gly Asp Phe Met Glu Pro Lys Phe Glu Phe
        690                 695                 700

Ala Val Lys Phe Asn Ala Leu Glu Leu Asp Asp Ser Asp Leu Ala Ile
705                 710                 715                 720

Phe Ile Ala Val Ile Ile Leu Ser Gly Asp Arg Pro Gly Leu Leu Asn
                725                 730                 735

Val Lys Pro Ile Glu Asp Ile Gln Asp Asn Leu Leu Gln Ala Leu Glu
                740                 745                 750

Leu Gln Leu Lys Leu Asn His Pro Glu Ser Ser Gln Leu Phe Ala Lys
            755                 760                 765

Leu Leu Gln Lys Met Thr Asp Leu Arg Gln Ile Val Thr Glu His Val
770                 775                 780

Gln Leu Leu Gln Val Ile Lys Lys Thr Glu Thr Asp Met Ser Leu His
785                 790                 795                 800

Pro Leu Leu Gln Glu Ile Tyr Lys Asp Leu Tyr
                805                 810

<210> SEQ ID NO 24
<211> LENGTH: 2711
<212> TYPE: DNA
<213> ORGANISM: Homo Sapiens
<220> FEATURE:
<221> NAME/KEY: CDS
<222> LOCATION: (161)...(1510)

<400> SEQUENCE: 24
ttcagaagga gggagagacac cgggcccagg gcaccctcgc gggcgggcgg acccaagcag     60
tgagggcctg cagccggccg gccagggcag cggcaggcgc ggcccggacc tacgggagga    120
agccccgagc cctcggcggg ctgcgagcga ctccccggcg atg cct cac aac tcc      175
                                              Met Pro His Asn Ser
                                                1               5 atc aga tct ggc cat gga ggg ctg aac cag ctg gga ggg gcc ttt gtg      223
Ile Arg Ser Gly His Gly Gly Leu Asn Gln Leu Gly Gly Ala Phe Val
            10                  15                  20 aat ggc aga cct ctg ccg gaa gtg gtc cgc cag cgc atc gta gac ctg      271
```

```
Asn Gly Arg Pro Leu Pro Glu Val Val Arg Gln Arg Ile Val Asp Leu
            25                  30                  35 gcc cac cag ggt gta agg ccc tgc gac atc tct cgc cag ctc cgc gtc      319
Ala His Gln Gly Val Arg Pro Cys Asp Ile Ser Arg Gln Leu Arg Val
         40                  45                  50 agc cat ggc tgc gtc agc aag atc ctt ggc agg tac tac gag act ggc      367
Ser His Gly Cys Val Ser Lys Ile Leu Gly Arg Tyr Tyr Glu Thr Gly
     55                  60                  65 agc atc cgg cct gga gtg ata ggg ggc tcc aag ccc aag gtg gcc acc      415
Ser Ile Arg Pro Gly Val Ile Gly Gly Ser Lys Pro Lys Val Ala Thr
 70                  75                  80                  85 ccc aag gtg gtg gag aag att ggg gac tac aaa cgc cag aac cct acc      463
Pro Lys Val Val Glu Lys Ile Gly Asp Tyr Lys Arg Gln Asn Pro Thr
                 90                  95                 100 atg ttt gcc tgg gag atc cga gac cgg ctc ctg gct gag ggc gtc tgt      511
Met Phe Ala Trp Glu Ile Arg Asp Arg Leu Leu Ala Glu Gly Val Cys
                105                 110                 115 gac aat gac act gtg ccc agt gtc agc tcc att aat aga atc atc cgg      559
Asp Asn Asp Thr Val Pro Ser Val Ser Ser Ile Asn Arg Ile Ile Arg
            120                 125                 130 acc aaa gtg cag caa cca ttc aac ctc cct atg gac agc tgc gtg gcc      607
Thr Lys Val Gln Gln Pro Phe Asn Leu Pro Met Asp Ser Cys Val Ala
        135                 140                 145 acc aag tcc ctg agt ccc gga cac acg ctg atc ccc agc tca gct gta      655
Thr Lys Ser Leu Ser Pro Gly His Thr Leu Ile Pro Ser Ser Ala Val
150                 155                 160                 165 act ccc ccg gag tca ccc cag tcg gat tcc ctg ggc tcc acc tac tcc      703
Thr Pro Pro Glu Ser Pro Gln Ser Asp Ser Leu Gly Ser Thr Tyr Ser
                170                 175                 180 atc aat ggg ctc ctg ggc atc gct cag cct ggc agc gac aag agg aaa      751
Ile Asn Gly Leu Leu Gly Ile Ala Gln Pro Gly Ser Asp Lys Arg Lys
            185                 190                 195 atg gat gac agt gat cag gat agc tgc cga cta agc att gac tca cag      799
Met Asp Asp Ser Asp Gln Asp Ser Cys Arg Leu Ser Ile Asp Ser Gln
        200                 205                 210 agc agc agc agc gga ccc cga aag cac ctt cgc acg gat gcc ttc agc      847
Ser Ser Ser Ser Gly Pro Arg Lys His Leu Arg Thr Asp Ala Phe Ser
    215                 220                 225 cag cac cac ctc gag ccg ctc gag tgc cca ttt gag cgg cag cac tac      895
Gln His His Leu Glu Pro Leu Glu Cys Pro Phe Glu Arg Gln His Tyr
230                 235                 240                 245 cca gag gcc tat gcc tcc ccc agc cac acc aaa ggc gag cag ggc ctc      943
Pro Glu Ala Tyr Ala Ser Pro Ser His Thr Lys Gly Glu Gln Gly Leu
                250                 255                 260 tac ccg ctg ccc ttg ctc aac agc acc ctg gac gac ggg aag gcc acc      991
Tyr Pro Leu Pro Leu Leu Asn Ser Thr Leu Asp Asp Gly Lys Ala Thr
            265                 270                 275 ctg acc cct tcc aac acg cca ctg ggg cgc aac ctc tcg act cac cag     1039
Leu Thr Pro Ser Asn Thr Pro Leu Gly Arg Asn Leu Ser Thr His Gln
        280                 285                 290 acc tac ccc gtg gtg gca gat cct cac tca ccc ttg gcc ata aag cag     1087
Thr Tyr Pro Val Val Ala Asp Pro His Ser Pro Leu Ala Ile Lys Gln
    295                 300                 305 gaa acc ccc gag gtg tcc agt tct agc tcc acc cct tgc tct tta tct     1135
Glu Thr Pro Glu Val Ser Ser Ser Ser Thr Pro Cys Ser Leu Ser
310                 315                 320                 325 agc tcc gcc ctt ttg gat ctg cag caa gtc ggc tcc ggg gtc ccg ccc     1183
Ser Ser Ala Leu Leu Asp Leu Gln Gln Val Gly Ser Gly Val Pro Pro
            330                 335                 340
```

-continued

| | | |
|---|---|---|
| ttc aat gcc ttt ccc cat gct gcc tcc gtg tac ggg cag ttc acg ggc<br>Phe Asn Ala Phe Pro His Ala Ala Ser Val Tyr Gly Gln Phe Thr Gly<br>345 350 355 | 1231 | |
| cag gcc ctc ctc tca ggg cga gag atg gtg ggg ccc acg ctg ccc gga<br>Gln Ala Leu Leu Ser Gly Arg Glu Met Val Gly Pro Thr Leu Pro Gly<br>360 365 370 | 1279 | |
| tac cca ccc cac atc ccc acc agc gga cag ggc agc tat gcc tcc tct<br>Tyr Pro Pro His Ile Pro Thr Ser Gly Gln Gly Ser Tyr Ala Ser Ser<br>375 380 385 | 1327 | |
| gcc atc gca ggc atg gtg gca gga agt gaa tac tct ggc aat gcc tat<br>Ala Ile Ala Gly Met Val Ala Gly Ser Glu Tyr Ser Gly Asn Ala Tyr<br>390 395 400 405 | 1375 | |
| ggc cac acc ccc tac tcc tcc tac agc gag gcc tgg ggc ttc ccc aac<br>Gly His Thr Pro Tyr Ser Ser Tyr Ser Glu Ala Trp Gly Phe Pro Asn<br>410 415 420 | 1423 | |
| tcc agc ttg ctg agt tcc cca tat tat tac agt tcc aca tca agg ccg<br>Ser Ser Leu Leu Ser Ser Pro Tyr Tyr Tyr Ser Ser Thr Ser Arg Pro<br>425 430 435 | 1471 | |
| agt gca ccg ccc acc act gcc acg gcc ttt gac cat ctg tagttgccat<br>Ser Ala Pro Pro Thr Thr Ala Thr Ala Phe Asp His Leu<br>440 445 450 | 1520 | |
| ggggacagtg ggagcgactg agcaacagga ggactcagcc tgggacaggc cccagagagt | 1580 | |
| cacacaaagg aatctttatt attacatgaa aaataaccac aagtccagca ttgcggcaca | 1640 | |
| ctccctgtgt ggttaattta atgaaccatg aaagacagga tgaccttgga caaggccaaa | 1700 | |
| ctgtcctcca agactcctta atgaggggca ggagtcccag ggaaagagaa ccatgccatg | 1760 | |
| ctgaaaaaga caaaattgaa gaagaaatgt agccccagcc ggtaccctcc aaaggagaga | 1820 | |
| agaagcaata gccgaggaac ttgggggggat ggcgaatggt tcctgcccgg gcccaagggt | 1880 | |
| gcacagggca cctccatggc tccattatta acacaactct agcaattatg gaccataagc | 1940 | |
| acttccctcc agcccacaag tcacagcctg gtgccgaggc tctgctcacc agccacccag | 2000 | |
| ggagtcacct ccctcagcct cccgcctgcc ccacacggag gctctggctg tcctctttcc | 2060 | |
| tccactccat ttgcttggct ctttctacac ctccctcttg gatgggctga gggctggagc | 2120 | |
| gagtccctca gaaattccac caggctgtca gctgacctct ttttcctgct gctgtgaagg | 2180 | |
| tatagcacca cccaggtcct cctgcagtgc ggcatcccct tggcagctgc cgtcagccag | 2240 | |
| gccagcccca gggagcttaa aacagacatt ccacagggcc tgggcccctg ggaggtgagg | 2300 | |
| tgtggtgtgc ggcttcaccc agggcagaac aaggcagaat cgcaggaaac ccgcttcccc | 2360 | |
| ttcctgacag ctcctgccaa gccaaatgtg cttcctgcag ctcacgccca ccagctactg | 2420 | |
| aagggaccca aggcaccccc tgaagccagc gatagagggt ccctctctgc tccccagcag | 2480 | |
| ctcctgcccc caaggcctga ctgtatatac tgtaaatgaa actttgtttg ggtcaagctt | 2540 | |
| ccttctttct aaccccccaga cttttggcctc tgagtgaaat gtctctcttt gccctgtggg | 2600 | |
| gcttctctcc ttgatgcttc tttctttttt taaagacaac ctgccattac cacatgactc | 2660 | |
| aataaaccat tgctcttcaa aaaaaaaaaa aaaaaaaaaa aaaaaaaaa a | 2711 | |

<210> SEQ ID NO 25
<211> LENGTH: 450
<212> TYPE: PRT
<213> ORGANISM: Homo Sapiens

<400> SEQUENCE: 25

Met Pro His Asn Ser Ile Arg Ser Gly His Gly Gly Leu Asn Gln Leu
1               5                   10                  15

-continued

```
Gly Gly Ala Phe Val Asn Gly Arg Pro Leu Pro Glu Val Val Arg Gln
             20                  25                  30

Arg Ile Val Asp Leu Ala His Gln Gly Val Arg Pro Cys Asp Ile Ser
         35                  40                  45

Arg Gln Leu Arg Val Ser His Gly Cys Val Ser Lys Ile Leu Gly Arg
     50                  55                  60

Tyr Tyr Glu Thr Gly Ser Ile Arg Pro Gly Val Ile Gly Gly Ser Lys
 65                  70                  75                  80

Pro Lys Val Ala Thr Pro Lys Val Glu Lys Ile Gly Asp Tyr Lys
                 85                  90                  95

Arg Gln Asn Pro Thr Met Phe Ala Trp Glu Ile Arg Asp Arg Leu Leu
             100                 105                 110

Ala Glu Gly Val Cys Asp Asn Asp Thr Val Pro Ser Val Ser Ser Ile
         115                 120                 125

Asn Arg Ile Ile Arg Thr Lys Val Gln Gln Pro Phe Asn Leu Pro Met
 130                 135                 140

Asp Ser Cys Val Ala Thr Lys Ser Leu Ser Pro Gly His Thr Leu Ile
 145                 150                 155                 160

Pro Ser Ser Ala Val Thr Pro Pro Glu Ser Pro Gln Ser Asp Ser Leu
                 165                 170                 175

Gly Ser Thr Tyr Ser Ile Asn Gly Leu Leu Gly Ile Ala Gln Pro Gly
             180                 185                 190

Ser Asp Lys Arg Lys Met Asp Asp Ser Asp Gln Asp Ser Cys Arg Leu
             195                 200                 205

Ser Ile Asp Ser Gln Ser Ser Ser Gly Pro Arg Lys His Leu Arg
     210                 215                 220

Thr Asp Ala Phe Ser Gln His His Leu Glu Pro Leu Glu Cys Pro Phe
 225                 230                 235                 240

Glu Arg Gln His Tyr Pro Glu Ala Tyr Ala Ser Pro Ser His Thr Lys
             245                 250                 255

Gly Glu Gln Gly Leu Tyr Pro Leu Pro Leu Asn Ser Thr Leu Asp
             260                 265                 270

Asp Gly Lys Ala Thr Leu Thr Pro Ser Asn Thr Pro Leu Gly Arg Asn
 275                 280                 285

Leu Ser Thr His Gln Thr Tyr Pro Val Val Ala Asp Pro His Ser Pro
 290                 295                 300

Leu Ala Ile Lys Gln Glu Thr Pro Glu Val Ser Ser Ser Ser Ser Thr
 305                 310                 315                 320

Pro Cys Ser Leu Ser Ser Ser Ala Leu Leu Asp Leu Gln Gln Val Gly
                 325                 330                 335

Ser Gly Val Pro Pro Phe Asn Ala Phe Pro His Ala Ala Ser Val Tyr
             340                 345                 350

Gly Gln Phe Thr Gly Gln Ala Leu Leu Ser Gly Arg Glu Met Val Gly
             355                 360                 365

Pro Thr Leu Pro Gly Tyr Pro Pro His Ile Pro Thr Ser Gly Gln Gly
 370                 375                 380

Ser Tyr Ala Ser Ser Ala Ile Ala Gly Met Val Ala Gly Ser Glu Tyr
 385                 390                 395                 400

Ser Gly Asn Ala Tyr Gly His Thr Pro Tyr Ser Ser Tyr Ser Glu Ala
             405                 410                 415

Trp Gly Phe Pro Asn Ser Ser Leu Leu Ser Ser Pro Tyr Tyr Tyr Ser
             420                 425                 430

Ser Thr Ser Arg Pro Ser Ala Pro Pro Thr Thr Ala Thr Ala Phe Asp
```

-continued

```
                 435                 440                 445
His Leu
    450

<210> SEQ ID NO 26
<211> LENGTH: 1811
<212> TYPE: DNA
<213> ORGANISM: Homo Sapiens
<220> FEATURE:
<221> NAME/KEY: CDS
<222> LOCATION: (173)...(1609)

<400> SEQUENCE: 26
ccgaccttac cccaggcggc cttgacgttg gtcttgtcgg caggagacag caccatggtg      60
ggttctctct gagtctggga attcccgagc ccgagccgca gccgccgcct gggggggcttg    120 ggtcggcctc gaggacaccg gagagggcg ccacgccgcc gtggccgcag aa atg acc     178
                                                         Met Thr
                                                           1 atg gtt gac aca gag atc gca ttc tgg ccc acc aac ttt ggg atc agc      226
Met Val Asp Thr Glu Ile Ala Phe Trp Pro Thr Asn Phe Gly Ile Ser
         5                  10                  15 tcc gtg gat ctc tcc gta atg gaa gac cac tcc cac tcc ttt gat atc      274
Ser Val Asp Leu Ser Val Met Glu Asp His Ser His Ser Phe Asp Ile
     20                  25                  30 aag ccc ttc act act gtt gac ttc tcc agc att tct act cca cat tac      322
Lys Pro Phe Thr Thr Val Asp Phe Ser Ser Ile Ser Thr Pro His Tyr
 35                  40                  45                  50 gaa gac att cca ttc aca aga aca gat cca gtg gtt gca gat tac aag      370
Glu Asp Ile Pro Phe Thr Arg Thr Asp Pro Val Val Ala Asp Tyr Lys
                 55                  60                  65 tat gac ctg aaa ctt caa gag tac caa agt gca atc aaa gtg gag cct      418
Tyr Asp Leu Lys Leu Gln Glu Tyr Gln Ser Ala Ile Lys Val Glu Pro
             70                  75                  80 gca tct cca cct tat tat tct gag aag act cag ctc tac aat aag cct      466
Ala Ser Pro Pro Tyr Tyr Ser Glu Lys Thr Gln Leu Tyr Asn Lys Pro
         85                  90                  95 cat gaa gag cct tcc aac tcc ctc atg gca att gaa tgt cgt gtc tgt      514
His Glu Glu Pro Ser Asn Ser Leu Met Ala Ile Glu Cys Arg Val Cys
    100                 105                 110 gga gat aaa gct tct gga ttt cac tat gga gtt cat gct tgt gaa gga      562
Gly Asp Lys Ala Ser Gly Phe His Tyr Gly Val His Ala Cys Glu Gly
115                 120                 125                 130 tgc aag ggt ttc ttc cgg aga aca atc aga ttg aag ctt atc tat gac      610
Cys Lys Gly Phe Phe Arg Arg Thr Ile Arg Leu Lys Leu Ile Tyr Asp
                135                 140                 145 aga tgt gat ctt aac tgt cgg atc cac aaa aaa agt aga aat aaa tgt      658
Arg Cys Asp Leu Asn Cys Arg Ile His Lys Lys Ser Arg Asn Lys Cys
            150                 155                 160 cag tac tgt cgg ttt cag aaa tgc ctt gca gtg ggg atg tct cat aat      706
Gln Tyr Cys Arg Phe Gln Lys Cys Leu Ala Val Gly Met Ser His Asn
        165                 170                 175 gcc atc agg ttt ggg cgg atc gca cag gcc gag aag gag aag ctg ttg      754
Ala Ile Arg Phe Gly Arg Ile Ala Gln Ala Glu Lys Glu Lys Leu Leu
    180                 185                 190 gcg gag atc tcc agt gat atc gac cag ctg aat cca gag tcc gct gac      802
Ala Glu Ile Ser Ser Asp Ile Asp Gln Leu Asn Pro Glu Ser Ala Asp
195                 200                 205                 210 ctc cgt cag gcc ctg gca aaa cat ttg tat gac tca tac ata aag tcc      850
Leu Arg Gln Ala Leu Ala Lys His Leu Tyr Asp Ser Tyr Ile Lys Ser
                215                 220                 225
```

```
ttc ccg ctg acc aaa gca aag gcg agg gcg atc ttg aca gga aag aca      898
Phe Pro Leu Thr Lys Ala Lys Ala Arg Ala Ile Leu Thr Gly Lys Thr
            230                 235                 240 aca gac aaa tca cca ttc gtt atc tat gac atg aat tcc tta atg atg      946
Thr Asp Lys Ser Pro Phe Val Ile Tyr Asp Met Asn Ser Leu Met Met
                245                 250                 255 gga gaa gat aaa atc aag ttc aaa cac atc acc ccc ctg cag gag cag      994
Gly Glu Asp Lys Ile Lys Phe Lys His Ile Thr Pro Leu Gln Glu Gln
260                 265                 270 agc aaa gag gtg gcc atc cgc atc ttt cag ggc tgc cag ttt cgc tcc     1042
Ser Lys Glu Val Ala Ile Arg Ile Phe Gln Gly Cys Gln Phe Arg Ser
275                 280                 285                 290 gtg gag gct gtg cag gag atc aca gag tat gcc aaa agc att cct ggt     1090
Val Glu Ala Val Gln Glu Ile Thr Glu Tyr Ala Lys Ser Ile Pro Gly
                295                 300                 305 ttt gta aat ctt gac ttg aac gac caa gta act ctc ctc aaa tat gga     1138
Phe Val Asn Leu Asp Leu Asn Asp Gln Val Thr Leu Leu Lys Tyr Gly
            310                 315                 320 gtc cac gag atc att tac aca atg ctg gcc tcc ttg atg aat aaa gat     1186
Val His Glu Ile Ile Tyr Thr Met Leu Ala Ser Leu Met Asn Lys Asp
        325                 330                 335 ggg gtt ctc ata tcc gag ggc caa ggc ttc atg aca agg gag ttt cta     1234
Gly Val Leu Ile Ser Glu Gly Gln Gly Phe Met Thr Arg Glu Phe Leu
    340                 345                 350 aag agc ctg cga aag cct ttt ggt gac ttt atg gag ccc aag ttt gag     1282
Lys Ser Leu Arg Lys Pro Phe Gly Asp Phe Met Glu Pro Lys Phe Glu
355                 360                 365                 370 ttt gct gtg aag ttc aat gca ctg gaa tta gat gac agc gac ttg gca     1330
Phe Ala Val Lys Phe Asn Ala Leu Glu Leu Asp Asp Ser Asp Leu Ala
                375                 380                 385 ata ttt att gct gtc att att ctc agt gga gac cgc cca ggt ttg ctg     1378
Ile Phe Ile Ala Val Ile Ile Leu Ser Gly Asp Arg Pro Gly Leu Leu
            390                 395                 400 aat gtg aag ccc att gaa gac att caa gac aac ctg cta caa gcc ctg     1426
Asn Val Lys Pro Ile Glu Asp Ile Gln Asp Asn Leu Leu Gln Ala Leu
        405                 410                 415 gag ctc cag ctg aag ctg aac cac cct gag tcc tca cag ctg ttt gcc     1474
Glu Leu Gln Leu Lys Leu Asn His Pro Glu Ser Ser Gln Leu Phe Ala
    420                 425                 430 aag ctg ctc cag aaa atg aca gac ctc aga cag att gtc acg gaa cac     1522
Lys Leu Leu Gln Lys Met Thr Asp Leu Arg Gln Ile Val Thr Glu His
435                 440                 445                 450 gtg cag cta ctg cag gtg atc aag aag acg gag aca gac atg agt ctt     1570
Val Gln Leu Leu Gln Val Ile Lys Lys Thr Glu Thr Asp Met Ser Leu
                455                 460                 465 cac ccg ctc ctg cag gag atc tac aag gac ttg tac tag cagagagtcc      1619
His Pro Leu Leu Gln Glu Ile Tyr Lys Asp Leu Tyr *
            470                 475 tgagccactg ccaacatttc ccttcttcca gttgcactat tctgagggaa aatctgacca   1679
taagaaattt actgtgaaaa agcgttttaa aaagaaaagg gtttagaata tgatctattt   1739
tatgcatatt gtttataaag acacatttac aatttacttt taatattaaa aattaccata   1799
ttatgaaatt gc                                                       1811

<210> SEQ ID NO 27
<211> LENGTH: 478
<212> TYPE: PRT
<213> ORGANISM: Homo Sapiens
```

-continued

```
<400> SEQUENCE: 27

Met Thr Met Val Asp Thr Glu Ile Ala Phe Trp Pro Thr Asn Phe Gly
1               5                   10                  15

Ile Ser Ser Val Asp Leu Ser Val Met Glu Asp His Ser His Ser Phe
                20                  25                  30

Asp Ile Lys Pro Phe Thr Thr Val Asp Phe Ser Ser Ile Ser Thr Pro
            35                  40                  45

His Tyr Glu Asp Ile Pro Phe Thr Arg Thr Asp Pro Val Val Ala Asp
        50                  55                  60

Tyr Lys Tyr Asp Leu Lys Leu Gln Glu Tyr Gln Ser Ala Ile Lys Val
65                  70                  75                  80

Glu Pro Ala Ser Pro Tyr Tyr Ser Glu Lys Thr Gln Leu Tyr Asn
                85                  90                  95

Lys Pro His Glu Glu Pro Ser Asn Ser Leu Met Ala Ile Glu Cys Arg
            100                 105                 110

Val Cys Gly Asp Lys Ala Ser Gly Phe His Tyr Gly Val His Ala Cys
        115                 120                 125

Glu Gly Cys Lys Gly Phe Arg Arg Thr Ile Arg Leu Lys Leu Ile
130                 135                 140

Tyr Asp Arg Cys Asp Leu Asn Cys Arg Ile His Lys Lys Ser Arg Asn
145                 150                 155                 160

Lys Cys Gln Tyr Cys Arg Phe Gln Lys Cys Leu Ala Val Gly Met Ser
                165                 170                 175

His Asn Ala Ile Arg Phe Gly Arg Ile Ala Gln Ala Glu Lys Glu Lys
            180                 185                 190

Leu Leu Ala Glu Ile Ser Ser Asp Ile Asp Gln Leu Asn Pro Glu Ser
        195                 200                 205

Ala Asp Leu Arg Gln Ala Leu Ala Lys His Leu Tyr Asp Ser Tyr Ile
    210                 215                 220

Lys Ser Phe Pro Leu Thr Lys Ala Lys Ala Arg Ala Ile Leu Thr Gly
225                 230                 235                 240

Lys Thr Thr Asp Lys Ser Pro Phe Val Ile Tyr Asp Met Asn Ser Leu
                245                 250                 255

Met Met Gly Glu Asp Lys Ile Lys Phe Lys His Ile Thr Pro Leu Gln
            260                 265                 270

Glu Gln Ser Lys Glu Val Ala Ile Arg Ile Phe Gln Gly Cys Gln Phe
        275                 280                 285

Arg Ser Val Glu Ala Val Gln Glu Ile Thr Glu Tyr Ala Lys Ser Ile
    290                 295                 300

Pro Gly Phe Val Asn Leu Asp Leu Asn Asp Gln Val Thr Leu Leu Lys
305                 310                 315                 320

Tyr Gly Val His Glu Ile Ile Tyr Thr Met Leu Ala Ser Leu Met Asn
                325                 330                 335

Lys Asp Gly Val Leu Ile Ser Glu Gly Gln Gly Phe Met Thr Arg Glu
            340                 345                 350

Phe Leu Lys Ser Leu Arg Lys Pro Phe Gly Asp Phe Met Glu Pro Lys
        355                 360                 365

Phe Glu Phe Ala Val Lys Phe Asn Ala Leu Glu Leu Asp Asp Ser Asp
    370                 375                 380

Leu Ala Ile Phe Ile Ala Val Ile Ile Leu Ser Gly Asp Arg Pro Gly
385                 390                 395                 400

Leu Leu Asn Val Lys Pro Ile Glu Asp Ile Gln Asp Asn Leu Leu Gln
                405                 410                 415
```

-continued

```
Ala Leu Glu Leu Gln Leu Lys Leu Asn His Pro Glu Ser Ser Gln Leu
        420                 425                 430

Phe Ala Lys Leu Leu Gln Lys Met Thr Asp Leu Arg Gln Ile Val Thr
            435                 440                 445

Glu His Val Gln Leu Leu Gln Val Ile Lys Lys Thr Glu Thr Asp Met
    450                 455                 460

Ser Leu His Pro Leu Leu Gln Glu Ile Tyr Lys Asp Leu Tyr
465                 470                 475

<210> SEQ ID NO 28
<211> LENGTH: 20
<212> TYPE: DNA
<213> ORGANISM: Homo Sapiens

<400> SEQUENCE: 28
gccaccaagt ccctgagtcc                                              20

<210> SEQ ID NO 29
<211> LENGTH: 19
<212> TYPE: DNA
<213> ORGANISM: Homo Sapiens

<400> SEQUENCE: 29
gacctacggg aggaagccc                                               19

<210> SEQ ID NO 30
<211> LENGTH: 18
<212> TYPE: DNA
<213> ORGANISM: Homo Sapiens

<400> SEQUENCE: 30
gcggacccaa gcagtgag                                                18

<210> SEQ ID NO 31
<211> LENGTH: 21
<212> TYPE: DNA
<213> ORGANISM: Homo Sapiens

<400> SEQUENCE: 31
tttcttatgg tcagattttc c                                            21

<210> SEQ ID NO 32
<211> LENGTH: 21
<212> TYPE: DNA
<213> ORGANISM: Homo Sapiens

<400> SEQUENCE: 32
acccagaaag cgattccttc a                                            21

<210> SEQ ID NO 33
<211> LENGTH: 20
<212> TYPE: DNA
<213> ORGANISM: Homo Sapiens

<400> SEQUENCE: 33
atgggtgaaa ctctgggaga                                              20

<210> SEQ ID NO 34
<211> LENGTH: 20
<212> TYPE: DNA
<213> ORGANISM: Homo Sapiens
```

-continued

<210> SEQ ID NO 34

```
<400> SEQUENCE: 34
ttgctgcaga tccaaaaagg                                           20

<210> SEQ ID NO 35
<211> LENGTH: 20
<212> TYPE: DNA
<213> ORGANISM: Homo Sapiens

<400> SEQUENCE: 35
gaggaagggg tggagctaga                                           20

<210> SEQ ID NO 36
<211> LENGTH: 537
<212> TYPE: DNA
<213> ORGANISM: Homo Sapiens
<220> FEATURE:
<221> NAME/KEY: Unknown
<222> LOCATION: (85)...(85)
<223> OTHER INFORMATION: n = A or T or C or G or other

<400> SEQUENCE: 36 atg ggt gaa act ctg gga gat tct cct att gac cca gaa agc gat tcc    48 ttc act gat aca ctg tct gca aac ata tca caa gaa nat cct cac tca    96 ccc ttc gcc ata aag cag gaa acc ccc gag gtg tcc agt tct agc tcc   144 acc cct tcc tct tta tct agc tcc gcc ttt ttg gat ctg cag caa gtc   192 ggc tcc ggg gtc ccg ccc ttc aat gcc ttt ccc cat gct gcc tcc gtg   240 tac ggg cag ttc acg ggc cag gcc ctc ctc tca ggg cga gag atg gtg   288 ggg ccc acg ctg ccc gga tac cca ccc cac atc ccc acc agc gga cag   336 ggc agc tat gcc tcc tct gcc atc gca ggc atg gtg gca gga agt gaa   384 tac tct ggc aat gcc tat ggc cac acc ccc tac tcc tcc tac agc gag   432 gcc tgg cgc ttc ccc aac tcc agc ttg ctg agt tcc cca tat tat tac   480 agt tcc aca tca agg ccg agt gca ccg ccc acc act gcc acg gcc ttt   528 gac cat ctg                                                      537

<210> SEQ ID NO 37
<211> LENGTH: 348
<212> TYPE: DNA
<213> ORGANISM: Homo Sapiens
<220> FEATURE:
<221> NAME/KEY: Unknown
<222> LOCATION: (85)...(85)
<223> OTHER INFORMATION: n = A or T or C or G or other

<400> SEQUENCE: 37
atgggtgaaa ctctgggaga ttctcctatt gacccagaaa gcgattcctt cactgataca    60
ctgtctgcaa acatatcaca agaaggcga gagatggtgg ggcccacgct gcccggatac   120 ccacccaca tccccaccag cggacagggc agctatgcct cctctgccat cgcaggcatg   180
gtggcaggaa gtgaatactc tggcaatgcc tatggccaca cccctactc ctcctacagc   240 gaggcctggc gcttccccaa ctccagcttg ctgagttccc catattatta cagttccaca   300
tcaaggccga gtgcaccgcc caccactgcc acggcctttg accatctg               348

<210> SEQ ID NO 38
<211> LENGTH: 246
<212> TYPE: DNA
<213> ORGANISM: Homo Sapiens
```

```
<220> FEATURE:
<221> NAME/KEY: Unknown
<222> LOCATION: (85)...(85)
<223> OTHER INFORMATION: n = A or T or C or G or other

<400> SEQUENCE: 38
atgggtgaaa ctctgggaga ttctcctatt gacccagaaa gcgattcctt cactgataca      60
ctgtctgcaa acatatcaca agaangaagt gaatactctg gcaatgccta tggccacacc     120
ccctactcct cctacagcga ggcctggcgc ttccccaact ccagcttgct gagttcccca     180
tattattaca gttccacatc aaggccgagt gcaccgccca ccactgccac ggcctttgac     240
catctg                                                                246

<210> SEQ ID NO 39
<211> LENGTH: 178
<212> TYPE: PRT
<213> ORGANISM: Homo Sapiens
<220> FEATURE:
<221> NAME/KEY: Unknown
<222> LOCATION: (29)...(29)
<223> OTHER INFORMATION: Xaa = any amino acid

<400> SEQUENCE: 39

Met Gly Glu Thr Leu Gly Asp Ser Pro Ile Asp Pro Glu Ser Asp Ser
 1               5                  10                  15

Phe Thr Asp Thr Leu Ser Ala Asn Ile Ser Gln Glu Xaa Pro His Ser
                20                  25                  30

Pro Phe Ala Ile Lys Gln Glu Thr Pro Glu Val Ser Ser Ser Ser Ser
            35                  40                  45

Thr Pro Ser Ser Leu Ser Ser Ala Phe Leu Asp Leu Gln Gln Val
    50                  55                  60

Gly Ser Gly Val Pro Pro Phe Asn Ala Phe Pro His Ala Ala Ser Val
65                  70                  75                  80

Tyr Gly Gln Phe Thr Gly Gln Ala Leu Leu Ser Gly Arg Glu Met Val
                85                  90                  95

Gly Pro Thr Leu Pro Gly Tyr Pro Pro His Ile Pro Thr Ser Gly Gln
            100                 105                 110

Gly Ser Tyr Ala Ser Ser Ala Ile Ala Gly Met Val Ala Gly Ser Glu
        115                 120                 125

Tyr Ser Gly Asn Ala Tyr Gly His Thr Pro Tyr Ser Ser Tyr Ser Glu
    130                 135                 140

Ala Trp Arg Phe Pro Asn Ser Ser Leu Leu Ser Ser Pro Tyr Tyr Tyr
145                 150                 155                 160

Ser Ser Thr Ser Arg Pro Ala Pro Pro Thr Thr Ala Thr Ala Phe Asp
                165                 170                 175

His Leu

<210> SEQ ID NO 40
<211> LENGTH: 116
<212> TYPE: PRT
<213> ORGANISM: Homo Sapiens
<220> FEATURE:
<221> NAME/KEY: Unknown
<222> LOCATION: (29)...(29)
<223> OTHER INFORMATION: Xaa = any amino acid

<400> SEQUENCE: 40

Met Gly Glu Thr Leu Gly Asp Ser Pro Ile Asp Pro Glu Ser Asp Ser
 1               5                  10                  15
```

-continued

Phe Thr Asp Thr Leu Ser Ala Asn Ile Ser Gln Glu Xaa Arg Glu Met
             20                  25                  30

Val Gly Pro Thr Leu Pro Gly Tyr Pro Pro His Ile Pro Thr Ser Gly
         35                  40                  45

Gln Gly Ser Tyr Ala Ser Ser Ala Ile Ala Gly Met Val Ala Gly Ser
     50                  55                  60

Glu Tyr Ser Gly Asn Ala Tyr Gly His Thr Pro Tyr Ser Ser Tyr Ser
 65                  70                  75                  80

Glu Ala Trp Arg Phe Pro Asn Ser Ser Leu Leu Ser Ser Pro Tyr Tyr
                 85                  90                  95

Tyr Ser Ser Thr Ser Arg Pro Ser Ala Pro Pro Thr Thr Ala Thr Ala
             100                 105                 110

Phe Asp His Leu
        115

<210> SEQ ID NO 41
<211> LENGTH: 82
<212> TYPE: PRT
<213> ORGANISM: Homo Sapiens
<220> FEATURE:
<221> NAME/KEY: Unknown
<222> LOCATION: (29)...(29)
<223> OTHER INFORMATION: Xaa = any amino acid

<400> SEQUENCE: 41

Met Gly Glu Thr Leu Gly Asp Ser Pro Ile Asp Pro Glu Ser Asp Ser
  1               5                  10                  15

Phe Thr Asp Thr Leu Ser Ala Asn Ile Ser Gln Glu Xaa Ser Glu Tyr
             20                  25                  30

Ser Gly Asn Ala Tyr Gly His Thr Pro Tyr Ser Ser Tyr Ser Glu Ala
         35                  40                  45

Trp Arg Phe Pro Asn Ser Ser Leu Leu Ser Ser Pro Tyr Tyr Tyr Ser
     50                  55                  60

Ser Thr Ser Arg Pro Ser Ala Pro Pro Thr Thr Ala Thr Ala Phe Asp
 65                  70                  75                  80

His Leu

<210> SEQ ID NO 42
<211> LENGTH: 43
<212> TYPE: DNA
<213> ORGANISM: Homo Sapiens
<220> FEATURE:
<221> NAME/KEY: Unknown
<222> LOCATION: (22)...(22)
<223> OTHER INFORMATION: n = A or T or C or G or other
<221> NAME/KEY: CDS
<222> LOCATION: (1)...(43)

<400> SEQUENCE: 42 tct gca aac ata tca caa gaa nat cct cac tca ccc ttc gcc a    43
Ser Ala Asn Ile Ser Gln Glu Xaa Pro His Ser Pro Phe Ala
  1               5                  10

<210> SEQ ID NO 43
<211> LENGTH: 14
<212> TYPE: PRT
<213> ORGANISM: Homo Sapiens
<220> FEATURE:
<221> NAME/KEY: Unknown
<222> LOCATION: (8)...(8)
<223> OTHER INFORMATION: Xaa = any amino acid

<400> SEQUENCE: 43

```
Ser Ala Asn Ile Ser Gln Glu Xaa Pro His Ser Pro Phe Ala
1               5                   10
```

<210> SEQ ID NO 44
<211> LENGTH: 43
<212> TYPE: DNA
<213> ORGANISM: Homo Sapiens
<220> FEATURE:
<221> NAME/KEY: Unknown
<222> LOCATION: (22)...(22)
<223> OTHER INFORMATION: n = A or T or C or G or other
<221> NAME/KEY: CDS
<222> LOCATION: (1)...(43)

<400> SEQUENCE: 44

```
tct gca aac ata tca caa gaa ngg cga gag atg gtg ggg ccc a        43
Ser Ala Asn Ile Ser Gln Glu Xaa Arg Glu Met Val Gly Pro
1               5                   10
```

<210> SEQ ID NO 45
<211> LENGTH: 14
<212> TYPE: PRT
<213> ORGANISM: Homo Sapiens
<220> FEATURE:
<221> NAME/KEY: Unknown
<222> LOCATION: (8)...(8)
<223> OTHER INFORMATION: Xaa = any amino acid

<400> SEQUENCE: 45

```
Ser Ala Asn Ile Ser Gln Glu Xaa Arg Glu Met Val Gly Pro
1               5                   10
```

<210> SEQ ID NO 46
<211> LENGTH: 43
<212> TYPE: DNA
<213> ORGANISM: Homo Sapiens
<220> FEATURE:
<221> NAME/KEY: Unknown
<222> LOCATION: (22)...(22)
<223> OTHER INFORMATION: n = a or T or C or G or other
<221> NAME/KEY: CDS
<222> LOCATION: (1)...(43)

<400> SEQUENCE: 46

```
tct gca aac ata tca caa gaa nga agt gaa tac tct ggc aat g        43
Ser Ala Asn Ile Ser Gln Glu Xaa Ser Glu Tyr Ser Gly Asn
1               5                   10
```

<210> SEQ ID NO 47
<211> LENGTH: 14
<212> TYPE: PRT
<213> ORGANISM: Homo Sapiens
<220> FEATURE:
<221> NAME/KEY: Unknown
<222> LOCATION: (8)...(8)
<223> OTHER INFORMATION: Xaa = any amino acid

<400> SEQUENCE: 47

```
Ser Ala Asn Ile Ser Gln Glu Xaa Ser Glu Tyr Ser Gly Asn
1               5                   10
```

METHOD OF IDENTIFYING PAX8-PPAR GAMMA-NUCLEIC ACID MOLECULES

PRIORITY OF THE INVENTION

This application claims priority under Title 35 §119(e), of U.S. Provisional Application No. 60/177,109, filed Jan. 20, 2000, and No. 60/225,079, filed Aug. 14, 2000, both entitled PAX8-PPARγ NUCLEIC ACID MOLECULES AND POLYPEPTIDES AND USES THEREOF, the entire contents of which are incorporated herein by reference.

FIELD OF THE INVENTION

The present invention relates to oncology and identification of oncogenes and oncoproteins useful in the diagnosis, prognosis and therapy associated with neoplasia.

BACKGROUND OF THE INVENTION

Chromosome aberrations are characteristic of human cancer and include translocations, inversions, amplifications and deletions. Chromosomal translocations often generate gene fusions (i.e., fusion oncogenes) that contribute to tumorigenesis through expression of encoded oncoproteins. Some translocations fuse (i.e., physically join) promoter sequences of one gene with coding sequences of another gene leading to overexpression of wild type proto-oncoproteins. Other translocations fuse coding sequence of two genes leading to expression of chimeric oncoproteins. Chimeric fusion oncogenes/oncoproteins are specific to tumor tissue and usually to cancer type. They reproduce many aspects of cancer in animal models and are of wide interest because they define biologic pathways important in human neoplasia and are ideal targets for diagnosis and therapy.

Translocations harboring fusion oncogenes have been observed consistently in human leukemia/lymphomas and sarcomas but not in carcinomas. In fact, most chromosome abnormalities identified in carcinomas to date have consisted of deletions involving loss of growth restraining tumor suppressor genes rather than translocations involving fusion oncogenes.

The search for mechanisms underlying cancer and oncogenesis is ongoing. Understanding tumorigenesis and the reasons for uncontrolled and/or rapid cell proliferation will help researchers and clinicians develop tools for early detection, diagnosis and aggressive treatment of neoplasias.

SUMMARY OF THE INVENTION

Carcinomas are the predominant causes of cancer morbidity and death in humans. The invention relates to novel molecular markers, screening assays and therapeutic strategies for carcinoma and provides compositions and methods for diagnosing and treating carcinomas, and in some aspects particularly thyroid follicular carcinoma. The invention is premised, in part, on the discovery that PAX8 and PPARγ genomic loci are able to translocate to form fusion nucleic acid molecules and polypeptides which comprise both PAX8 and PPARγ sequences. Thus, the invention is based in part on the finding of a fusion oncogene designated PAX8-PPARγ1 (or its reciprocal PPARγ1-PAX8) in carcinoma samples. The fusion oncogene (and its reciprocal) are the result of a chromosomal translocation fusing chromosomes 2 and 3, and herein referred to as t(2;3)(q13;p25).

According to one aspect of the invention, an isolated PAX8-PPARγ1 nucleic acid molecule is provided which comprises: (a) a nucleic acid molecule which hybridizes under stringent conditions to a nucleic acid molecule comprising a nucleotide sequence selected from the group consisting of SEQ ID NO:1, SEQ ID NO:3, SEQ ID NO:5 and SEQ ID NO:22 and which codes for a PAX8-PPARγ1 polypeptide; (b) deletions, additions and substitutions of (a) which code for a respective PAX8-PPARγ1 polypeptide; (c) a nucleic acid molecule that differs from the nucleic acid molecules of (a) or (b) in codon sequence due to the degeneracy of the genetic code; and (d) complements of (a), (b) or (c). The preferred PAX8-PPARγ1 nucleic acid molecules comprise a sequence selected from the group consisting of SEQ ID NO:1, SEQ ID NO:3, SEQ ID NO:5 and SEQ ID NO:22. In another embodiment, the invention provides isolated nucleic acid molecules which code for a polypeptide comprising an amino acid sequence selected from the group consisting of SEQ ID NO:2, SEQ ID NO:4, SEQ ID NO:6 and SEQ ID NO:23.

The invention provides similar aspects which relate to the reciprocal fusion, PPARγ1-PAX8. Thus, according to one aspect of the invention, an isolated PPARγ1-PAX8 nucleic acid molecule is provided which comprises: (a) a nucleic acid molecule which hybridizes under stringent conditions to a nucleic acid molecule comprising a nucleotide sequence selected from the group consisting of SEQ ID NO:36, SEQ ID NO:37 and SEQ ID NO:38 and which codes for a PPARγ1-PAX8 polypeptide; (b) deletions, additions and substitutions of (a) which code for a respective PPARγ1-PAX8 polypeptide; (c) a nucleic acid molecule that differs from the nucleic acid molecules of (a) or (b) in codon sequence due to the degeneracy of the genetic code; and (d) complements of (a), (b) or (c). The preferred PPARγ1-PAX8 nucleic acid molecules comprise a sequence selected from the group consisting of SEQ ID NO:36, SEQ ID NO:37 and SEQ ID NO:38. In another embodiment, the invention provides isolated nucleic acid molecules which code for a polypeptide comprising an amino acid sequence selected from the group consisting of SEQ ID NO:39, SEQ ID NO:40 and SEQ ID NO:41.

According to yet another aspect of the invention, an isolated PAX8-PPARγ1 nucleic acid molecule is provided which is selected from the group consisting of: (a) a unique fragment of a nucleic acid molecule comprising a sequence selected from the group consisting of SEQ ID NO:1, SEQ ID NO:3, SEQ ID NO:5 and SEQ ID NO:22 (of sufficient length to represent a sequence unique within the human genome); and (b) complements of (a), provided that the unique fragment includes a sequence of contiguous nucleotides which is not identical to any sequence selected from the group consisting of: (1) sequences having the database accession numbers of Table 1 (corresponding to each SEQ ID NO) or other previously published sequences as of the date of invention or the filing date of this application, (2) complements of (1), and optionally (3) fragments of (1) and (2).

According to yet another aspect of the invention, an isolated PPARγ1-PAX8 nucleic acid molecule is provided which is selected from the group consisting of: (a) a unique fragment of a nucleic acid molecule comprising a sequence selected from the group consisting of SEQ ID NO:36, SEQ ID NO:37, and SEQ ID NO:38 (of sufficient length to represent a sequence unique within the human genome); and (b) complements of (a), provided that the unique fragment includes a sequence of contiguous nucleotides which is not identical to any sequence selected from the group consisting of: (1) sequences having the database accession numbers of Table 1 (corresponding to each SEQ ID NO) or other previously published sequences as of the date of invention or the filing date of this application, (2) complements of (1), and optionally (3) fragments of (1) and (2).

In one embodiment, the sequence of contiguous nucleotides is selected such that at least one, or at least two, or at least three, or at least four or more contiguous nucleotides derive from each of the source genes (i.e., PPARγ or PAX8).

In one embodiment, the sequence of contiguous nucleotides is selected from the group consisting of (1) at least two contiguous nucleotides nonidentical to the sequence group, (2) at least three contiguous nucleotides nonidentical to the sequence group, (3) at least four contiguous nucleotides nonidentical to the sequence group, (4) at least six contiguous nucleotides nonidentical to the sequence group, (5) at least eight contiguous nucleotides nonidentical to the sequence group, and (6) at least ten contiguous nucleotides nonidentical to the sequence group.

In another embodiment, the unique fragment has a size selected from the group consisting of at least 8 nucleotides, at least 10 nucleotides, at least 12 nucleotides, at least 14 nucleotides, at least 16 nucleotides, at least 18 nucleotides, at least 20, nucleotides, at least 22 nucleotides, at least 24 nucleotides, at least 26 nucleotides, at least 28 nucleotides, at least 30 nucleotides, at least 40 nucleotides, at least 50 nucleotides, at least 75 nucleotides, at least 100 nucleotides, at least 200 nucleotides, at least 1000 nucleotides and every integer length therebetween as if fully cited herein.

In other embodiments, the unique fragment encodes a peptide which is a fragment of a polypeptide comprising an amino acid sequence selected from the group consisting of SEQ ID NO:2, SEQ ID NO:4, SEQ ID NO:6, SEQ ID NO:23 (for unique fragments of PAX8-PPARγ1) and SEQ ID NO:39, SEQ ID NO:40 and SEQ ID NO:41 (for unique fragments of PPARγ1-PAX8).

According to yet another aspect, the invention provides an isolated PAX8-PPARγ1 nucleic acid molecule comprising a sequence selected from the group consisting of SEQ ID NO:7, SEQ ID NO:9 and SEQ ID NO:11, and an isolated PPARγ1-PAX8 nucleic acid molecule comprising a sequence selected from the group consisting of SEQ ID NO:42, SEQ ID NO:44 and SEQ ID NO:46, a replicable vector comprising such nucleic acid molecules and a host cell comprising the replicable vector.

According to other aspects, the invention provides expression vectors, and host cells transformed or transfected with such expression vectors, comprising the nucleic acid molecules described above.

According to yet another aspect of the invention, an isolated PAX8-PPARγ1 polypeptide is provided. The isolated PAX8-PPARγ1 polypeptide is encoded by one or more PAX8-PPARγ1 nucleic acid molecules of the invention. Preferably, the PAX8-PPARγ1 polypeptide is a polypeptide comprising an amino acid sequence selected from the group consisting of SEQ ID NO:2, SEQ ID NO:4, SEQ ID NO:6 and SEQ ID NO:23. In some embodiments, the PAX8-PPARγ1 polypeptide comprises at least two, preferably three, and, more preferably, four or more amino acids from each of the PAX8- and PPARγ1-derived polypeptide sequences.

According to yet a further aspect of the invention, an isolated PPARγ1-PAX8 polypeptide is provided. The isolated PPARγ1-PAX8 polypeptide is encoded by one or more PPARγ1-PAX8 nucleic acid molecules of the invention. Preferably, the PPARγ1-PAX8 polypeptide is a polypeptide comprising an amino acid sequence selected from the group consisting of SEQ ID NO:39, SEQ ID NO:40 and SEQ ID NO:41. In some embodiments, the PPARγ1-PAX8 polypeptide comprises at least two, preferably three, and, more preferably, four or more amino acids from each of the PPARγ1- and PAX8-derived polypeptide sequences.

In other embodiments, an isolated peptide is provided which comprises a fragment or variant of the PAX8-PPARγ1 or PPARγ1-PAX8 polypeptides disclosed herein, of sufficient length to represent a sequence unique within the human genome, and to identify a PAX8-PPARγ1 or a PPARγ1-PAX8 polypeptide, respectively. The isolated peptide may comprise at least 6, at least 8, at least 9, at least 10, at least 11, at least 12, at least 14, at least 16, at least 18 or at least 20 contiguous amino acids having a sequence of a fragment selected from the group consisting of SEQ ID NO:2, SEQ ID NO:4, SEQ ID NO:6, SEQ ID NO:23 SEQ ID NO:39, SEQ ID NO:40 and SEQ ID NO:41. The isolated peptides may also possess at least one, at least two, at least three, at least four, or more amino acids from each source polypeptide. Isolated peptides which are immunogenic are also provided. In important embodiments, the peptides comprise an amino acid sequence selected from the group consisting of SEQ ID NO:8, SEQ ID NO:10, SEQ ID NO:12, SEQ ID NO:43, SEQ ID NO:45 and SEQ ID NO:47.

According to another aspect of the invention, a composition is provided which comprises an isolated binding agent that selectively binds to a PAX8-PPARγ1 or PPARγ1-PAX8 nucleic acid molecule or to a PAX8-PPARγ1 or PPARγ1-PAX8 polypeptide encoded by the isolated nucleic acid molecules of the invention. Such isolated binding agents include nucleic acid binding agents such as probes or primers and polypeptide binding agents such as antibodies. In one embodiment, the isolated binding agents selectively bind to a nucleic acid molecule comprising a nucleotide sequence selected from the group consisting of SEQ ID NO:1, SEQ ID NO:3, SEQ ID NO:5, SEQ ID NO:22, SEQ ID NO:36, SEQ ID NO:37 and SEQ ID NO:38 or a fragment thereof. In another embodiment, the isolated agent binds selectively to a polypeptide comprising an amino acid sequence selected from the group consisting of SEQ ID NO:2, SEQ ID NO:4, SEQ ID NO:6, SEQ ID NO:23, SEQ ID NO:39, SEQ ID NO:40 and SEQ ID NO:41 or a fragment thereof. In important embodiments, the isolated binding agent is a peptide. In a further embodiment, the peptide is an antibody or a fragment thereof (e.g., Fab, F(ab)$_2$, Fd and antibody fragments which include a CDR3 region which binds selectively to the PAX8-PPARγ1 or PPARγ1-PAX8 nucleic acid molecule or polypeptide). In even more preferred embodiments, the antibody is a humanized antibody or a chimeric antibody. The isolated binding agent may be conjugated to a detectable label. The detectable label may be selected from the group consisting of a radioactive label, an enzyme, a biotin molecule, an avidin molecule or a fluorochrome.

The isolated PAX8-PPARγ1 and PPARγ1-PAX8 nucleic acid molecules disclosed herein have various utilities, including their use as probes and primers as diagnostic reagents for identifying the presence of PAX8-PPARγ1 (or reciprocal) nucleic acid molecules in biological or other samples. As an example, the isolated PAX8-PPARγ1 nucleic acid molecules are useful in the generation of PAX8-PPARγ1 polypeptides and PAX8-PPARγ1 binding agents. PAX8-PPARγ1 binding agents, in turn, can be used as reagents in diagnostic and therapeutic assays to determine the presence and/or the levels of a PAX8-PPARγ1 nucleic acid molecule or a PAX8-PPARγ1 polypeptide in a sample. Thus, the PAX8-PPARγ1 nucleic acid molecules, polypeptides and binding agents of the invention can be used, inter alia, in the diagnosis or treatment of conditions characterized by the presence of a PAX8-PPARγ1 nucleic acid molecule or a PAX8-PPARγ1 polypeptide. In some preferred embodiments, the condition is a carcinoma. In some even more preferred embodiments, the condition is thyroid follicular carcinoma. In some embodiments, the reciprocal PPARγ1-PAX8 nucleic acid molecules and polypeptides are also useful for detection and diagnostic assays as well as in therapeutic and screening methods of the invention.

According to another aspect of the invention, a method of identifying a tumor (e.g., follicular thyroid carcinoma) is provided. The method includes obtaining a biological sample such as a tissue or a fluid from a subject and analyzing the sample for the presence of a PAX8-PPARγ1 or a PPARγ1-PAX8 nucleic acid molecule or a PAX8-PPARγ1 or a PPARγ1-PAX8 polypeptide, or unique fragments of the foregoing nucleic acid molecules and polypeptides, wherein the presence of such a nucleic acid molecule or polypeptide identifies such a tumor.

According to still another aspect of the invention, a method of identifying the presence of a PAX8-PPARγ1 or a PPARγ1-PAX8 molecule in a sample is provided. The method involves analyzing the sample for the presence of a PAX8-PPARγ1 or a PPARγ1-PAX8 nucleic acid molecule or a PAX8-PPARγ1 or a PPARγ1-PAX8 polypeptide. The method may further comprise contacting the sample with at least two nucleic acid amplification primers, wherein a first nucleic acid amplification primer is capable of hybridizing to a PAX8 nucleic acid molecule and a second nucleic acid amplification primer is capable of hybridizing to a PPARγ1 nucleic acid molecule (or if the reciprocal PPARγ1-PAX8 fusion is to be detected, wherein a first nucleic acid amplification primer is capable of hybridizing to a PPARγ1 nucleic acid molecule and a second nucleic acid amplification primer is capable of hybridizing to a PAX8 nucleic acid molecule); amplifying a primed nucleic acid molecule which hybridizes to the first and the second nucleic acid amplification primers; and detecting the presence of an amplified nucleic acid molecule in the sample. Preferably, the amplification product contains the fusion juncture.

According to yet another aspect of the invention, a method of identifying the presence of a PAX8-PPARγ1 or a PPARγ1-PAX8 nucleic acid molecule in a sample is provided. The method involves contacting the sample with at least two nucleic acid probes, wherein a first nucleic acid probe is capable of hybridizing to a PAX8 nucleic acid molecule and a second nucleic acid probe is capable of hybridizing to a PPARγ1 nucleic acid molecule (or if the reciprocal PPARγ1-PAX8 fusion is to be detected, wherein a first nucleic acid probe is capable of hybridizing to a PPARγ1 nucleic acid molecule and a second nucleic acid probe is capable of hybridizing to a PAX8 nucleic acid molecule); and detecting the presence of a nucleic acid molecule in the sample which hybridizes to both the first and the second nucleic acid probes.

According to a further aspect of the invention, a method of identifying the presence of the PAX8-PPARγ1 or a PPARγ1-PAX8 nucleic acid molecule in a sample is provided. The method involves contacting the sample with a nucleic acid probe which is capable of hybridizing to a PAX8-PPARγ1 or a PPARγ1-PAX8 fusion juncture, and detecting the presence of a nucleic acid molecule in the sample which hybridizes to the nucleic acid probe. The PAX8-PPARγ1 nucleic acid fusion juncture may comprise a sequence selected from the group consisting of SEQ ID NO:7, SEQ ID NO:9 and SEQ ID NO:11. The PPARγ1-PAX8 nucleic acid fusion juncture may comprise a sequence selected from the group consisting of SEQ ID NO:42, SEQ ID NO:44 and SEQ ID NO:46.

According to yet another aspect of the invention, a method of identifying the presence of PAX8-PPARγ1 or a PPARγ1-PAX8 polypeptide in a sample is provided. The method involves contacting the sample with at least two binding agents (e.g., antibodies), wherein a first binding agent is capable of selectively binding to a PAX8 polypeptide and a second binding agent is capable of selectively binding to a PPARγ1 polypeptide; and detecting the presence of a PAX8-PPARγ1 polypeptide in the sample which binds both the first and the second binding agents.

According to a further aspect of the invention, a method of identifying the presence of PAX8-PPARγ1 or a PPARγ1-PAX8 polypeptide in a sample is provided. The method involves contacting the sample with a binding agent (e.g., an antibody) which is capable of selectively binding to a PAX8-PPARγ1 or a PPARγ1-PAX8 polypeptide fusion juncture, and detecting the presence of a PAX8-PPARγ1 or a PPARγ1-PAX8 polypeptide in the sample which selectively binds to the binding agent.

In the foregoing embodiments, the binding agent may be an antibody or a fragment thereof.

In yet another aspect, the invention provides a method for treating a subject having a disorder characterized by the presence of a PAX8-PPARγ1 or a PPARγ1-PAX8 nucleic acid molecule. The method involves administering an agent to a subject in need of such treatment in an amount effective to treat the subject. In one embodiment, treating the subject refers to inhibiting the progression of the disorder. In important embodiments, the agent is a PPARγ ligand and the subject is not otherwise in need of PPARγ ligand treatment. The PPARγ ligand may be selected from the group consisting of 5-[4-[2-(5-ethylpyridin-2-yl)ethoxyl]benzyl]thiadiazolidine-2,4-dione: (pioglitazone); 5-[4-[(1-methylcyclohexyl)methoxy]benzyl]thiadiazolidine-2,4-dione: (ciglitazone); 5-[(2-benzyl-2,3-dihydrobenzopyran)-5-ylmethyl]thiadiazoline-2,4-dione: (englitazone); 5-[(2-alkoxy-5-pyridyl)methyl]-2,4-thiazolidinedione; 5-[(substituted-3-pyridyl)methyl]-2,4-thiazolidinedione; 5-[4-(2-methyl-2-phenylpropoxy)benzyl]thiazolidine-2,4-dione; 5-[4-[3-methyoxyphenyl)-2-oxooxazolidin-5-yl]-methoxy]benzyl-2,4-thiazo-lidinedione; 5-[4-[3-(3,4-difluorophenyl)-2-oxooxazolidin-5-yl]-methoxy]benzyl-2,4-thiazo-lidinedione; 5-[4-[3-(4-chloro-2-fluorophenyl)-2-oxooxazolidin-5-yl]methoxy]benzyl-2,4-thiazolidinedione; 5-[4-[3-(4-trifluoromethoxyphenyl)-2-oxooxazolidin-5-yl]methoxy]benzyl-2,4-thiazolidinedione; 5-[4-[3-(4-trifluoromethylphenyl)-2-oxooxazolidin-5-yl]methoxy]benzyl-2,4-thiazolidinedione; 5-[4-[2-[3-(4-trifluoromethylphenyl)-2-oxooxazolidin-5-yl]ethoxy]benzyl]-2,4-thiazolidinedione; 5-[4-[2-[3-(4-chloro-2-fluorophenyl)-2-oxooxazolidin-5-yl]ethoxy]benzyl]-2,4-thiazolidinedione; 5-[4-[3-(4-pyridyl)-2-oxooxazolidin-5-yl]methoxy]-benzyl-2,4-thiazolidinedione; 5-[[4-[(3,4-dihydro-6-hydroxy-2,5,7,8-tetramethyl-2H-1-benzopyran-2-yl)methoxy]phenyl]methyl]-2,4-thiazolidinedione: (troglitazone); 4-(2-naphthylmethyl)-1,2,3,5-oxathiadiazole-2-oxide; 5-[4-[2-[N-(benzoxazol-2-yl)-N-methylamino]ethoxy]benzyl]-5-methylthiazolidine-2,4-dione; 5-[4-[2-[2,4-dioxo-5-phenylthiazolidin-3-yl)ethoxy]benzyl]thiazolidine-2,4-dione; 5-[4-[2-[N-methyl-N-(phenoxycarbonyl)amino]ethoxy]benzyl]thiazolidine-2,4-dione; 5-[4-(2-phenoxyethoxy)benzyl]thiazolidine-2,4-dione; 5-[4-[2-(4-chlorophenyl)ethylsulfonyl]benzyl]thiazolidine-2,4-dione; 5-[4-[3-(5-methyl-2-phenyloxazol-4-yl)propionyl]benzyl]thiazolidine-2,4-dione; 5-[[4-(3-hydroxy-1-methylcyclohexyl)methoxy]benzyl]thiadiazolidine-2,4-dione; 5-[4-[2-(5-methyl-2- phenyloxazol-4-yl)ethoxyl]benzyl]thiadizolidione-2,4-dione; 5-[[2-(2-naphthylmethyl)benzoxazol]-5-ylmethyl] thiadiazoline-2,4-dione; 5-[4-[2-(3-phenylureido)ethoxyl] benzyl]thiadiazoline-2,4-dione; 5-[4-[2-[N-(benzoxazol-2-yl)-N-methylamino]ethoxy]benzyl]thiadiazoline-2,4-dione; 5-[4-[3-(5-methyl-2-phenyloxazol-4-yl)propionyl]benzyl] thiadiazoline-2,4-dione; 5-[2-(5-methyl-2-phenyloxazol-4-ylmethyl)benzofuran-5-ylmethyl]-oxazolidine-2,4-dione; 5-[4-[2-[N-methyl-N-(2-pyridyl)amino]ethoxy]benzyl] thiazolidine-2,4-dione; and 5-[4-[2-[N-(benzoxazol-2-yl)-N-methylamino]ethoxy]benzyl]-oxazolidine-2,4-dione. In preferred embodiments, the PPARγ ligand is troglitazone or pioglitazone.

In one embodiment, the disorder is cancer. In a preferred embodiment, the cancer is follicular carcinoma. The agent may be administered directly to a tissue. In one embodiment, the tissue is thyroid tissue.

According to another aspect of the invention, a pharmaceutical composition is provided which comprises a therapeutically effective amount of an isolated PAX8-PPARγ1 or a PPARγ1-PAX8 nucleic acid molecule, an isolated PAX8-PPARγ1 or a PPARγ1-PAX8 polypeptide, or an isolated PAX8-PPARγ1 or a PPARγ1-PAX8 binding agent in a pharmaceutically acceptable carrier. The pharmaceutical compositions may be useful in accordance with the therapeutic methods, including the diagnostic imaging applications, disclosed herein.

The invention also provides in another aspect a method of locating and/or visualizing cells which contain a PAX8-PPARγ1 or a PPARγ1-PAX8 polypeptide. The method involves contacting a binding agent which is capable of binding to the PAX8-PPARγ1 or the PPARγ1-PAX8 polypeptide fusion juncture and which is conjugated to a detectable label to cells containing a PAX8-PPARγ1 or a PPARγ1-PAX8 nucleic acid molecule or a PAX8-PPARγ1 or a PPARγ1-PAX8 polypeptide, and observing the locus of detectable label in the cells. In one embodiment, the contacting takes place in vivo and thus the method involves introducing (e.g., injecting) the binding agent into a subject having cells containing a PAX8-PPARγ1 or a PPARγ1-PAX8 nucleic acid molecule or a PAX8-PPARγ1 or a PPARγ1-PAX8 polypeptide, and observing the locus of detectable label in the subject. In one embodiment the binding agent is a radiolabeled antibody or radiolabeled antibody fragment which is capable of binding to the PAX8-PPARγ1 polypeptide fusion juncture and the method involves observing the locus of radioactivity in the subject.

In another aspect, a method is provided of delivering a toxic substance to a subject having cells which contain a PAX8-PPARγ1 or a PPARγ1-PAX8 polypeptide. The method involves administering a toxin-conjugated binding agent which is capable of binding to a PAX8-PPARγ1 or a PPARγ1-PAX8 polypeptide fusion juncture to the subject.

Yet another aspect of the invention provides a method of reducing expression of an PAX8-PPARγ1 or a PPARγ1-PAX8 nucleic acid molecule in a cell which contains a PAX8-PPARγ1 or a PPARγ1-PAX8 nucleic acid molecule. In some embodiments, the invention provides a method for reducing expression of an PAX8-PPARγ1 nucleic acid molecule in a cell which contains a PPARγ1-PAX8 nucleic acid molecule. The method involves introducing a PAX8-PPARγ1 or a PPARγ1-PAX8 (or in some embodiments, a PAX8 or a PPARγ1) antisense nucleic acid molecule into a cell, and allowing the PAX8-PPARγ1 or the PPARγ1-PAX8 (or the PAX8 or the PPARγ1) antisense nucleic acid molecule to hybridize to a sense PAX8-PPARγ1 or a sense PPARγ1-PAX8 nucleic acid molecule thereby inhibiting expression of the sense PAX8-PPARγ1 or the sense PPARγ1-PAX8 nucleic acid molecule.

The invention also provides a method of inhibiting production of a PAX8-PPARγ1 or a PPARγ1-PAX8 polypeptide. The method involves administering to a cell which contains a PAX8-PPARγ1 or a PPARγ1-PAX8 nucleic acid molecule a ribozyme that cleaves a PAX8-PPARγ1 or a PPARγ1-PAX8 nucleic acid molecule in an amount effective to inhibit production of the PAX8-PPARγ1 or the PPARγ1-PAX8 polypeptide. In one embodiment, the PAX8-PPARγ1 or the PPARγ1-PAX8 nucleic acid molecule is a PAX8-PPARγ1 or a PPARγ1-PAX8 mRNA nucleic acid molecule.

In another aspect, a transgenic non-human animal is provided that has somatic and germ line cells which contain a PAX8-PPARγ1 or a PPARγ1-PAX8 nucleic acid molecule. The PAX8-PPARγ1 or the PPARγ1-PAX8 nucleic acid molecule may be selected from any of the foregoing PAX8-PPARγ1 or PPARγ1-PAX8 nucleic acid molecules. Expression of the PAX8-PPARγ1 or the PPARγ1-PAX8 nucleic acid molecule results in a transgenic non-human animal having abnormal cell growth.

In yet another aspect, the invention provides a method of screening for an agent that inhibits the production of a PAX8-PPARγ1 or a PPARγ1-PAX8 polypeptide. The method involves determining the level of a PAX8-PPARγ1 or a PPARγ1-PAX8 polypeptide in the absence of an agent, determining the level of a PAX8-PPARγ1 or a PPARγ1-PAX8 polypeptide in the presence of the agent, and comparing the level of a PAX8-PPARγ1 or a PPARγ1-PAX8 polypeptide in the presence and absence of the agent. A decrease in the level of a PAX8-PPARγ1 or a PPARγ1-PAX8 polypeptide in the presence of the agent is indicative of an agent that inhibits the production of a PAX8-PPARγ1 or a PPARγ1-PAX8 polypeptide. In one embodiment, the agent inhibits transcription of a PAX8-PPARγ1 nucleic acid molecule. In one embodiment, the agent inhibits transcription of a PPARγ1-PAX8 nucleic acid molecule. In another embodiment, the agent inhibits translation of a PAX8-PPARγ1 nucleic acid molecule. In yet another embodiment, the agent inhibits translation of a PPARγ1-PAX8 nucleic acid molecule. The method may be performed in a cell free system or in a transgenic, non-human animal.

The invention further provides, in yet another aspect, a medicament and a method of making a medicament. The medicament comprises an agent and a pharmaceutically acceptable carrier. The method involves contacting an agent in a pharmaceutically acceptable carrier. The agent may be but is not limited to a PAX8-PPARγ1 or a PPARγ1-PAX8 nucleic acid molecule or a fragment thereof, a PAX8-PPARγ1 or a PPARγ1-PAX8 antisense nucleic acid molecule, a PAX8-PPARγ1 or a PPARγ1-PAX8 polypeptide or fragment thereof, a PAX8-PPARγ1 or a PPARγ1-PAX8 binding agent, and a therapeutic agent. In certain embodiments, the agent is a PPARγ ligand such as a agonist or an antagonist, provided the medicament is used, and optionally specifically formulated for use, in the treatment of disorder characterized by a PAX8-PPARγ1 or a PPARγ1-PAX8 nucleic acid molecule and/or polypeptide excluding uses of PPARγ ligands disclosed previous to the filing date of this application or the date of invention.

In summary, the invention provides isolated PAX8-PPARγ1 and PPARγ1-PAX8 nucleic acid molecules, unique fragments thereof, expression vectors containing the foregoing, and host cells containing the foregoing. The invention also provides isolated PAX8-PPARγ1 and PPARγ1-PAX8 polypeptides, Also provided are binding agents which selectively bind such nucleic acid molecules and polypeptides, and unique fragments thereof including antibodies, and pharmaceutical compositions containing any one or more of the foregoing molecules. The compositions of the invention can be used, inter alia, in the diagnosis or treatment of conditions characterized by the presence of a PAX8-PPARγ1 or a PPARγ1-PAX8 nucleic acid molecule or polypeptide.

It is to be understood that all aspects and embodiments described above for PAX8-PPARγ1 equally embrace methods and compositions comprising the PPARγ1-PAX8 nucleic acid molecule, polypeptide and unique fragments thereof.

BRIEF DESCRIPTION OF THE DRAWINGS

FIG. 4A illustrates the presence of RT-PCR products corresponding to a PAX8-PPARγ1 nucleic acid molecule in follicular carcinoma cells.

FIG. 4B illustrates immunohistochemical staining of a section of thyroid tissue with anti-PPARγ antibodies.

FIG. 4C is a summary of the results of RT-PCR and immunohistochemical staining for a variety of tissues.

Figure 1A:
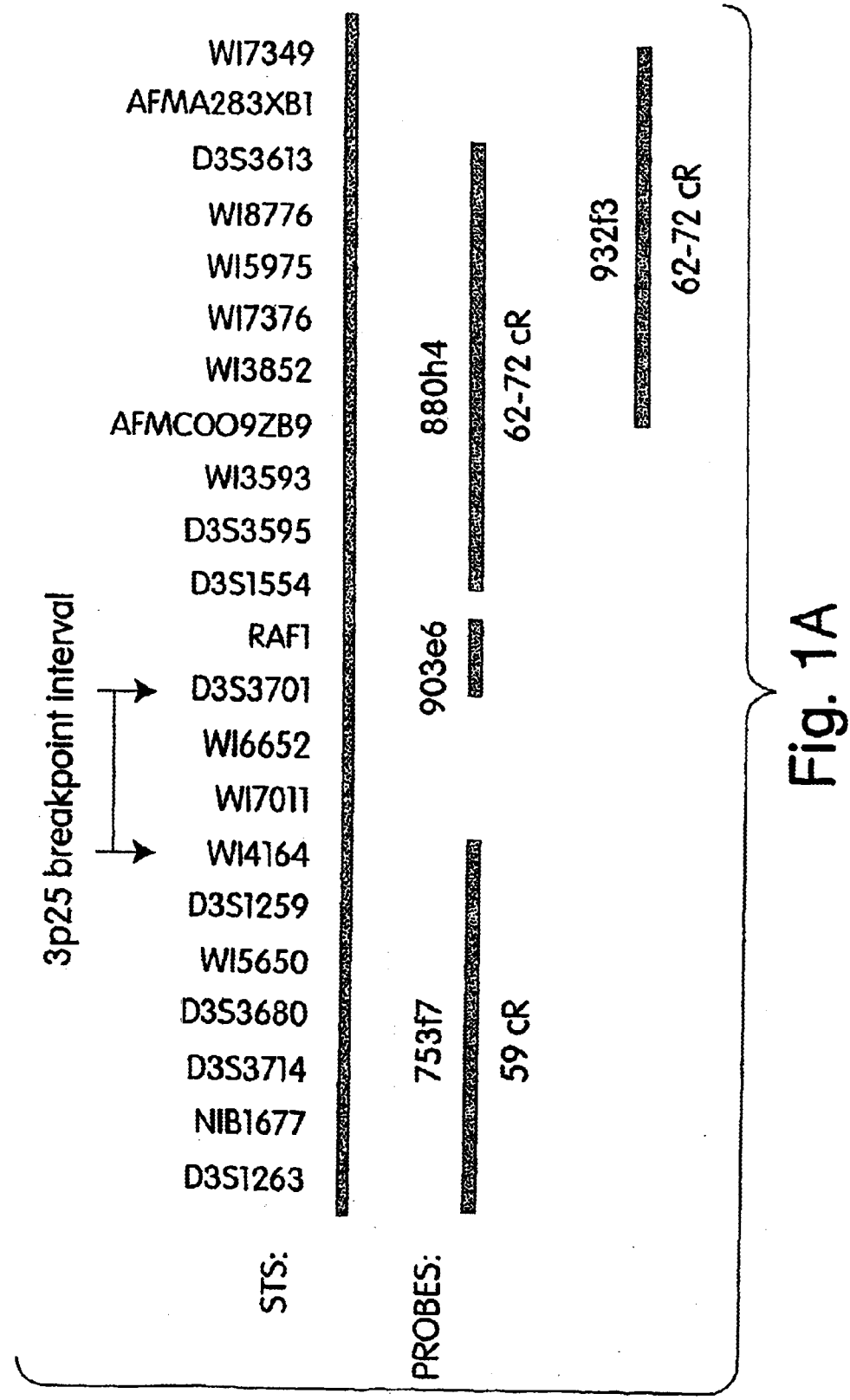
FIG. 1A is a schematic showing the location of the 3p25 breakpoint, including the PPARγ1 locus, and the hybridization pattern of probes specific for regions centromeric and telomeric to the 3p25 breakpoint.

The drawings are not required for enablement of the claimed invention.

Abbreviated Sequence Listing

SEQ ID NO:1 is the nucleotide sequence of PAX8e7-PPARγe1 cDNA.

SEQ ID NO:2 is the amino acid sequence of PAX8e7-PPARγe1 protein.

SEQ ID NO:3 is the nucleotide sequence of PAX8e8-PPARγe1 cDNA.

SEQ ID NO:4 is the amino acid sequence of PAX8e8-PPARγe1 protein.

SEQ ID NO:5 is the nucleotide sequence of PAX8e9-PPARγe1 cDNA.

SEQ ID NO:6 is the amino acid sequence of PAX8e9-PPARγe1 protein.

SEQ ID NO:7 is the nucleotide sequence including and surrounding the translocation fusion juncture 1 in the PAX8e7-PPARγe1 DNA.

SEQ ID NO:8 is the amino acid sequence including and surrounding the fusion juncture in the PAX8e7-PPARγe1 protein.

SEQ ID NO:9 is the nucleotide sequence including and surrounding the fusion juncture in the PAX8e8-PPARγe1 DNA.

SEQ ID NO:10 is the amino acid sequence including and surrounding the fusion juncture in the PAX8e8-PPARγe1 protein.

SEQ ID NO:11 is the nucleotide sequence including and surrounding the fusion juncture in the PAX8e9-PPARγe1 DNA.

SEQ ID NO:12 is the amino acid sequence including and surrounding the fusion juncture in the PAX8e9-PPARγe1 protein.

SEQ ID NO:13 is the nucleotide sequence of PAX8 cDNA (Accession No. L19606).

SEQ ID NO:14 is the amino acid sequence of PAX8 protein (Accession No. AAA03539).

SEQ ID NO:15 is the nucleotide sequence of PPARγ cDNA (Accession No. U79012).

SEQ ID NO:16 is the amino acid sequence of PPARγ protein (Accession No. AAC51248).

SEQ ID NO:17 is the nucleotide sequence of the primer L6.

SEQ ID NO:18 is the nucleotide sequence of the primer L1.

SEQ ID NO:19 is the nucleotide sequence of the primer L2.

SEQ ID NO:20 is the nucleotide sequence of the primer R1.

SEQ ID NO:21 is the nucleotide sequence of the primer R2.

SEQ ID NO:22 is the nucleotide sequence of PAX8e9(-exon 8)-PPARγe1 cDNA.

SEQ ID NO:23 is the amino acid sequence of PAX8e9 (-exon 8)-PPARγe1 protein.

SEQ ID NO:24 is the nucleotide sequence of PAX8 cDNA (Accession No. X69699).

SEQ ID NO:25 is the amino acid sequence of PAX8 protein encoded by SEQ ID NO:24.

SEQ ID NO:26 is the nucleotide sequence of PPARγ cDNA (Accession No. L40904).

SEQ ID NO:27 is the amino acid sequence of PPARγ protein (Accession No. AAA80314).

SEQ ID NO:28 is the nucleotide sequence of a 5' PAX8 primer.

SEQ ID NO:29 is the nucleotide sequence of a 5' PAX8 primer.

SEQ ID NO:30 is the nucleotide sequence of a 5' PAX8 primer.

SEQ ID NO:3 1 is the nucleotide sequence of a 3' PPARγ primer.

SEQ ID NO:32 is the nucleotide sequence of a 5' PPARγ1 primer.

SEQ ID NO:33 is the nucleotide sequence of a 5' PPARγ1primer.

SEQ ID NO:34 is the nucleotide sequence of a 3' PAX8 primer.

SEQ ID NO:35 is the nucleotide sequence of a 3' PAX8 primer.

SEQ ID NO:36 is the nucleotide sequence of a PPARγ1-PAX8 (exon 8 to end) cDNA.

SEQ ID NO:37 is the nucleotide sequence of a PPARγ1-PAX8 (exon 9 to end) cDNA.

SEQ ID NO:38 is the nucleotide sequence of a PPARγ1-PAX8 (exon 10 to end) cDNA.

SEQ ID NO:39 is the amino acid sequence of a PPARγ1-PAX8e8 cDNA.

SEQ ID NO:40 is the amino acid sequence of a PPARγ1-PAX8e9 cDNA.

SEQ ID NO:41 is the amino acid sequence of a PPARγ1-PAX8e10 cDNA.

SEQ ID NO:42 is the nucleotide sequence including and surrounding the translocation fusion juncture in the PPARγ1-PAX8e8 DNA.

SEQ ID NO:43 is the amino acid sequence including and surrounding the fusion juncture in the PPARγ1-PAX8e8 protein.

SEQ ID NO:44 is the nucleotide sequence including and surrounding the fusion juncture in the PPARγ1-PAX8e9 DNA.

SEQ ID NO:45 is the amino acid sequence including and surrounding the fusion juncture in the PPARγ1-PAX8e9 protein.

SEQ ID NO:46 is the nucleotide sequence including and surrounding the fusion juncture in the PPARγ1-PAX8e10 DNA.

SEQ ID NO:47 is the amino acid sequence including and surrounding the fusion juncture in the PPARγ1-PAX8e10 protein.

DESCRIPTION OF PREFERRED EMBODIMENTS

The present invention involves, in part, a demonstration of an oncogenic role for a translocation between a PAX8 genomic locus and a PPARγ genomic locus. The invention intends to embrace translocations between these genomic loci as diagnostic and therapeutic tools and provides specific examples of such translocations. The invention provides in part a fusion oncogene designated PAX8-PPARγ1 and its reciprocal fusion oncogene PPARγ1-PAX8. Molecular characterization of the PAX8-PPARγ1 oncogene and oncoprotein encoded thereby (and/or corresponding reciprocal fusion oncogene and oncoprotein) facilitates the identification of tumors containing the oncogene or oncoprotein. Thus, the present invention is premised, in part, on the discovery of a chromosomal translocation, t(2;3)(q13;p25), in primary carcinoma samples. The fusion oncogene is the result of a fusion of PAX8 and PPARγ genomic coding sequences.

One of the source genes contributing to the fusion oncogene, PAX8, is critical for normal development and function of the thyroid gland. The PAX8 gene maps to chromosome band 2q13. PAX8 knockout mice exhibit thyroid agenesis and lack follicular epithelial cells. PAX8 mutations have also been identified in cases of human congenital hypothyroidism. These activities of PAX8 are at least in part the result of its direct regulation of thyroid-specific genes such as thyroglobulin, thyroperoxidase, and the sodium-iodide transporter. In addition, the PAX family of transcription factors is of documented importance in tumorigenesis. Cells overexpressing individual PAX proteins develop tumors in mouse model systems, and fusion oncogenes involving PAX3 and PAX7 are central oncogenic stimuli in human alveolar rhabdomyosarcomas (i.e., cancers arising in skeletal muscle). Significantly, oncogenic alterations or mutations in PAX8 have not been identified in human cancer previously.

The other source gene contributing to the fusion oncogene, PPARγ1, is a nuclear receptor protein that regulates cell differentiation and proliferation in the fat and white blood cells lineages. The PPARγ gene maps to chromosome band 3p25. PPARγ1 function is modulated by direct binding of lipid-soluble (i.e., tissue penetrating) natural or synthetic ligands in transcription factor complexes. The PPARγ1 transcriptional complex includes in addition to PPARγ1, RXR, corepressors and coactivators. Notably, PPARγ1 has no known function in thyroid follicular epithelial cells (from which follicular carcinomas arise). It has been suggested that PPARγ1 is associated with tumor suppressor (growth inhibitory) activities in some situations.

In accordance with the present invention, an isolated PAX8-PPARγ1 nucleic acid molecule is provided. As used herein, a PAX8-PPARγ1 nucleic acid molecule refers to a nucleic acid molecule which contains, from 5' to 3', a PAX8-derived nucleotide sequence and a PPARγ-derived nucleotide sequence. The exact number of nucleotides imparted by either PAX8 or PPARγ1 to the PAX8-PPARγ nucleic acid molecule may vary, provided that the PAX8-PPARγ1 nucleic acid molecule contains a sufficient number of nucleotides from each of the respective source genes (i.e., PAX8 and PPARγ) to identify the PAX8-PPARγ1 nucleic acid molecule as a unique nucleic acid molecule derived from the fusion of these source genes. An isolated PPARγ1-PAX8 nucleic acid molecule is also provided. As used herein, a PPARγ1-PAX8 nucleic acid molecule refers to a nucleic acid molecule which contains, from 5' to 3', a PPARγ1-derived nucleotide sequence and a PAX8-derived nucleotide sequence. The exact number of nucleotides imparted by either PPARγ1 or PAX8 to the PPARγ1-PAX8 nucleic acid molecule may vary, provided that the PPARγ1-PAX8 nucleic acid molecule contains a sufficient number of nucleotides from each of the respective source genes (i.e., PPARγ and PAX8) to identify the PPARγ1-PAX8 nucleic acid molecule as a unique nucleic acid molecule derived from the fusion of these source genes.

The locus in the PAX8-PPARγ1 or the PPARγ1-PAX8 nucleic acid molecule which marks the boundary between PAX8-derived nucleotide sequence and PPARγ-derived nucleotide sequence is referred to as the "nucleic acid fusion juncture". Accordingly, the PAX8-PPARγ1 nucleic acid molecules of the invention contain a "PAX8-PPARγ1 nucleic acid fusion juncture", i.e., the minimum nucleotide sequence which identifies the PAX8-PPARγ1 nucleic acid molecule as a unique nucleic acid molecule derived from the fusion of the source genes. The PPARγ1-PAX8 nucleic acid molecules of the invention contain a "PPARγ1-PAX8 nucleic acid fusion juncture", i.e., the minimum nucleotide sequence which identifies the PPARγ1-PAX8 nucleic acid molecule as a unique nucleic acid molecule derived from the fusion of the source genes. The nucleic acid fusion juncture will comprise nucleotide sequence contributed by the PAX8 source gene as well as from the PPARγ source gene. The number of nucleotides contributed by either of the source genes may differ and may be 1, 2, 3, 4 or more nucleotides, provided the nucleic acid fusion juncture is capable of uniquely identifying a PAX8-PPARγ1 or a PPARγ1-PAX8 fusion nucleic acid molecule. PAX8-PPARγ1 and PPARγ1-PAX8 nucleic acid fusion juncture molecules may be identified in a similar manner to the identification of unique nucleic acid fragments, as described herein.

The translation product of a PAX8-PPARγ1 nucleic acid molecule is a PAX8-PPARγ1 polypeptide which similarly contains a PAX8-PPARγ1 polypeptide fusion juncture. Similarly, the translation product of a PPARγ1-PAX8 nucleic acid molecule is a PPARγ1-PAX8 polypeptide which similarly contains a PPARγ1-PAX8 polypeptide fusion juncture. A PAX8-PPARγ1 polypeptide fusion juncture refers to the minimum amino acid sequence which identifies a polypeptide as a PAX8-PPARγ1 polypeptide that includes an amino acid sequence coded for by each of the source genes. A PPARγ1-PAX8 polypeptide fusion juncture refers to the minimum amino acid sequence which identifies a polypeptide as a PPARγ1-PAX8 polypeptide that includes an amino acid sequence coded for by each of the source genes. The polypeptide fusion juncture will comprise amino acid sequence contributed by the PAX8 source gene as well as from the PPARγ source gene. The number of amino acids contributed by either of the source genes may differ and may be 1, 2, 3, 4 or more amino acids, provided the polypeptide fusion juncture is capable of uniquely identifying a PAX8-PPARγ1 or a PPARγ1-PAX8 fusion polypeptide. PAX8-PPARγ1 and PPARγ1-PAX8 fusion juncture polypeptides may be identified in a similar manner to the identification of unique polypeptide fragments, as described herein.

It was discovered in accordance with the invention that the translocation breakpoint in the PAX8 locus can occur after either exon 7, exon 8 or exon 9 of a PAX8 nucleic acid molecule (i.e., PAX8 gene). Each of these PAX8-derived nucleotide sequences can be fused to the beginning of exon 1 of a PPARγ nucleic acid molecule (i.e., PPARγ gene). As a result, several forms of PAX8-PPARγ nucleic acid molecules have been observed including PAX8e7-PPARγe1 nucleic acid molecule (having the nucleotide sequence of SEQ ID NO:1), PAX8e8-PPARγe1 nucleic acid molecule (having the nucleotide sequence of SEQ ID NO:3), PAX8e9-PPARγe1 nucleic acid molecule (having the nucleotide sequence of SEQ ID NO:5), and PAX8e9 (-exon 8)-PPARγe1 nucleic acid molecule (having the nucleotide sequence of SEQ ID NO:22). As used herein, the term PAX8-PPARγ1 nucleic acid molecule intends to embrace at least the PAX8e7-PPARγe1 nucleic acid molecule, the PAX8e8-PPARγe1 nucleic acid molecule, the PAX8e9-PPARγe1 nucleic acid molecule, and the PAX8e9 (-exon 8)-PPARγe1 nucleic acid molecule. The invention also provides a number of PAX8-PPARγ1 polypeptides corresponding to the foregoing nucleic acid molecules and these include PAX8e7-PPARγe1 polypeptide (having the amino acid sequence of SEQ ID NO:2), PAX8e8-PPARγe1 polypeptide (having the amino acid sequence of SEQ ID NO:4), PAX8e9-PPARγe1 polypeptide (having the amino acid sequence of SEQ ID NO:6), and PAX8e9 (-exon 8)-PPARγe1 polypeptide (having the amino acid sequence of SEQ ID NO:23). As used herein the term PAX8-PPARγ1 polypeptide intends to embrace at least the PAX8e7-PPARγe1 nucleic acid molecule, the PAX8e8-PPARγe1 nucleic acid molecule, the PAX8e9-PPARγe1 nucleic acid molecule, and the PAX8e9 (-exon 8)-PPARγe1 nucleic acid molecule.

Similarly, several forms of PPARγ1-PAX8 nucleic acid molecules have been observed including PPARγ1-PAX8e8 nucleic acid molecule (having the nucleotide sequence of SEQ ID NO:36), PPARγ1-PAX8e9 nucleic acid molecule (having the nucleotide sequence of SEQ ID NO:37), and PPARγ1-PAX8e10 nucleic acid molecule (having the nucleotide sequence of SEQ ID NO:38). As used herein, the term PPARγ1-PAX8 nucleic acid molecule intends to embrace at least the PPARγ1-PAX8e8 nucleic acid molecule, the PPARγ1-PAX8e9 nucleic acid molecule, and the PPARγ1-PAX8e10 nucleic acid molecule. The invention also provides a number of PPARγ1-PAX8 polypeptides corresponding to the foregoing nucleic acid molecules and these include PPARγ1-PAX8e8 polypeptide (having the amino acid sequence of SEQ ID NO:39), PPARγ1-PAX8e9 polypeptide (having the amino acid sequence of SEQ ID NO:40), and PPARγ1-PAX8e10 polypeptide (having the amino acid sequence of SEQ ID NO:41). As used herein the term PPARγ1-PAX8 polypeptide intends to embrace at least the PPARγ1-PAX8e8 nucleic acid molecule, the PPARγ1-PAX8e9 nucleic acid molecule, and the PPARγ1-PAX8e10 nucleic acid molecule.

According to one aspect of the invention, an isolated PAX8-PPARγ1 nucleic acid is provided which is selected from the following nucleic acid molecules: (a) a nucleic acid molecule which hybridizes under stringent conditions to a nucleic acid molecule comprising a nucleotide sequence selected from the group consisting of SEQ ID NO:1, SEQ ID NO:3, SEQ ID NO:5 and SEQ ID NO:22 and which codes for a PAX8-PPARγ1 polypeptide; (b) deletions, additions and substitutions of (a) which code for a respective PAX8-PPARγ1 polypeptide; (c) a nucleic acid molecule that differs from the nucleic acid molecules of (a) or (b) in codon sequence due to the degeneracy of the genetic code; and (d) complements of (a), (b) or (c).

The preferred PAX8-PPARγ1 nucleic acid molecules comprise a sequence selected from the group consisting of SEQ ID NO:1, SEQ ID NO:3, SEQ ID NO:5 or SEQ ID NO:22. The nucleic acid molecule having a nucleotide sequence of SEQ ID NO:1 encodes a PAX8-PPARγ1 polypeptide having an amino acid sequence of SEQ ID NO:2. The nucleic acid molecule having a nucleotide sequence of SEQ ID NO:3 encodes a PAX8-PPARγ1 polypeptide having an amino acid sequence of SEQ ID NO:4. The nucleic acid molecule having a nucleotide sequence of SEQ ID NO:5 encodes a PAX8-PPARγ1 polypeptide having an amino acid sequence of SEQ ID NO:6. The nucleic acid molecule having a nucleotide sequence of SEQ ID NO:22 encodes a PAX8-PPARγ1 polypeptide having an amino acid sequence of SEQ ID NO:23. The resultant PAX8-PPARγ1 polypeptides are estimated to be minimally 87–97 kDa in size. Such PAX8-PPARγ1 polypeptides comprise at least the paired and partial homeobox DNA binding domains of PAX8 fused to the DNA binding, ligand binding, RXR dimerization and transactivation domains of (i.e., domains A–F) of PPARγ1.

The nucleic acid molecule having the sequence of SEQ ID NO:1 has nucleotides 1–898 contributed by the PAX8 source gene and nucleotides 899–2334 contributed by the PPARγ source gene, and is 2334 bases in length. This nucleic acid molecule encodes a polypeptide, 777 amino acids in length, having a sequence of SEQ ID NO:2 which has amino acids 1–299 encoded by the PAX8 source gene and amino acids 300–777 encoded by the PPARγ source gene.

The nucleic acid molecule having the sequence of SEQ ID NO:3 has nucleotides 1–1087 contributed by the PAX8 source gene and nucleotides 1088–2523 contributed by the PPARγ source gene, and is 2523 bases in length. This nucleic acid molecule encodes a polypeptide, 840 amino acids in length, having a sequence of SEQ ID NO:4 which has amino acids 1–361 encoded by the PAX8 source gene and amino acids 362–840 encoded by the PPARγ source gene.

The nucleic acid molecule having the sequence of SEQ ID NO:5 has nucleotides 1–1189 contributed by the PAX8 source gene and nucleotides 1190–2625 contributed by the PPARγ source gene, and is 2625 bases in length. This nucleic acid molecule encodes a polypeptide, 874 amino acids in length, having a sequence of SEQ ID NO:6 which has amino acids 1–396 encoded by the PAX8 source gene and amino acids 397–874 encoded by the PPARγ source gene.

The nucleic acid molecule having the sequence of SEQ ID NO:22 has nucleotides 1–1207 contributed by the PAX8 source gene and nucleotides 1208–2596 contributed by the PPARγ source gene, and is 2596 bases in length. This nucleic acid molecule encodes a polypeptide, 811 amino acids in length, having a sequence of SEQ ID NO:6 which has amino acids 1–333 encoded by the PAX8 source gene and amino acids 334–811 encoded by the PPARγ source gene.

The invention similarly provides an isolated PPARγ1-PAX8 nucleic acid selected from the following nucleic acid molecules: (a) a nucleic acid molecule which hybridizes under stringent conditions to a nucleic acid molecule comprising a nucleotide sequence selected from the group consisting of SEQ ID NO:36, SEQ ID NO:37 and SEQ ID NO:38 and which codes for a PPARγ1-PAX8 polypeptide; (b) deletions, additions and substitutions of (a) which code for a respective PPARγ1-PAX8 polypeptide; (c) a nucleic acid molecule that differs from the nucleic acid molecules of (a) or (b) in codon sequence due to the degeneracy of the genetic code; and (d) complements of (a), (b) or (c).

The preferred PPARγ1-PAX8 nucleic acid molecules comprise a sequence selected from the group consisting of SEQ ID NO:36, SEQ ID NO:37, or SEQ ID NO:38. The nucleic acid molecule having a nucleotide sequence of SEQ ID NO:36 encodes a PPARγ1-PAX8 polypeptide having an amino acid sequence of SEQ ID NO:39. The nucleic acid molecule having a nucleotide sequence of SEQ ID NO:37 encodes a PPARγ1-PAX8 polypeptide having an amino acid sequence of SEQ ID NO:40. The nucleic acid molecule having a nucleotide sequence of SEQ ID NO:38 encodes a PPARγ1-PAX8 polypeptide having an amino acid sequence of SEQ ID NO:41.

Homologs and alleles of the PAX8-PPARγ1 and PPARγ1-PAX8 nucleic acid molecules of the invention can be identified by conventional techniques. Thus, an aspect of the invention is those nucleotide sequences which code for PAX8-PPARγ1 polypeptides and which hybridize to a nucleic acid molecule comprising a nucleotide sequence selected from the group consisting of SEQ ID NO:1, SEQ ID NO:3, SEQ ID NO:5 and SEQ ID NO:22 under stringent conditions. Another aspect of the invention is those nucleotide sequences which code for PPARγ1-PAX8 polypeptides and which hybridize to a nucleic acid molecule comprising a nucleotide sequence selected from the group consisting of SEQ ID NO:36, SEQ ID NO:37 and SEQ ID NO:38 under stringent conditions. The term "stringent conditions" as used herein refers to parameters with which the art is familiar.

Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrolidone, 0.02% bovine serum albumin, 2.5 mM $NaH_2PO_4$, pH 7, 0.5% SDS, 2 mM EDTA). SSC is 0.15M sodium chloride/0.15M sodium citrate, pH 7; SDS is sodium dodecyl sulphate; and EDTA is ethylenediaminetetraacetic acid. After hybridization, the membrane upon which the DNA is transferred is washed at 2×SSC at room temperature and then at 0.1×SSC/0.1% SDS at temperatures up to 68° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of the PAX8-PPARγ1 nucleic acid molecules of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 75% nucleotide identity to SEQ ID NO:1, SEQ ID NO:3, SEQ ID NO:5 or SEQ ID NO:22 (or SEQ ID NO:36, SEQ ID NO:37 or SEQ ID NO:38 for PPARγ1-PAX8 homologs and alleles) and/or at least 85% amino acid identity to SEQ ID NO:2, SEQ ID NO:4, SEQ ID NO:6 or SEQ ID NO:23 (or SEQ ID NO:39, SEQ ID NO:40 or SEQ ID NO:41, for PPARγ1-PAX8 homologs and alleles), respectively. In some instances sequences will share at least 85% nucleotide identity and/or at least 95% amino acid identity and in still other instances sequences will share at least 95% nucleotide identity and/or at least 99% amino acid identity. The homology can be calculated using various, publicly available software tools developed by NCBI (Bethesda, Md.) that can be obtained through the internet at the NCBI/NIG website. Exemplary tools include the BLAST system available on the internet at the NCBI/NIH website. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acid molecules also are embraced by the invention.

In screening for PAX8-PPARγ1 or PPARγ21-PAX8 related genes, such as homologs and alleles of PAX8-PPARγ1 or PPARγ21-PAX8 respectively, a Southern blot may be performed using the foregoing conditions, together with a radioactive probe. After washing the membrane to which the DNA is finally transferred, the membrane can be placed against X-ray film or a phosphoimager plate to detect the radioactive signal.

The invention also includes degenerate nucleic acid molecules which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into, for example, an elongating PAX8-PPARγ1 polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acid molecules that differ from the biologically isolated nucleic acid molecules in codon sequence due to the degeneracy of the genetic code.

The invention also provides isolated unique fragments of a PAX8-PPARγ1 nucleic acid molecule comprising a sequence selected from the group consisting of SEQ ID NO:1, SEQ ID NO:3, SEQ ID NO:5 and SEQ ID NO:22 (or for unique fragments of PPARγ1-PAX8: SEQ ID NO:36, SEQ ID NO:37 and SEQ ID NO:38). A unique fragment is one that is a 'signature' for the larger nucleic acid. For example, the unique fragment is long enough to assure that its precise sequence is not found in molecules within the human genome outside of the PAX8-PPARγ1 nucleic acid molecules defined above (and human alleles). Similarly, the unique fragment is long enough to assure that its precise sequence is not found in molecules within the human genome outside of the PPARγ1-PAX8 nucleic acid molecules defined above (and human alleles). Those of ordinary skill in the art may apply no more than routine procedures to determine if a fragment is unique within the human genome. The preferred unique fragments contain the PAX8-PPARγ1 or the PPARγ1-PAX8 fusion juncture. Exemplary unique fragments are represented by SEQ ID NO:7, SEQ ID NO:9, SEQ ID NO:11 SEQ ID NO:42, SEQ ID NO:44 and SEQ ID NO:46.

Accordingly, an isolated PAX8-PPARγ1 unique nucleic acid fragment is provided which is selected from the group consisting of: (a) a unique fragment of a nucleic acid molecule having a sequence selected from the group consisting of SEQ ID NO:1, SEQ ID NO:3, SEQ ID NO:5 and SEQ ID NO:22 (of sufficient length to represent a sequence unique within the human genome); and (b) complements of (a), provided that the unique fragment includes a sequence of contiguous nucleotides which excludes a sequence selected from the group consisting of: (1) sequences having the accession numbers of Table 1 (for the corresponding SEQ ID NO), or other previously published sequences as of the date of invention or the filing date of this application or a priority document, (2) complements of (1), and optionally, (3) unique fragments of (1) and (2).

In addition, an isolated PPARγ1-PAX8 unique nucleic acid fragment is provided which is selected from the group consisting of: (a) a unique fragment of a nucleic acid molecule having a sequence selected from the group consisting of SEQ ID NO:36, SEQ ID NO:37 and SEQ ID NO:38 (of sufficient length to represent a sequence unique within the human genome); and (b) complements of (a), provided that the unique fragment includes a sequence of contiguous nucleotides which excludes a sequence selected from the group consisting of: (1) sequences having the accession numbers of Table 1 (for the corresponding SEQ ID NO), or other previously published sequences as of the date of invention or the filing date of this application or a priority document, (2) complements of (1), and optionally, (3) unique fragments of (1) and (2).

In certain embodiments, the sequence of contiguous nucleotides is selected from the group consisting of (1) at least two contiguous nucleotides nonidentical to the sequence group, (2) at least three contiguous nucleotides nonidentical to the sequence group, (3) at least four contiguous nucleotides nonidentical to the sequence group, (4) at least five contiguous nucleotides nonidentical to the sequence group, (5) at least six contiguous nucleotides nonidentical to the sequence group, (6) at least seven contiguous nucleotides nonidentical to the sequence group.

In other embodiments, the unique fragment has a size selected from the group consisting of at least: 8 nucleotides, 10 nucleotides, 12 nucleotides, 14 nucleotides, 16 nucleotides, 18 nucleotides, 20, nucleotides, 22 nucleotides, 24 nucleotides, 26 nucleotides, 28 nucleotides, 30 nucleotides, 40 nucleotides, 50 nucleotides, 75 nucleotides, 100 nucleotides, 200 nucleotides, 1000 nucleotides and every integer length therebetween.

Unique fragments of PAX8-PPARγ1 or PPARγ1-PAX8 nucleic acid molecules, however, exclude fragments completely composed of sequences of PAX8 nucleic acid molecules (SEQ ID NO:13 and/or SEQ ID NO:24) or sequences of PPARγ nucleic acid molecules (SEQ ID NO:15 and/or SEQ ID NO:26). Unique fragments of PAX8-PPARγ1 or PPARγ1-PAX8 nucleic acid molecules also exclude fragments completely composed of the nucleotide sequences of a database accession number listed in Table 1 (for each corresponding SEQ ID NO), or other previously published sequences as of the date of invention or the filing date of this application.

Unique fragments can be used as probes in Southern and Northern blot assays to identify such nucleic acid molecules, or can be used in amplification assays such as those employing PCR. As known to those skilled in the art, large probes such as 200, 250, 300 or more nucleotides are preferred for certain uses such as Southern and Northern blots, while smaller fragments will be preferred for use as PCR primers. Unique fragments also can be used to generate antibodies or to determine binding of a polypeptide fragment, or to generate immunoassay components. Likewise, unique fragments can be employed to produce nonfused fragments of the PAX8-PPARγ1 or PPARγ1-PAX8 polypeptides, again useful, for example, in the preparation of antibodies, immunoassays or therapeutic applications. Unique fragments can be further used as antisense molecules to inhibit the expression of PAX8-PPARγ1 or PPARγ1-PAX8 nucleic acid molecules and polypeptides, respectively.

As will be recognized by those skilled in the art, the size of the unique fragment will depend upon its conservancy in the genetic code. Thus, some regions of SEQ ID NO:1, SEQ ID NO:3, SEQ ID NO:5 or SEQ ID NO:22 (or SEQ ID NO:36, SEQ ID NO:37 or SEQ ID NO:38) and complements thereof will require longer segments to be unique while others will require only short segments, typically between 8 and 32 nucleotides long (e.g. 8, 9, 10, 11, 12, 13, 14, 15, 16, 17, 18, 19, 20, 21, 22, 23, 24, 25, 26, 27, 28, 29, 30, 31 and 32 bases) or more, up to the entire length of the disclosed sequences. This disclosure intends to embrace each and every fragment of each PAX8-PPARγ1 nucleic acid molecule, beginning at the first nucleotide of the PAX8-contributed sequence, the second nucleotide of the PAX8-contributed sequence and so on, up to the last nucleotide of the PAX8-contributed sequence, and ending anywhere from the first nucleotide of the PPARγ1-contributed sequence, the second nucleotide of the PPARγ1-contributed sequence and so on, up to the last nucleotide of the PPARγ1-contributed sequence (provided the sequence is unique as described above). Similarly, this disclosure also intends to embrace each and every fragment of each PPARγ1-PAX8 nucleic acid molecule, beginning at the first nucleotide of the PPARγ1-contributed sequence, the second nucleotide of the PPARγ1-contributed sequence and so on, up to the last nucleotide of the PPARγ1-contributed sequence, and ending anywhere from the first nucleotide of the PAX8-contributed sequence, the second nucleotide of the PAX8-contributed sequence and so on, up to the last nucleotide of the PAX8-contributed sequence (provided the sequence is unique as described above). Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

According to another aspect of the invention, expression vectors comprising the PAX8-PPARγ1 or the PPARγ1-PAX8 nucleic acid molecules disclosed herein operably joined to a promoter and host cells containing said expression vectors are provided. In certain preferred embodiments, the host cells are eukaryotic cells. As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Insertion of any of the nucleotide sequences described herein into an appropriate vector allows production of large quantities of such sequences. Indeed, vectors, methods for inserting nucleic acid molecules into vectors, and use of such vectors for production of desired nucleic acid molecules, peptides and proteins are well known to those with skill in the art. Thus, the nucleotide sequences disclosed herein can also be inserted into cloning and/or expression vectors to produce peptides and proteins according to the present invention.

Procedures and materials for preparation of replicable vectors, transformation of host cells with vectors, and host cell expression of polypeptides are described in Maniatis et al., *Molecular Cloning: A Laboratory Manual*, Cold Spring Harbor (1982) incorporated herein by reference. A replicable vector as used herein is a vector capable of being replicated and is thus useful for producing large quantities of a nucleic acid molecule of choice. Any replicable vector known to those with skill in the art may be used to clone or amplify PAX8-PPARγ1 or PPARγ1-PAX8 nucleic acid molecules and/or to produce polypeptides encoded thereby. For example, suitable vectors include plasmids, phages, cosmids and artificial chromosomes. For example, bacteriophage lambda may be a useful cloning vector. This phage can accept pieces of foreign DNA up to about 20,000 base pairs in length. The lambda phage genome is a linear double stranded DNA molecule with single stranded complementary (cohesive) ends which can hybridize with each other when inside an infected host cell. The lambda DNA is cut with a restriction endonuclease and the foreign DNA, e.g., the DNA to be cloned, is ligated to the phage DNA fragments. The resulting recombinant molecule is then packaged into infective phage particles. Host cells are infected with the phage particles containing the recombinant DNA. The phage DNA replicates in the host cell to produce many copies of the desired DNA sequence.

Cosmids are hybrid plasmid/bacteriophage vectors which can be used to clone DNA fragments of about 40,000 base pairs. Cosmids have one or more DNA sequences called "cos" sites derived from bacteriophage lambda for packaging lambda DNA into infective phage particles. Two cosmids are ligated to the DNA to be cloned. The resulting molecule is packaged into infective lambda phage particles and transfected into bacteria host cells. When the cosmids are inside the host cell they behave like plasmids and multiply under the control of a plasmid origin of replication. The origin of replication is a sequence of DNA which allows a plasmid to multiply within a host cell.

Yeast artificial chromosome vectors (YAC) are similar to plasmids but allow for the incorporation of much larger DNA sequences of about 300 kb (kilobases) to 2 Mb (megabases), with an average of approximately 700 kb. The yeast artificial chromosomes contain sequences for replication in yeast. The yeast artificial chromosome containing the DNA to be cloned is transformed into yeast cells where it replicates thereby producing many copies of the desired DNA sequence. Where phage, cosmids or yeast artificial chromosomes are employed as cloning vectors, expression of the fusion protein or PPARγ may be obtained by culturing host cells that have been transfected or transformed with the cloning vector in a suitable culture medium. The bacterial artificial chromosomes used herein allow for the incorporation of 50–300 kb of DNA sequences.

Suitable host/vector systems are available for propagation of nucleotide sequences and the expression of peptides and proteins. Replicable plasmids, viral vectors, and host cells such as CHO, COS, insect, yeast and bacterial are well-known for use in genetic engineering and can be used herein.

As used herein with respect to nucleic acid molecules, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleotide sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein with respect to polypeptides (discussed below), the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, or (iii) for sequencing, etc.

As mentioned above, the invention embraces antisense oligonucleotides that selectively bind to a nucleic acid molecule encoding a PAX8-PPARγ1 polypeptide, to decrease PAX8-PPARγ1 expression and activity, as well as antisense oligonucleotides that selectively bind to a nucleic acid molecule encoding a PPARγ1-PAX8 polypeptide, to decrease PPARγ1-PAX8 expression and activity.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Antisense oligonucleotides that selectively bind to either PAX8-PPARγ1 or to PPARγ1-PAX8 nucleic acid molecules are particularly preferred. Even more preferred are those antisense oligonucleotides that selectively bind to the PAX8-PPARγ1 nucleic acid fusion juncture or to the PPARγ1-PAX8 nucleic acid fusion juncture. Those skilled in the art will recognize that the exact length of the antisense oligonucleotide and its degree of complementarity with its target will depend upon the specific target selected, including the sequence of the target and the particular bases which comprise that sequence.

It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1, SEQ ID NO:3, SEQ ID NO:5 or SEQ ID NO:22 (or SEQ ID NO:36, SEQ ID NO:37 or SEQ ID NO:38) or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least about 10 and, more preferably, at least about 15 consecutive bases which are complementary to the target, although in certain cases modified oligonucleotides as short as 7 bases in length have been used successfully as antisense oligonucleotides. See Wagner et al., *Nat. Med.* 1(11):1116–1118, 1995. Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind.

Finally, although SEQ ID NO:1, SEQ ID NO:3, SEQ ID NO:5 and SEQ ID NO:22 (and SEQ ID NO:36, SEQ ID NO:37 and SEQ ID NO:38) disclose cDNA sequences, one of ordinary skill in the art may easily derive the genomic DNA corresponding to each sequence. Thus, the present invention also provides for antisense oligonucleotides which are complementary to the genomic DNA corresponding to SEQ ID NO:1, SEQ ID NO:3, SEQ ID NO:5 and/or SEQ ID NO:22 (and SEQ ID NO:36, SEQ ID NO:37 and SEQ ID NO:38). Similarly, antisense to allelic or homologous PAX8-PPARγ1 and PPARγ1-PAX8 cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acid molecules has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides. The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose.

The present invention, thus, contemplates pharmaceutical preparations containing modified antisense molecules that are complementary to and hybridizable with, under physiological conditions, nucleic acid molecules encoding PAX8-PPARγ1 polypeptides, or nucleic acid molecules encoding PPARγ1-PAX8 polypeptides together with pharmaceutically acceptable carriers. Antisense oligonucleotides may be administered as part of a pharmaceutical composition. In this latter embodiment, it is preferable that a slow intravenous administration be used. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

According to yet another aspect of the invention, an isolated PAX8-PPARγ1 or PPARγ1-PAX8 polypeptide is provided. The isolated PAX8-PPARγ1 polypeptide is encoded by one or more PAX8-PPARγ1 nucleic acid molecules of the invention, while the isolated PPARγ1-PAX8 polypeptide is encoded by one or more or by one of more PPARγ1-PAX8 nucleic acids of the invention. Preferably, the isolated PAX8-PPARγ1 polypeptides of the invention are encoded by a nucleic acid molecule comprising a nucleotide sequence selected from the group consisting of SEQ ID NO:1, SEQ ID NO:3, SEQ ID NO:5 and SEQ ID NO:22 and unique fragments thereof containing the PAX8-PPARγ1 nucleic acid fusion juncture. Preferably, the isolated PPARγ1-PAX8 polypeptides of the invention are encoded by a nucleic acid molecule comprising a nucleotide sequence selected from the group consisting of SEQ ID NO:36, SEQ ID NO:37 and SEQ ID NO:38 and unique fragments thereof containing the PPARγ1-PAX8 nucleic acid fusion juncture. In yet other embodiments, the isolated PAX8-PPARγ1 polypeptides of the invention comprise an amino acid sequence selected from the group consisting of SEQ ID NO:2, SEQ ID NO:4, SEQ ID NO:6 and SEQ ID NO:23 and unique fragments thereof containing the PAX8-PPARγ1 polypeptide fusion juncture. In yet other embodiments, the isolated PPARγ1-PAX8 polypeptides of the invention comprise an amino acid sequence selected from the group consisting of SEQ ID NO:39, SEQ ID NO:40, and SEQ ID NO:41 and unique fragments thereof containing the PPARγ1-PAX8 polypeptide fusion juncture. The isolated PAX8-PPARγ1 and PPARγ1-PAX8 polypeptides are of sufficient length to represent a sequence unique within the human genome and thus distinct from either of the source polypeptides from which the fusion polypeptide derives.

In the preferred embodiments, the isolated PAX8-PPARγ1 and PPARγ1-PAX8 polypeptides are immunogenic and can be used to generate binding agents (e.g., antibodies and antibody fragments) for use in diagnostic and therapeutic applications. As diagnostic or prognostic indicators, such binding agents are useful for determining the presence or absence of a PAX8-PPARγ1 or a PPARγ1-PAX8 polypeptide, and/or for determining the level of such a polypeptide in a sample. Samples to be analyzed include but are not limited to biological samples such as biopsy samples. The PAX8-PPARγ1 and PPARγ1-PAX8 polypeptides used for generating binding agents are unique polypeptides and, therefore, the binding agents so generated are those which selectively bind to a PAX8-PPARγ1 or PPARγ1-PAX8 polypeptide and not to a PAX8 polypeptide nor a PPARγ1 polypeptide.

A unique fragment of an PAX8-PPARγ1 or a PPARγ1-PAX8 polypeptide, in general, has the features and characteristics of unique fragments as discussed above in connection with nucleic acid molecules. As will be recognized by those skilled in the art, the size of the unique fragment will depend upon factors such as whether the fragment constitutes a portion of a conserved protein domain. Thus, some regions of SEQ ID NO:2, SEQ ID NO:4, SEQ ID NO:6 or SEQ ID NO:23 (or SEQ ID NO:39, SEQ ID NO:40 or SEQ ID NO:41) will require longer segments to be unique while others will require only short segments, typically between 5 and 12 amino acids (e.g. 5, 6, 7, 8, 9, 10, 11 and 12 amino acids long or more, including each integer up to the full length, >1,000 amino acids long). Virtually any segment of SEQ ID NO:2, SEQ ID NO:4, SEQ ID NO:6 or SEQ ID NO:23 (or of SEQ ID NO:39, SEQ ID NO:40 or SEQ ID NO:41) excluding the ones that share identity with it (e.g., the PAX8 polypeptide, the PPARγ polypeptide, and fragments of the foregoing, or other polypeptides published prior to the invention or application filing date) that is 9 or more amino acids in length will be unique.

One important aspect of a unique fragment is its ability to act as a signature for identifying the polypeptide. Another is its ability to provide an immune response in an animal. Those skilled in the art are well versed in methods for selecting unique amino acid sequences, typically on the basis of the ability of the unique fragment to selectively distinguish the sequence of interest from unrelated proteins. A comparison of the sequence of the fragment to those on known databases typically is all that is necessary.

The invention embraces variants of the PAX8-PPARγ1 and PPARγ1-PAX8 polypeptides described above. As used herein, a "variant" of a PAX8-PPARγ1 polypeptide is a polypeptide which contains one or more modifications to the primary amino acid sequence of a PAX8-PPARγ1 polypeptide. Similarly, a "variant" of a PPARγ1-PAX8 polypeptide is a polypeptide which contains one or more modifications to the primary amino acid sequence of a PPARγ1-PAX8 polypeptide. Modifications which create a PAX8-PPARγ1 or a PPARγ1-PAX8 polypeptide variant are typically made to the nucleic acid which encodes the PAX8-PPARγ1 polypeptide, or to the nucleic acid which encodes the PPARγ1-PAX8 polypeptide respectively and can include deletions, point mutations, truncations, amino acid substitutions and addition of amino acids or non-amino acid moieties to: 1) reduce or eliminate a functional activity of the polypeptide, such as its ability to bind a ligand or to activate transcription of a particular genomic locus; 2) enhance a property of the polypeptide, such as protein stability in an expression system or the stability of protein-protein binding; 3) provide a novel activity or property to the polypeptide, such as addition of an antigenic epitope or addition of a detectable moiety; or 4) to provide equivalent or better binding to the polypeptide by another molecule, or to another molecule by the polypeptide.

Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the PAX8-PPARγ1 amino acid sequence, or all or part of the PPARγ1-PAX8 amino acid sequence. One of skill in the art will be familiar with methods for predicting the effect on protein conformation of a change in protein sequence, and can thus "design" a variant PAX8-PPARγ1 or a PPARγ1-PAX8 polypeptide according to known methods. One example of such a method is described by Dahiyat and Mayo in *Science* 278:82–87, 1997, whereby proteins can be designed de novo. The method can be applied to a known protein to vary only a portion of the polypeptide sequence. By applying the computational methods of Dahiyat and Mayo, specific variants of a PAX8-PPARγ1 or a PPARγ1-PAX8 polypeptide can be proposed and tested to determine whether the variant retains a desired conformation.

Variants can include PAX8-PPARγ1 polypeptides or PPARγ1-PAX8 polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a PAX8-PPARγ1 polypeptide or a PPARγ1-PAX8 polypeptide by eliminating proteolysis by proteases in an expression system.

Mutations of a nucleic acid molecule which encodes a PAX8-PPARγ1 polypeptide or of a nucleic acid molecule which encodes a PPARγ1-PAX8 polypeptide preferably preserve the amino acid reading frame of the coding sequence and, preferably, do not create regions in the nucleic acid molecule which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant PAX8-PPARγ1 or PPARγ1-PAX8 polypeptides) which are silent as to the amino acid sequence of the polypeptide, but which provide preferred codons for translation in a particular host. Still other mutations can be made to the noncoding sequences of a PAX8-PPARγ1 or PPARγ1-PAX8 gene or cDNA clone to enhance expression of the polypeptide.

The skilled artisan will realize that conservative amino acid substitutions may be made in PAX8-PPARγ1 or PPARγ1-PAX8 polypeptides to provide functionally equivalent variants of the foregoing polypeptides, i.e., the variants retain the functional capabilities of the PAX8-PPARγ1 polypeptides or of the PPARγ1-PAX8 polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the PAX8-PPARγ1 polypeptides include conservative amino acid substitutions of SEQ ID NO:2, SEQ ID NO:4, SEQ ID NO:5 or SEQ ID NO:23. Exemplary functionally equivalent variants of the PPARγ1-PAX8 polypeptides include conservative amino acid substitutions of SEQ ID NO:39, SEQ ID NO:40 or SEQ ID NO 41. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus functionally equivalent variants of PAX8-PPARγ1 polypeptides, i.e., variants of PAX8-PPARγ1 polypeptides which retain the function of the natural PAX8-PPARγ1 polypeptides, are contemplated by the invention. Conservative amino-acid substitutions in the amino acid sequence of PAX8-PPARγ1 polypeptides to produce functionally equivalent variants of PAX8-PPARγ1 polypeptides typically are made by alteration of nucleic acid sequences (e.g., SEQ ID NO:1, SEQ ID NO:3, SEQ ID NO:5 or SEQ ID NO:22) encoding PAX8-PPARγ1 polypeptides (e.g., SEQ ID NO:2, SEQ ID NO:4, SEQ ID NO:6 or SEQ ID NO:23). Functionally equivalent variants of PPARγ1-PAX8 polypeptides, i.e., variants of PPARγ1-PAX8 polypeptides which retain the function of the natural PPARγ1-PAX8 polypeptides, are contemplated by the invention. Conservative amino-acid substitutions in the amino acid sequence of PPARγ1-PAX8 polypeptides to produce functionally equivalent variants of PPARγ1-PAX8 polypeptides typically are made by alteration of nucleic acid sequences (e.g., SEQ ID NO:36, SEQ ID NO:37 or SEQ ID NO:38) encoding PPARγ1-PAX8 polypeptides (e.g., SEQ ID NO:39, SEQ ID NO:40 or SEQ ID NO:41). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a PAX8-PPARγ1 polypeptide. The activity of functionally equivalent fragments of PAX8-PPARγ1 polypeptides can be tested by cloning the gene encoding the altered PAX8-PPARγ1 polypeptide into a bacterial or mammalian expression vector, introducing the vector into an appropriate host cell, expressing the altered PAX8-PPARγ1 polypeptide, and testing for a functional capability of the PAX8-PPARγ1 polypeptides as disclosed herein. The activity of functionally equivalent fragments of PPARγ1-PAX8 can be similarly tested using PPARγ1-PAX8 nucleic acid molecules.

The PAX8-PPARγ1 and PPARγ1-PAX8 polypeptides may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of PAX8-PPARγ1 (or PPARγ1-PAX8) mRNA in cell-free extracts such as the reticulocyte lysate system also may be used to produce PAX8-PPARγ1 (or PPARγ1-PAX8) polypeptides. Those skilled in the art also can readily follow known methods for isolating PAX8-PPARγ1 or PPARγ1-PAX8 polypeptides. These include, but are not limited to, immunochromatography, HPLC, size-exclusion chromatography, ion-exchange chromatography and immune-affinity chromatography.

According to another aspect of the invention, isolated PAX8-PPARγ1 binding agents (e.g., binding nucleic acid molecules such as probes or primers, and binding polypeptides such as antibodies) which selectively bind to a PAX8-PPARγ1 nucleic acid molecule or to a PAX8-PPARγ1 polypeptide encoded by the isolated nucleic acid molecules of the invention are provided. Preferably, the isolated binding agents selectively bind to a nucleic acid molecule comprising a nucleotide sequence selected from the group consisting of SEQ ID NO:1, SEQ ID NO:3, SEQ ID NO:5 and SEQ ID NO:22; or to a polypeptide comprising an amino acid sequence selected from the group consisting of SEQ ID NO:2, SEQ ID NO:4, SEQ ID NO:6 and SEQ ID NO:23, or to unique fragments of the foregoing nucleic acid molecules and polypeptides. Also provided are isolated PPARγ1-PAX8 binding agents (e.g., binding nucleic acid molecules such as probes or primers, and binding polypeptides such as antibodies) which selectively bind to a PPARγ1-PAX8 nucleic acid molecule or to a PPARγ1-PAX8 polypeptide encoded by the isolated nucleic acid molecules of the invention are provided. Preferably, the isolated binding agents selectively bind to a nucleic acid molecule comprising a nucleotide sequence selected from the group consisting of SEQ ID NO:36, SEQ ID NO:37 and SEQ ID NO:38; or to a polypeptide comprising an amino acid sequence selected from the group consisting of SEQ ID NO:39, SEQ ID NO:40 and SEQ ID NO:41, or to unique fragments of the foregoing nucleic acid molecules and polypeptides. In the preferred embodiments, the isolated binding polypeptides include antibodies and fragments of antibodies (e.g., Fab, F(ab)$_2$, Fd and antibody fragments which include a CDR3 region which binds selectively to a PAX8-PPARγ1 or a PPARγ1-PAX8 nucleic acid molecule or polypeptide). Preferably, the antibodies for human therapeutic applications are human antibodies.

As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves binding agents in the form of binding polypeptides of numerous size and type that bind selectively to PAX8-PPARγ1 or to PPARγ1-PAX8 polypeptides, and complexes containing PAX8-PPARγ1 or PPARγ1-PAX8 polypeptides. These binding polypeptides also may be derived from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array.

One then can select phage-bearing inserts which bind to the PAX8-PPARγ1 or PPARγ1-PAX8 polypeptide or a complex containing a PAX8-PPARγ1 or a PPARγ1-PAX8 polypeptide, but not to a PAX8 polypeptide or a PPARγ polypeptide. This process can be repeated through several cycles of reselection of phage that bind to the PAX8-PPARγ1 or PPARγ1-PAX8 polypeptide or to a complex containing a PAX8-PPARγ1 or a PPARγ1-PAX8 polypeptide. Repeated rounds lead to enrichment of phage bearing particular sequences. DNA sequence analysis can be conducted to identify the sequences of the expressed polypeptides. The minimal linear portion of the sequence that binds to the PAX8-PPARγ1 or PPARγ1-PAX8 polypeptide or complex can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the PAX8-PPARγ1 polypeptides or to the PPARγ1-PAX8 polypeptides. Thus, the PAX8-PPARγ1 polypeptides of the invention, or a unique fragment thereof, or complexes of PAX8-PPARγ1 can be used to screen peptide libraries, including phage display libraries, to identify and select peptide binding polypeptides that selectively bind to the PAX8-PPARγ1 polypeptides of the invention. Similarly, the PPARγ1-PAX8 polypeptides of the invention, or a unique fragment thereof, or complexes of PPARγ1-PAX8 can be used to screen peptide libraries, including phage display libraries, to identify and select peptide binding polypeptides that selectively bind to the PPARγ1-PAX8 polypeptides of the invention. Such molecules can be used, as described, for screening assays, for purification protocols, for interfering directly with the functioning of PAX8-PPARγ1 or PPARγ1-PAX8 and for other purposes that will be apparent to those of ordinary skill in the art. In addition, such molecules can also be tested for their ability to inhibit PAX8-PPARγ1 or PPARγ1-PAX8 polypeptide production. Such inhibition can result from interference with transcription and/or translation of PAX8-PPARγ1 or PPARγ1-PAX8 nucleic acid molecules. Compounds and libraries can be so tested for these abilities using screening assays such as those described below.

A PAX8-PPARγ1 or PPARγ1-PAX8 polypeptide, or a unique fragment thereof, also can be used to isolate naturally occurring, polypeptide binding agents which may associate with the PAX8-PPARγ1 or PPARγ1-PAX8 polypeptide, respectively, in a cell. Isolation of binding agents may be performed according to well-known methods. For example, isolated PAX8-PPARγ1 polypeptides can be attached to a substrate, and then a solution suspected of containing an PAX8-PPARγ1 binding agent may be applied to the substrate. If the binding agent for PAX8-PPARγ1 polypeptides is present in the solution, then it will bind to the substrate-bound PAX8-PPARγ1 polypeptide. The binding agent then may be isolated. Other proteins which are binding agents for PAX8-PPARγ1 may be isolated by similar methods without undue experimentation.

The isolated nucleic acid molecules disclosed herein have various utilities, including their use as probes and primers in diagnostic assays for identifying the presence of PAX8-PPARγ1 or PPARγ1-PAX8 nucleic acid molecules in a sample. Additionally they may function as agents for generating PAX8-PPARγ1 or PPARγ1-PAX8 polypeptides and PAX8-PPARγ1 or PPARγ1-PAX8 binding agents that also can be used in diagnostic and therapeutic assays to determine the presence or absence of a PAX8-PPARγ1 or PPARγ1-PAX8 molecule and/or to determine the level of a PAX8-PPARγ1 or PPARγ1-PAX8 molecule in a sample. Thus, the foregoing PAX8-PPARγ1 or PPARγ1-PAX8 nucleic acid molecules, polypeptides and binding agents can be used, inter alia, in the diagnosis or treatment of conditions characterized by the expression or presence of a PAX8-PPARγ1 or PPARγ1-PAX8 nucleic acid molecule or polypeptide (See, for example, Examples).

It is to be understood that the invention intends to provide aspects similar to those described herein but wherein the PPARγ1-PAX8 nucleic acid molecule or polypeptide are used.

Since, as demonstrated herein, the PAX8-PPARγ1 and PPARγ1-PAX8 nucleic acid molecule and polypeptide is found in malignant tissue, the oncogenic role of PAX8-PPARγ1 molecules and its reciprocal is clear. Without wishing to be bound by any particular theory, there are several mechanisms by which, for example, the PAX8-PPARγ1 oncoprotein may mediate transformation. One potential mechanism may stem from the fact that the DNA binding domain of PAX8 is juxtaposed to the PPARγ DNA binding, transactivation, ligand binding, and RXR dimerization domains. The PAX8-PPARγ1 polypeptide may permit pathological recruitment of the transcriptional regulators to various genomic loci other than those normally targeted by either PAX8 or PPARγ. Alternatively, the PAX8-PPARγ polypeptide may target the same loci as PAX8 or PPARγ, but the level of transcription from these loci may be reduced or enhanced relative to normal. Still another possibility is that PAX8-PPARγ1 is able to interact with wild-type cellular polypeptides and such interaction precludes the normal function of these wild-type cellular polypeptides. (See, for example, Examples) As a result of this latter mechanism, the wild-type polypeptides may be unable to stimulate transcription, for example. As an example of this latter embodiment, normally activated PAX8 gene targets may not be transcribed in the presence of PAX8-PPARγ1. Thus, inhibition of PAX8-PPARγ1 may relieve a transcriptional block.

The invention also provides methods of treating a subject having a disorder characterized by a PAX8-PPARγ1 or a PPARγ1-PAX8 chromosomal translocation by administering to the subject an agent in an amount effective to treat the subject, as well as screening methods for the identification of such agents. The disorder in some aspects is a carcinoma while in others it is specifically thyroid follicular carcinoma. As used herein treatment of a subject includes the prophylactic treatment of a subject at risk of developing a disorder associated with a PAX8-PPARγ1 or a PPARγ1-PAX8 chromosomal translocation, as well as treatment of subjects suspected of having a disorder or known to have a disorder associated with, or characterized by, a PAX8-PPARγ1 or a PPARγ1-PAX8 chromosomal translocation. As used in these particular embodiments, the amount effective to treat the subject is the amount which inhibits either the development or the progression of a disorder or decreases the rate of progression of a disorder associated with a PAX8-PPARγ1 or a PPARγ1-PAX8 chromosomal translocation. In some instances, the disorder is a proliferative disorder. The disorder may be a tumor. Thus, alternatively an effective amount is that amount which inhibits the growth and/or proliferation of a cell having a PAX8-PPARγ1 or a PPARγ1-PAX8 chromosomal translocation. Agents which are useful in this regard include but are not limited to agents which bind specifically to the PAX8-PPARγ1 or a PPARγ1-PAX8 fusion nucleic acid molecule and thereby prevent replication, transcription and/or translation thereof, agents which bind specifically to the PAX8-PPARγ1 or a PPARγ1-PAX8 polypeptide and thereby interfere or, in other instances, promote the association of the polypeptide with other polypeptides or nucleic acid molecules in the cell. For example, the agent may be capable of interfering with nucleic acid binding by the fusion polypeptide. Alternatively, the agent may be capable of promoting nucleic acid binding by either or both of the DNA binding domains present in the fusion polypeptide. If the disorder to be treated is condition characterized by the presence of a PPARγ-responsive hyperproliferative cell, PPARγ ligands are not preferred as agents in these treatment methods.

The treatment methods described herein include prophylactic treatment. The prophylactic method may further comprise, in another embodiment, the selection of a subject at risk of developing a disorder prior to the administration of the agent. Such a subject may be identified using the diagnostic methods provided herein. Namely, a subject at risk may be one who exhibits an abnormal level of PPARγ expression products (such as mRNA molecules or polypeptides) or one who exhibits a PAX8-PPARγ1 or a PPARγ1-PAX8 nucleic acid molecule or a polypeptide in the absence of a detectable carcinoma. Other subjects at risk of developing such a disorder may be those with a family history of such disorders. As an example, subjects with a family history of thyroid carcinoma may be considered subjects for prophylactic treatment.

The invention further provides another method for treating a subject having a disorder characterized by the presence of a PAX8-PPARγ1 or a PPARγ1-PAX8 nucleic acid molecule. The method involves administering a PPARγ ligand to a subject in need of such treatment in an amount effective to treat the subject provided the subject is not otherwise in need of PPARγ ligand treatment. As used herein, an amount effective to treat the subject is that amount effective to cause a medically desirable affect. For example, an effective amount may be that amount necessary to prevent or halt the progression of the disorder.

A subject who is not otherwise in need of PPARγ ligand treatment is a subject who has not been diagnosed with carcinoma, sarcoma or leukemia and/or who lacks symptoms relating to carcinoma, sarcoma or leukemia. For the purpose of this latter embodiment, a subject not otherwise in need of treatment with a PPARγ ligand is also one who does not have and/or has not been diagnosed with a condition characterized by the presence of a PPARγ-responsive hyperproliferative cell. In addition, a subject not otherwise in need of PPARγ ligand treatment is a subject who has not previously been identified in the art as requiring treatment with a PPARγ agonist. Examples of such subjects, as well as PPARγ agonists are disclosed in PCT Patent Application WO 98/25598, the entire contents of which are incorporated herein by reference.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

Other examples of carcinomas include colon carcinoma, pancreatic cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma. In a preferred embodiment, the disorder is follicular thyroid carcinoma.

PPARγ ligands useful for such treatment methods and methods of making these compounds are known. In particular examples of PPARγ agonists are disclosed in PCT publications WO 91/07107; WO 92/02520; WO 94/01433; WO 89/08651; WO 95/18533; WO 95/35108; Japanese patent publication 69383/92; and U.S. Pat. Nos. 5,902,726; 5,861,274; 5,523,314; 5,521,202; 5,510,360; 5,498,621; 5,496,621; 5,494,927; 5,480,896; 5,478,852; 5,468,762; 5,464,856; 5,457,109; 4,287,200; 4,340,605; 4,438,141; 4,444,779; 4,461,902; 4,572,912; 4,687,777; 4,703,052; 4,725,610; 4,873,255; 4,897,393; 4,897,405; 4,918,091; 4,948,900; 5,002,953; 5,061,717; 5,120,754; 5,132,317; 5,194,443; 5,223,522; 5,232,925; and 5,260,445.

Exemplary PPARγ agonists can be selected from amongst such compounds as 5-[4-[2-(5-ethylpyridin-2-yl)ethoxyl]benzyl]thiadiazolidine-2,4-dione: (pioglitazone); 5-[4-[(1-methylcyclohexyl)methoxy]benzyl]thiadiazolidine-2,4-dione: (ciglitazone); 5-[(2-benzyl-2,3-dihydrobenzopyran)-5-ylmethyl]thiadiazoline-2,4-dione: (englitazone); 5-[(2-alkoxy-5-pyridyl)methyl]-2,4-thiazolidinedione; 5-[(substituted-3-pyridyl)methyl]-2,4-thiazolidinedione; 5-[4-(2-methyl-2-phenylpropoxy)benzyl]thiazolidine-2,4-dione; 5-[4-[3-(4-methyoxyphenyl)-2-oxooxazolidin-5-yl]methoxy]benzyl-2,4-thiazo-lidinedione; 5-[4-[3-(3,4-difluorophenyl)-2-oxooxazolidin-5-yl]-methoxy]benzyl-2,4-thiazo-lidinedione; 5-[4-[3-(4-chloro-2-fluorophenyl)-2-oxooxazolidin-5-yl]methoxy]benzyl-2,4-thiazolidinedione; 5-[4-[3-(4-trifluoromethoxyphenyl)-2-oxooxazolidin-5-yl]methoxy]benzyl-2,4-thiazolidinedione; 5-[4-[3-(4-trifluoromethyphenyl)-2-oxooxazolidin-5-yl]methoxy]benzyl-2,4-thiazolidinedione; 5-[4-[2-[3-(4-trifluoromethylphenyl)-2-oxooxazolidin-5-yl]ethoxy]benzyl]-2,4-thiazolidinedione; 5-[4-[2-[3-(4-chloro-2-fluorophenyl)-2-oxooxazolidin-5-yl]ethoxy]benzyl]-2,4-thiazolidinedione; 5-[4-[3-(4-pyridyl)-2-oxooxazolidin-5-yl]methoxy]-benzyl-2,4-thiazolidinedione; 5-[[4-[(3,4-dihydro-6-hydroxy-2,5,7,8-tetramethyl-2H-1-benzopyran-2-yl)methoxy]phenyl]methyl]-2,4-thiazolidinedione: (troglitazone); 4-(2-naphthylmethyl)-1,2,3,5-oxathiadiazole-2-oxide; 5-[4-[2-[N-(benzoxazol-2-yl)-N-methylamino]ethoxy]benzyl]-5-methylthiazolidine-2,4-dione; 5-[4-[2-[2,4-dioxo-5-phenylthiazolidin-3-yl)ethoxy]benzyl]thiazolidine-2,4-dione; 5-[4-[2-[N-methyl-N-(phenoxycarbonyl)amino]ethoxy]benzyl]thiazolidine-2,4-dione; 5-[4-(2-phenoxyethoxy)benzyl]thiazolidine-2,4-dione; 5-[4-[2-(4-chlorophenyl)ethylsulfonyl]benzyl]thiazolidine-2,4-dione; 5-[4-[3-(5-methyl-2-phenyloxazol-4-yl)propionyl]benzyl]thiazolidine-2,4-dione; 5-[[4-(3-hydroxy-1-methylcyclohexyl)methoxy]benzyl]thiadiazolidine-2,4-dione; 5-[4-[2-(5-methyl-2-phenyloxazol-4-yl)ethoxyl]benzyl]thiadizolidione-2,4-dione; 5-[[2-(2-naphthylmethyl)benzoxazol]-5-ylmethyl]thiadiazoline-2,4-dione; 5-[4-[2-(3-phenylureido)ethoxyl]benzyl]thiadiazoline-2,4-dione; 5-[4-[2-[N-(benzoxazol-2-yl)-N-methylamino]ethoxy]benzyl]thiadiazoline-2,4-dione; 5-[4-[3-(5-methyl-2-phenyloxazol-4-yl)propionyl]benzyl]thiadiazoline-2,4-dione; 5-[2-(5-methyl-2-phenyloxazol-4-ylmethyl)benzofuran-5-ylmethyl]-oxazolidine-2,4-dione; 5-[4-[2-[N-methyl-N-(2-pyridyl)amino]ethoxy]benzyl]thiazolidine-2,4-dione; and 5-[4-[2-[N-(benzoxazol-2-yl)-N-methylamino]ethoxy]benzyl]-oxazolidine-2,4-dione. Preferred PPARγ ligands include troglitazone and pioglitazone.

In one aspect, the invention provides diagnostic markers for the detection of disorders characterized by a PAX8-PPARγ1 or a PPARγ1-PAX8 chromosomal translocation. Included in these disorders are carcinomas. In one important aspect, the invention provides diagnostic markers and therapeutic methods for detecting and treating thyroid follicular carcinoma.

Thyroid follicular carcinoma is the second most common cancer of the human thyroid gland. Management of thyroid follicular carcinoma is complicated in three respects. First, follicular carcinoma is difficult to diagnose because its clinico-pathologic features overlap broadly with those of benign thyroid nodules, which are present in 20–30% of adults. Secondly, its features do not reflect biologic potential on a case-by-case basis, making it impossible to predict whether a given follicular carcinoma will be indolent or metastasize. Thirdly, patients who succumb to follicular carcinoma (20%) have often become resistant to the radio-iodine used to treat invasive and metastatic disease.

As described herein, PAX8-PPARγ1 or PPARγ1-PAX8 nucleic acid molecules and polypeptides are sensitive and specific markers for discriminating follicular carcinomas from benign tumors. Because many thyroid operations are performed to exclude the possibility of malignancy, improved identification of carcinomas in pre-operative biopsies is predicted to reduce the number of thyroid surgeries, increase the percentage of malignancies resected, and reduce the overall cost of treating patients with thyroid nodules.

Since the PAX8-PPARγ1 or PPARγ1-PAX8 molecule is present in certain tumors, methods of assaying for the presence of the nucleic acid molecule (either in the form of a genomic locus, i.e., a chromosomal rearrangement, or an mRNA transcript) and/or the polypeptide it encodes can be used to identify such tumors. Detection of the PAX8-PPARγ1 or PPARγ1-PAX8 molecule in a sample may be accomplished with any technique known to those with skill in the art. Since the PAX8-PPARγ1 or PPARγ1-PAX8 nucleic acid and amino acid sequence is provided by the present invention, existing detection techniques for amplified or unamplified nucleic acid such as in situ hybridization, Southern blotting of DNA, Northern blotting of RNA and polymerase chain reaction (PCR) assays can be utilized.

Nucleic acid amplification techniques, such as PCR, may be used to increase (i.e., amplify) PAX8-PPARγ1 or PPARγ1-PAX8 nucleic acid molecules (either DNA or RNA in nature) or a fragment of such molecules. In some instances, the extent of amplification will depend upon the number of preexisting copies contained in the sample prior to manipulation. Preferably, the PAX8-PPARγ1 or the PPARγ1-PAX8 nucleic acid molecules encode all or portions of the PAX8-PPARγ1 polypeptide, or all or portions of the PPARγ1-PAX8 polypeptide, respectively. The end result of such a PCR reaction may be a detectable amount of the amplified PAX8-PPARγ1 or a PPARγ1-PAX8 product, usually in the form of a nucleic acid molecule of a given length. In a variation of this approach, the PCR product (i.e., the amplified band) is visualized through hybridization with a labeled probe, as described earlier for Southern analysis. PCR techniques are well-known and described, for example, in Alberts et al., *Molecular Biology of the Cell*, 2nd ed., pp. 269–276 (1989), incorporated herein by reference. Briefly, PCR is performed by heating the sample to separate complementary nucleic acid strands which are then annealed to complementary primer oligonucleotides which serve as primers for DNA synthesis catalyzed by polymerase enzymes between the primers. Multiple cycles of PCR provide multiple copies of the target sequence as long as the target sequence was originally present in the sample.

Thus, in one aspect, the present invention provides a method for amplifying and detecting the presence of PAX8-PPARγ1 or a PPARγ1-PAX8 nucleic acid molecule in a sample by contacting the sample with at least a first and a second nucleic acid amplification primer such that the first nucleic acid amplification primer will hybridize to the nucleotide sequence encoding the PAX8 polypeptide portion of the PAX8-PPARγ1 or the PPARγ1-PAX8 polypeptide (or a complementary sequence thereof) and the second nucleic acid amplification primer will hybridize to the nucleotide sequence encoding the PPARγ polypeptide portion of the PAX8-PPARγ1 or the PPARγ1-PAX8 polypeptide (or a complementary sequence thereof). This is followed by amplifying the primed nucleic acid molecules in the sample and detecting the presence of the amplified molecule in the sample.

In theory, any combination of nucleic acid molecules each greater than approximately 17 base pairs in length that flank the fusion juncture (i.e., the two nucleotide molecule consisting of the most 3' nucleotide contributed by the PAX8 nucleic acid molecule to the PAX8-PPARγ1 nucleic acid molecule, and the most 5' nucleotide contributed by the PPARγ nucleic acid molecule to the PAX8-PPARγ1 nucleic acid molecule, or the two nucleotide molecule consisting of the most 3' nucleotide contributed by the PPARγ nucleic acid molecule to the PPARγ1-PAX8 nucleic acid molecule, and the most 5' nucleotide contributed by the PAX8 nucleic acid molecule to the PPARγ1-PAX8 nucleic acid molecule) can serve as primers for PCR. The primers may be either DNA or RNA in nature although, usually DNA primers are preferred due to an increased stability. If the nucleic acid molecule to which the primers hybridize is RNA in nature, a first step of reverse transcription (RT) of the RNA molecule is required and the procedure is referred to as RT-PCR. RT-PCR methods are well known in the art.

Examples of amplification primers specific for PAX8 (i.e., located 5' to the fusion juncture) are L6 (SEQ ID NO:17), L1 (SEQ ID NO:18) and L2 (SEQ ID NO:19). Examples of amplification primers specific for PPARγ (i.e., located 3' to the fusion juncture) include R1 (SEQ ID NO:20) and R2 (SEQ ID NO:21). It should be understood that amplification primers may be derived from any region of the PAX8 nucleic acid sequence and any region of the PPARγ nucleic acid sequence including intronic portions of genomic DNA. The target sequence for amplification can include genomic DNA or mRNA which encode all or unique fragments of the PAX8-PPARγ1 nucleotide sequence. It is apparent to those skilled in the art that other unique fragments derived from the PAX8 and PPARγ nucleotide sequences or sequences complementary thereto can also be used as primers.

A similar approach may be taken to amplify the reciprocal gene locus or mRNA corresponding to PPARγ1-PAX8. Examples of primers specific for PPARγ1 (i.e., 5' to the fusion juncture in the PPARγ1-PAX8 nucleic acid molecule) have the following sequences: ACC CAG AAA GCG ATT CCT TCA (SEQ ID NO:32) and ATG GGT GAA ACT CTG GGA GA (SEQ ID NO:33). Examples of primers specific for PAX8 (i.e., 3' to the fusion juncture in the PPARγ1-PAX8 nucleic acid molecule) have the following sequences: TTG CTG CAG ATC CAA AAA GG (SEQ ID NO:34) and GAG CTG GAA GGG GTG GAG CTA GA (SEQ ID NO:35).

The invention further provides nucleic acid detection techniques based on hybridization of labeled probes, e.g., fluorescent in-situ hybridization (FISH), which are capable of detecting small amounts of PAX8-PPARγ1 or PPARγ1-PAX8 sequences and are extremely useful herein. The FISH assays use large human DNA clones (either BACs or YACs) that flank or cross the fusion juncture to detect t(2;3)(q13;p25) in cancer cell nuclei or metaphase spreads. Examples of clones useful in this regard to detect PAX8-PPARγ1 or PPARγ1-PAX8 nucleic acid molecules are shown in Table 2. All of the following clones are either commercially available from Research Genetics (Huntsville, Ala.) or are available from non-commercial sources such as from the Human Genome Project or CEPH in France.

TABLE 2

Mapping Clones

| Clone name | Clone type | Chromosome location |
|---|---|---|
| 732f7 | YAC | 3p25 |
| 932f3 | YAC | 3p25 |
| 908e6 | YAC | 2q13 |
| 765e4 | YAC | 2q13 |
| 989f12 | YAC | 2q13 |
| 896a8 | YAC | 2q13 |
| 110l24 | BAC | 2q13 |
| 321f13 | BAC | 3p25 |
| 321c13 | BAC | 3p25 |
| 321k13 | BAC | 3p25 |
| 335i9 | BAC | 3p25 |
| 30g23 | BAC | 3p25 |

Thus, in accordance with the present invention, the presence of a PAX8-PPARγ1 nucleic acid molecule containing a PAX8-PPARγ1 nucleic acid fusion juncture in a sample can be detected by contacting the sample with first and second nucleic acid probes wherein the first probe hybridizes to a PAX8 nucleic acid molecule comprising the sequence of SEQ ID NO:13 and/or SEQ ID NO:24 which lies 5' to the translocation breakpoint, and the second probe hybridizes to a PPARγ nucleic acid molecule comprising the sequence of SEQ ID NO:15 and/or SEQ ID NO:26 which lies 3' to the translocation breakpoint, and detecting the presence of a nucleic acid molecule within the sample that hybridizes to both the first and second probes. The presence of a PPARγ1-PAX8 nucleic acid molecule containing a PPARγ1-PAX8 nucleic acid fusion juncture in a sample can be detected by contacting the sample with first and second nucleic acid probes wherein the first probe hybridizes to a PAX8 nucleic acid molecule comprising the sequence of SEQ ID NO:13 and/or SEQ ID NO:24 which lies 3' to the translocation breakpoint, and the second probe hybridizes to a PPARγ nucleic acid molecule comprising the sequence of SEQ ID NO:15 and/or SEQ ID NO:26 which lies 5' to the translocation breakpoint, and detecting the presence of a nucleic acid molecule within the sample that hybridizes to both the first and second probes.

Alternatively, a single probe which spans the PAX8-PPARγ1 or a PPARγ1-PAX8 nucleic acid fusion juncture can be used to detect the presence of the PAX8-PPARγ1 or a PPARγ1-PAX8 nucleic acid molecule in a sample, respectively. The single probe can be any length provided it specifically hybridizes under stringent conditions to a PAX8-PPARγ1 or a PPARγ1-PAX8 nucleic acid molecule having a PAX8-PPARγ1 or a PPARγ1-PAX8 fusion juncture and not nucleic acid molecules corresponding to either source gene. The probe may be at least 6, at least 8, at least 10, at least 12, at least 14, at least 16, at least 18, at least least 22, or at least 24 nucleotides in length. Thus, the presence of PAX8-PPARγ1 or a PPARγ1-PAX8 nucleic acid molecule can be detected by contacting the sample with a nucleic acid probe which hybridizes to the nucleic acid fusion juncture of the PAX8-PPARγ1 or the PPARγ1-PAX8 nucleic acid molecule and detecting the presence of a PAX8-PPARγ1 or a PPARγ1-PAX8 nucleic acid molecule in the sample which hybridizes to the probe. Examples of probes useful in this regard include but are not limited to those comprising a nucleotide sequence of SEQ ID NO:7, SEQ ID NO:9 or SEQ ID NO:11 (or SEQ ID NO:42, SEQ ID NO:44 or SEQ ID NO:46).

In still another variation, the invention provides a method for detecting a PAX8-PPARγ1 or a PPARγ1-PAX8 nucleic acid molecule using only a probe that hybridizes to a PPARγ nucleic acid molecule comprising the sequence of SEQ ID NO:15 and/or SEQ ID NO:26 which lies 3' to the translocation breakpoint in the source gene sequence in PAX8-PPARγ1 and which lies 5' to the translocation breakpoint in the source gene sequence in PPARγ1-PAX8. The presence of a PAX8-PPARγ1 or a PPARγ1-PAX8 nucleic acid molecule will be indicated by a change in size in the nucleic acid molecule to which the probe hybridizes. As an example, a full length PPARγ nucleic acid molecule which comprises SEQ ID NO:15 or SEQ ID NO:26 is 1.6 to 1.8 kb in length, while a PAX8-PPARγ1 nucleic acid molecule which comprises SEQ ID NO:1, SEQ ID NO:3, SEQ ID NO:5 or SEQ ID NO:22 ranges in size from 2.3 kb to 3.0 kb. Thus the presence of a 2.3 to 3.0 kb band which hybridizes the foregoing probe will indicate the presence of a PAX8-PPARγ1 nucleic acid molecule. Useful probes are also those which hybridize specifically to intronic regions of the PPARγ nucleic acid molecule which are 3' of the translocation breakpoint or 5' of the breakpoint for PPARγ1-PAX8. When using intron specific probes, sizes of the detected molecules will correspond to the genomic locus sizes for the PPARγ and PAX8-PPARγ1 or PPARγ1-PAX8 nucleic acid molecules. In a similar manner, probes which hybridize specifically to a PAX8 nucleic acid molecule comprising the sequence of SEQ ID NO:13 and/or SEQ ID NO:24 which lies 5' to the translocation breakpoint (or 3' to the translocation breakpoint for PPARγ1-PAX8) can also be used. As discussed above, probes which hybridize to PAX8 intronic sequences are also useful in this method. Detection of small differences in length may require, in some instances, high agarose or polyacrylamide percentage gels in order to resolve the nucleic acid molecules.

Nucleic acid probes and primers for hybridization which are derived from PAX8-PPARγ1 or PPARγ1-PAX8 can be synthesized on an oligonucleotide synthesizer such as those commercially available from Applied Biosystems (California). DNA or RNA probes can also be derived by PCR using two primers from the PAX8-PPARγ1 or the PPARγ1-PAX8 gene.

As is well-known in the art, probes useful in detecting nucleic acid molecules can be labeled directly by attaching a label to the probe or indirectly by causing a labeled binding agent to couple to the probe after hybridization. Examples of labels include fluorochromes such as fluorescein, Texas Red(g) and green fluorescent protein, enzymes such as horse radish peroxidase and radioactive isotopes. Signal amplification systems may also be utilized herein, e.g., avidin, streptavidin and biotin complexes or antibody hapten complexes. Such methods and systems are well known and are discussed generally, e.g., in Alberts et al., *Molecular Biology of the Cell*, 2nd ed., pp. 174–193, incorporated herein by reference. The availability of different labels provides convenient techniques for determining the presence of the PAX8-PPARγ1 or a PPARγ1-PAX8 nucleic acid molecule when, e.g., a first label is conjugated to the PAX8 specific probe and a second, different label is conjugated to the PPARγ specific probe thus allowing visualization of the different colors to confirm the presence of PAX8 nucleotide sequence and PPARγ nucleotide sequence in the same nucleic acid molecule. For example, a green fluorescent protein label appears as one color and Texas Red® appears as another color when using fluorescence, microscopy, spectrophotometry, fluorescent plate readers and flow sorters. Observation of distinct colors in close proximity confirms the presence of the PAX8-PPARγ1 or a PPARγ1-PAX8 nucleic acid molecule.

In another aspect, PAX8-PPARγ1 or PPARγ1-PAX8 nucleic acid molecules and corresponding encoded polypeptides can be detected using antibodies, fragments of antibodies (embraced within the definition of antibodies, herein) and labels, and signal amplification techniques involving antibodies. Indeed, it is well-known to use immunochemical techniques to detect target nucleic acid molecules and polypeptides and such techniques are well-suited for use herein. Antibodies which are immuno reactive to PAX8-PPARγ1 or PPARγ1-PAX8 nucleic acid molecule or to the PAX8-PPARγ1 or to the PPARγ1-PAX8 polypeptide or to unique fragments of these are generated by known techniques, e.g., by immunization of animals such as mice with PAX8-PPARγ1 or PPARγ1-PAX8 nucleic acid or with PAX8-PPARγ1 or PPARγ1-PAX8 polypeptide or unique fragments thereof which include the translocation fusion juncture. Polyclonal and monoclonal antibodies may be generated using immortal cell lines for continuous production. Antibodies to PAX8-PPARγ1 or PPARγ1-PAX8 nucleic acid or to the PAX8-PPARγ1 or to the PPARγ 1-PAX8 polypeptide or to unique fragments of each which include the fusion juncture are then conjugated to labels such as those described above. Alternatively, if the so-called primary antibody is not labeled, it can be detected with a second labeled antibody which is immunoreactive with the first antibody.

Thus, PAX8-PPARγ1 or the PPARγ1-PAX8 polypeptide or fragments thereof which include the translocation fusion juncture can be detected in a sample using antibodies by contacting the sample with one antibody which binds PAX8 and another antibody which binds PPARγ and detecting the presence of protein which binds to both antibodies. Alternatively, PAX8-PPARγ1 or PPARγ1-PAX8 or unique fragments thereof which include the fusion juncture can be detected in a sample by contacting the sample with at least one antibody which binds to an epitope in or incorporating the fusion juncture and detecting the presence of proteins which bind to the antibody. Detection of such bound antibodies and proteins or peptides is accomplished by techniques well known to those skilled in the art. Use of hapten conjugates such as digoxigenin or dinitrophenyl is also well suited herein. Antibody/antigen complexes which form in response to hapten conjugates are easily detected by linking a label to the hapten or to antibodies which recognize the hapten and then observing the site of the label.

Another method for detecting PAX8-PPARγ1 or PPARγ1-PAX8 polypeptides involves the use of binding agents such as antibodies which bind specifically to regions (e.g., epitopes) of PAX8 polypeptide which are also present in PAX8-PPARγ1 or PPARγ1-PAX8 polypeptides. As an example, such an antibody would bind to an epitope composed of amino acids 1–299 of SEQ ID NO:2, 1–361 of SEQ ID NO:4, 1–396 of SEQ ID NO:6 and/or 1–333 of SEQ ID NO:23. As described for the detection of PAX8-PPARγ1 nucleic acid molecules, the presence of PAX8-PPARγ1 polypeptides would be denoted by the ability of the binding agent to bind to a polypeptide of a minimum size of 87–97 kDa. Given the amino acid sequence of PAX8, it is expected to be of a significantly lower molecular weight than the fusion polypeptides of the invention, and thus distinguishable. In a similar fashion, a binding agent that binds to a region of PPARγ polypeptide which is also present in PAX8-PPARγ1 polypeptides can also be used to detect PAX8-PPARγ1 polypeptides. One useful antibody which binds to PPARγ polypeptides is called E-8 is commercially available from Santa Cruz Biotechnology, Catalog # SC-7273.

It has also been observed according to the invention that the chromosomal translocation involving PPARγ coding sequence leads to overexpression of nucleic acid molecules which comprise PPARγ derived sequence in thyroid follicular carcinoma nuclei. The invention is also premised in part on another novel finding that normal thyroid tissue expresses PPARγ, and that in some thyroid follicular carcinoma samples the expression of normal PPARγ is upregulated. As a result, methods for determining the level of expression of PPARγ nucleic acid molecules are also embraced in the invention. Preferably, these methods are directed towards the identification and diagnosis of a thyroid follicular carcinoma. This can be detected in paraffin-embedded human thyroid tissues using a PPARγ specific binding agent such as that mentioned above.

In an additional embodiment, the invention also embraces the rearrangement and/or translocation of PPARγ coding sequences to coding sequences other than PAX8. As described in the Examples, a minority of thyroid follicular carcinoma samples demonstrated rearrangement of the PPARγ locus yet it was not possible to amplify a band from these sequences using PAX8 and PPARγ specific primers as described herein. This novel finding suggests that PPARγ is rearranged and/or potentially translocated to another coding sequence in this minority of samples. Thus the invention embraces nucleic acid molecules and polypeptides arising from rearrangements and/or chromosomal translocations involving PPARγ sequences. While not intending to be bound by any particular theory, it is possible that the PPARγ sequence in these latter samples is fused to a thyroid specific sequence.

In addition to utilizing antibodies and fragments thereof, the foregoing detection methods can also be performed using other binding agents such as those described herein including peptide and non-peptide compounds produced in libraries.

The invention also provides novel kits which could be used to measure the levels of the nucleic acid molecules of the invention, expression products of the invention or anti-PAX8-PPARγ1 or PPARγ1-PAX8 antibodies. In the case of nucleic acid detection, pairs of primers for amplifying PAX8-PPARγ1 or PPARγ1-PAX8 nucleic acid molecules can be included. The preferred kits would include controls such as known amounts of nucleic acid probes, PAX8-PPARγ1 epitopes (such as PAX8-PPARγ1 expression products) or anti-PAX8-PPARγ1 antibodies, or PPARγ1-PAX8 epitopes (such as PPARγ1-PAX8 expression products) or anti-PPARγ1-PAX8 antibodies, as well as instructions or other printed material. In certain embodiments the printed material can characterize the risk of developing a disorder that is characterized by PAX8-PPARγ1 or PPARγ1-PAX8 nucleic acid or polypeptide expression based upon the outcome of the assay. The reagents may be packaged in containers and/or coated on wells in predetermined amounts, and the kits may include standard materials such as labeled immunological reagents (such as labeled anti-IgG antibodies) and the like. One kit is a packaged polystyrene microtiter plate coated with a PAX8-PPARγ1 or a PPARγ1-PAX8 polypeptide and a container containing labeled anti-human IgG antibodies. A well of the plate is contacted with, for example, a thyroid tissue lysate, washed and then contacted with the anti-IgG antibody. The label is then detected. A kit embodying features of the present invention is comprised of the following major elements: packaging an agent of the invention, a control agent, and instructions. Packaging is a box-like structure for holding a vial (or number of vials) containing an agent of the invention. a vial (or number of vials) containing a control agent, and instructions. Individuals skilled in the art can readily modify packaging to suit individual needs.

It should be understood that kits which include reagents that are used to detect PAX8-PPARγ1 or PPARγ1-PAX8 nucleic acid molecules and polypeptides encoded thereby can also be assembled so as to provide convenient access and use in clinical settings. For example, a kit can include a container which holds one or more amplification primers, a container which holds enzymes used for amplification, a container which holds washing solution(s), a container which holds detection reagents, and a sample well. Alternatively, a kit can include a container which holds one or more antibodies directed to a PAX8 polypepticle or a fragment thereof, a container which holds one or more antibodies directed to a PPARγ polypeptide or a fragment thereof, a container which holds washing solution(s), a container which holds detection reagents, and a sample well. Alternatively, a kit may contain a container which holds one or more antibodies directed to a PAX8-PPARγ1 or a PPARγ1-PAX8 polypeptide or a fragment thereof (preferably, an antibody directed to an epitope in or including the polypeptide fusion juncture of PAX8-PPARγ1 or PPARγ1-PAX8) along with other suitable components such as washing solution and the like.

It is also contemplated that a kit may include a container having one or more labeled or unlabeled probes capable of hybridizing to the PAX8 nucleic acid molecule comprising nucleotides 1–898 of SEQ ID NO:1, 1–1087 of SEQ ID NO:3, 1–1189 of SEQ ID NO:5 or 1–1207 of SEQ ID NO:22 (depending on the form of fusion polypeptide present), a container having one or more labeled or unlabeled probes capable of hybridizing to the PPARγ nucleic acid molecule comprising nucleotides 899–2334 of SEQ ID NO:2, 1088–2523 of SEQ ID NO:4, 1190–2625 of SEQ ID NO:6 or 1208–2596 of SEQ ID NO:23 (depending on the form of fusion polypeptide present) or corresponding mRNA and, if the probe is unlabeled, a container having a labeled specific binding agent of the probe or to a recognition site on the probe, e.g., biotinylated probe, a container which holds washing solution(s), a container which holds detection reagents, and a sample well. In another embodiment, the kit comprises a single probe which is capable of hybridizing to the fusion juncture of PAX8-PPARγ1 nucleic acid molecule along with other suitable components such as washing solution and the like.

Examples of detection reagents include radiolabeled probes, enzymatic labeled probes (horse radish peroxidase, alkaline phosphatase), and affinity labeled probes (biotin, avidin, or streptavidin). For antibodies, examples of detecting reagents include, but are not limited to, labeled secondary antibodies, or, if the primary antibody is labeled, the chromophoric, enzymatic, or antibody binding reagents which are capable of reacting with the labeled antibody. The antibodies, primers and nucleic acid probes described herein can readily be incorporated into one of the established kit formats which are well known in the art.

In some instances, the foregoing detection methods and kits may also comprise a control and/or comparison with a control. As used herein, a control can include a known amount of a PAX8-PPARγ1 or a PPARγ1-PAX8 nucleic acid molecule or a fragment thereof or a PAX8-PPARγ1 or a PPARγ1-PAX8 polypeptide or a fragment thereof (such as an antigenic fragment). In preferred embodiments the control is a similar tissue sample from a subject who does not have a PAX8-PPARγ1 or a PPARγ1-PAX8 nucleic acid molecule or polypeptide or similar normal tissue from the same subject.

The methods described herein generally involve detection of a PAX8-PPARγ1 or a PPARγ1-PAX8 nucleic acid molecule or a polypeptide in a sample. Such a sample can be, but is not limited to, a tissue or a biological fluid. Tissues include brain, heart, serum, breast, colon, bladder, uterus, prostate, stomach, testis, ovary, pancreas, pituitary gland, adrenal gland, thyroid gland, salivary gland, mammary gland, kidney, liver, intestine, spleen, thymus, bone marrow, trachea, and lung. In certain embodiments, test samples originate from colon, breast and prostate tissues, and biological fluids include blood, saliva and urine. In preferred embodiments, the tissue is thyroid tissue. Both invasive and non-invasive techniques can be used to obtain such samples and are well documented in the art.

The molecular characterization of PAX8-PPARγ1 or PPARγ1-PAX8 nucleic acid molecules and the polypeptides encoded thereby allows production of therapeutic agents which selectively locate and/or destroy cells containing the PAX8-PPARγ1 or PPARγ1-PAX8 nucleic acid molecule, or its corresponding polypeptide. For example, radiolabeled antibodies or fragments of antibodies which bind to the PAX8-PPARγ1 nucleic acid molecule, or corresponding polypeptide can be contacted with cells suspected of containing a PAX8-PPARγ1 nucleic acid molecule or polypeptide. Since the radiolabeled antibodies or antibody fragments collect in the area of cells having the nucleic acid molecule, or corresponding polypeptide, such cells may be detected and localized by observing the locus of radioactivity generated by the antibodies or fragments of antibodies. In one important embodiment, the cells are contacted with the radiolabeled antibodies or fragments thereof in vivo and correspondingly, the term "contacting" in these embodiments also encompasses "injecting into a subject". Thus, in one embodiment, radiolabeled antibodies or fragments of antibodies which bind to the PAX8-PPARγ1 nucleic acid molecule, or corresponding polypeptide can be injected into a subject known to have or suspected of having a cell or a tumor containing PAX8-PPARγ1 nucleic acid molecules or corresponding polypeptides. Here, such cells or tumors may be detected and localized within a subject by observing the locus of radioactivity generated by the antibodies or fragments of antibodies. Methods of tumor localization using radiolabeled antibodies or fragments of antibodies (radioimmunodetection) are well-known in the art. See, e.g., U.S. Pat. No. 4,348,376 incorporated herein by reference. In a method similar to that described herein, other binding agents can be used for locating or visualizing cells or tumors containing PAX8-PPARγ1 or PPARγ1-PAX8 nucleic acid molecules or corresponding polypeptides. Also, detection labels other than radioactive labels may be conjugated to a binding agent and used to detect and localize cells or tumors containing PAX8-PPARγ1 or PPARγ1-PAX8 nucleic acid molecules or corresponding polypeptides. The advantage of radiolabeled binding agents is the ability to deliver radioactivity to target cells and tissues, thereby providing toxic doses of radioactivity to such cell and tissues. Preferably, the radiolabeled binding agents are those which specifically bind to the fusion nucleic acid molecule or polypeptide but not the nucleic acid molecule or polypeptide of either source gene.

Cells containing a PAX8-PPARγ1 or PPARγ1-PAX8 nucleic acid molecule or polypeptide encoded thereby may be selectively destroyed by conjugating toxins to binding agents such as antibodies or fragments of antibodies which bind to the nucleic acid molecule or polypeptide. Thus, as an example, by injecting a toxin/antibody or toxin/antibody fragment conjugate into a subject having PAX8-PPARγ1 nucleic acid molecule or polypeptide encoded thereby, wherein the antibody or antibody fragment is directed to a PAX8-PPARγ1 nucleic acid molecule or polypeptide, cells containing the nucleic acid molecule or polypeptide are preferentially destroyed by the toxin. Preferably, the binding agent in this latter embodiment is one which binds specifically to the fusion nucleic acid molecule or polypeptide and not to either of the source genes so as to reduce or prevent non-specific toxicity. In this manner, surgical resection of tumors may be avoided. Use of toxin conjugated antibodies or toxin conjugated antibody fragments is well-known in the art. See, e.g., U.S. Pat. No. 4,671,958, incorporated herein by reference. Examples of suitable toxins include those derived from diphtheria toxin, ricin and the like.

In another aspect, production of PAX8-PPARγ1 or PPARγ1-PAX8 polypeptide is inhibited by addition of antisense nucleic acid molecules (such as DNA or RNA) to cells which produce PAX8-PPARγ1 or PPARγ1-PAX8 polypeptide. In one embodiment, DNA is introduced into cells producing PAX8-PPARγ1 polypeptide, the DNA being configured to produce antisense RNA that is complementary to mRNA that encodes PAX8-PPARγ1 polypeptide. In this latter example, the antisense mRNA hybridizes with the sense mRNA transcribed from the PAX8-PPARγ1 genomic locus thereby inhibiting synthesis of PAX8-PPARγ1 polypeptide. Similar methods for using antisense molecules which hybridize to the sense mRNA transcribed from the PPARγ1-PAX8 genomic locus thereby inhibiting synthesis of PPARγ1-PAX8 are also embraced by the invention. Methods of producing antisense mRNA and use thereof for inhibition of polypeptide production are well-known in the art. Indeed, expression vectors are constructed to produce high levels of antisense RNA in transfected cells. This approach has led to reduced expression of oncogenes in exemplary instances whereby antisense oncogene constructs have reverted the growth properties of tumor cells to near normal, slowed their growth or induced apoptosis. See Watson et al., *Recombinant DNA*, 2d ed., 1992. For example, Philadelphia human chronic myelogenous leukemia (CML) cells that contain the BCR/ABL chromosomal translocation have been eradicated using antisense molecules targeted to this oncogene in clinical, pre-clinical, and laboratory settings. *J. Nat'l. Cancer Inst.* Vol. 89, No. 2, Jan. 15, 1997. A similar approach is provided herein directed to the treatment of disorders associated with the PAX8-PPARγ1 chromosomal translocation. For example, tumor cells harboring the PAX8-PPARγ1 genomic locus are treated in vivo or ex vivo with antisense molecules directed at the oncogene mRNA to induce an inhibition of cell responsiveness to tumor inducing factors, or an inhibition of factor-independent cell growth.

In another aspect, ribozymes, which are catalytic RNA sequences that cleave specific RNA molecules, are used to disrupt translation of PAX8-PPARγ1 or PPARγ1-PAX8 nucleic acid molecules. Several studies have demonstrated that ribozymes can be employed to inhibit oncogene expression, cell growth or induce apoptosis in tumor cell lines. U.S. Pat. No. 5,635,385 to Leopold, et al., incorporated herein by reference, describes a therapeutic method for the treatment of a leukemia patient resulting from a chromosomal translocation (BCR/ABL) using a ribozyme that cleaves the oncogene mRNA and inhibits the expression of the polypeptide. A similar approach is employed according to the present invention using a synthetic ribozyme targeted to the PAX8-PPARγ1 or PPARγ1-PAX8 mRNA molecules.

In yet another aspect, triplex forming oligonucleotides and RNA-DNA. hybrid technology is used to disrupt or otherwise modify the PAX8-PPARγ1 or the PPARγ1-PAX8 nucleic acid molecules. Deoxyoligonucleotides and RNA-DNA hybrids are designed to bind directly to duplex DNA in a sequence-specific manner. Once bound, they can either prevent transcription, alter a specific base sequence to correct a mutation or mutagenize a sequence to disrupt function of the gene or its regulatory elements. This has been achieved in a number of model systems. See, e.g., *J. Biol. Chem.* Vol. 271, No. 24 (1996). A similar approach is employed according to the present invention using triplex forming oligonucleotides and RNA-DNA hybrids targeted to the PAX8-PPARγ1 or to the PPARγ1-PAX8 nucleic acid molecule or its regulatory elements. For example, triplex forming oligonucleotides are designed to bind to a relatively polypurine stretch of nucleotides adjacent to the target area. The oligonucleotide is configured to serve as a carrier of DNA for the induction of recombination to insert a mutation or carry a DNA interacting agent (e.g., Mitomycin C) to directly mutagenize either the coding region or the regulatory region of the PAX8-PPARγ1 or PPARγ1-PAX8 oncogene to disable its function or induce apoptosis.

It is also contemplated that the PAX8-PPARγ1 or PPARγ1-PAX8 oncogene may be used in gene transfer studies by the transfer of the genomic DNA or cDNA of the nucleic acid molecule into target cells to serve as a transforming agent for the production of vaccines, induction of apoptosis or other indications. In one aspect, as an example, the PAX8-PPARγ1 nucleic acid molecule is delivered, for example by transfection, to nonneoplastic cells such as mesenchymal and/or epithelial cells (preferably thyroid follicular cells) and the effects of this nucleic acid molecule on the transformation of those cells is studied.

Additionally, transgenic non-human animals may be generated which contain the PAX8-PPARγ1 or the PPARγ1-PAX8 nucleic acid molecule. These animals also would be useful in studying transformation effects of PAX8-PPARγ1 or PPARγ1-PAX8 nucleic acid molecules and polypeptides. Methods of creating transgenic animals are well known in the art. For example, U.S. Pat. No. 4,873,191, incorporated herein by reference, describes genetic transformation of zygotes. Following such procedures, the PAX8-PPARγ1 and/or the PPARγ1-PAX8 nucleic acid molecule is microinjected into the nucleus of a zygote which is then allowed to undergo differentiation and development into a mature organism. Transgenic animals such as mice or pigs will have somatic and germ line cells containing the PAX8-PPARγ1 and/or the PPARγ1-PAX8 nucleic acid molecule. Such animals are useful as in vivo models for certain malignant syndromes and allow for the further development and testing of treatment modalities and screening assays for the identification of therapeutic agents. Other uses will be apparent to one of ordinary skill in the art.

As used herein, "transgenic non-human animals" include non-human animals having one or more exogenous nucleic acid molecules incorporated in germ line cells and/or somatic cells. Thus transgenic animals include "knockout" animals having a homozygous or heterozygous gene disruption by homologous recombination, animals having episomal or chromosomally incorporated expression vectors, etc. Knockout animals can be prepared by homologous recombination using embryonic stem cells as is well known in the art. The recombination may be facilitated using, for example, the cre/lox system or other recombinase systems known to one of ordinary skill in the art. In certain embodiments, the recombinase system itself is expressed conditionally, for example, in certain tissues or cell types, at certain embryonic or post-embryonic developmental stages, inducibly by the addition of a compound which increases or decreases expression, and the like. In general, the conditional expression vectors used in such systems use a variety of promoters which confer the desired gene expression pattern (e.g., temporal or spatial). Conditional promoters also can be operably linked to, for example, PAX8-PPARγ1 nucleic acid molecules to increase expression of PAX8-PPARγ1 in a regulated or conditional manner. Examples of promoters sequences which can be used to direct transcription in the thyroid tissue include promoters from genetic loci such as Pax8, thyroglobulin, thyroperoxidase, TTF-1, TTF-2, sodium-iodide symporter and TSHR. Trans-acting negative regulators of, for example, PAX8-PPARγ1 activity or expression also can be operably linked to a conditional promoter as described above. Such trans-acting regulators include antisense PAX8-PPARγ1 or PPARγ1-PAX8 nucleic acid molecules, ribozyme molecules specific for PAX8-PPARγ1 or PPARγ1-PAX8 nucleic acid molecules, and the like.

The invention further provides efficient methods of identifying agents or lead compounds for agents active at the level of a PAX8-PPARγ1 or PPARγ1-PAX8 molecule (for example in replication, transcription or translation), or PAX8-PPARγ1 or PPARγ1-PAX8 fragment dependent cellular function (for example, binding to a nucleic acid or a ligand). Generally, the screening methods involve assaying for compounds which have a net result of inhibiting production of PAX8-PPARγ1 or PPARγ1-PAX8 polypeptides or inhibiting the function of PAX8-PPARγ1 or PPARγ1-PAX8 polypeptides. Such methods are adaptable to automated, high throughput screening of compounds.

In a preferred embodiment, a method involves screening for an agent that inhibits the production of a PAX8-PPARγ1 or a PPARγ1-PAX8 polypeptide. The method involves determining and comparing the level of, for example, a PAX8-PPARγ1 polypeptide in the absence and in the presence of a compound. According to the method, a decrease in the level of a PAX8-PPARγ1 polypeptide in the presence of the compound is indicative of an agent that inhibits the production of a PAX8-PPARγ1 polypeptide. The compound can be synthesized or harvested from a variety of sources as described herein. The compound can be peptide or non-peptide in nature. A similar approach can be taken to screen for an agent that inhibits the production of a PPARγ1-PAX8 polypeptide.

As mentioned above, the agent may be one which inhibits transcription of a PAX8-PPARγ1 or a PPARγ1-PAX8 nucleic acid molecule. Alternatively, the agent may be one which inhibits translation of a PAX8-PPARγ1 or a PPARγ1-PAX8 nucleic acid molecule. The screening assay can be carried out in a cell free system. In one embodiment, a cell free transcription system may be preferable. In another embodiment, a cell free translation system may be preferable. In yet another embodiment, the assay is carried out in an in vitro cell free transcription and translation system. In still other instances, the screening assay may be performed in a cell, in a tissue or in an animal such as a transgenic, non-human animal.

A wide variety of assays for pharmacological agents are provided, including, labeled in vitro protein-protein binding assays, electrophoretic mobility shift assays, immunoassays, cell-based assays such as two- or three-hybrid screens, expression assays, etc. For example, two-hybrid screens are used to rapidly examine the effect of transfected nucleic acid molecules on the intracellular binding of PAX8-PPARγ1 or PPARγ1-PAX8 polypeptide or fragments thereof to intracellular targets. The transfected nucleic acid molecules can encode, for example, combinatorial peptide libraries or cDNA libraries. Convenient reagents for such assays, e.g., GAL4 fusion proteins, are known in the art. An exemplary cell-based assay involves transfecting a cell with a nucleic acid encoding, for example, a PAX8-PPARγ1 polypeptide fused to a GAL4 DNA binding domain and a nucleic acid encoding a reporter gene operably linked to a gene expression regulatory region, such as one or more GAL4 binding sites. Activation of reporter gene transcription occurs when the PAX8-PPARγ and reporter fusion polypeptides bind to each other such as to enable transcription of the reporter gene. Agents which modulate a PAX8-PPARγ1 polypeptide mediated cell function are then detected through a change in the expression of reporter gene. Methods for determining changes in the expression of a reporter gene are known in the art. In preferred embodiments, the agents so identified are also further screened to preclude those that also bind to either of the source polypeptides. Similar approaches are embraced by the invention involving PPARγ1-PAX8 nucleic acid molecules and polypeptides.

PAX8-PPARγ1 or PPARγ1-PAX8 polypeptide fragments used in the methods, when not produced by a transfected nucleic acid are added to an assay mixture as an isolated polypeptide. PAX8-PPARγ1 or PPARγ1-PAX8 polypeptides preferably are produced recombinantly, although such polypeptides may be isolated from biological extracts. Recombinantly produced PAX8-PPARγ1 or PPARγ1-PAX8 polypeptides include chimeric proteins comprising a fusion of a PAX8-PPARγ1 or a PPARγ1-PAX8 protein with another polypeptide, e.g., a polypeptide capable of providing or enhancing protein-protein binding, sequence specific nucleic acid binding (such as GAL4), enhancing stability of the PAX8-PPARγ1 or a PPARγ1-PAX8 polypeptide under assay conditions, or providing a detectable moiety, such as green fluorescent protein or Flag epitope.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc. to produce structural analogs of the agents.

In methods directed to the administration of an agent into a subject, the agent of the invention can be administered with a therapeutic agent. As used herein, a therapeutic agent is an agent other than the PAX8-PPARγ1 or the PPARγ1-PAX8 nucleic acid molecules, polypeptides, binding agents (including PPARγ ligands) of the invention which has been reported to possess therapeutic effectiveness toward the disorder being treated. A therapeutic agent is also different from those agents described herein which upon administration inhibit or downregulate the production of PAX8-PPARγ1 or PPARγ1-PAX8 polypeptides. In some embodiments, the foregoing agents of the invention may be administered substantially simultaneously with the therapeutic agents. By substantially simultaneously, it is meant that the agent of the invention is administered to a subject close enough in time with the administration of the therapeutic agent so that the two compounds may exert an additive or even synergistic effect, (e.g., reducing a tumor mass).

In certain embodiments the agent can be administered, as mentioned earlier, in combination with therapeutic agents such as anti-cancer agents examples of which include: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Taxol; Taxotere; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. In important embodiments, the agents of the invention are administered in combination with radioactive iodine therapy or treatment with T4.

The pharmaceutical preparations, as described above, are administered. in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result. In some cases this is a decrease in cell proliferation, a decrease in the size of a tumor, or an inhibition of tumor growth.

The invention further provides a medicament and a method of making a medicament. The medicament comprises an agent and a pharmaceutically acceptable carrier. The method involves placing an agent in a pharmaceutically acceptable carrier. The agent may be but is not limited to a PAX8-PPARγ1 or a PPARγ1-PAX8 nucleic acid molecule or a fragment thereof, a PAX8-PPARγ1 or a PPARγ1-PAX8 antisense nucleic acid molecule, a PAX8-PPARγ1 or a PPARγ1-PAX8 polypeptide or fragment thereof, a PAX8-PPARγ1 or a PPARγ1-PAX8 binding agent, and a therapeutic agent as described herein. In a further embodiment, the invention provides a medicament and a method of making the same which includes a PPARγ ligand such as a agonist or an antagonist formulated for use in the treatment of a disorder characterized by a PAX8-PPARγ1 or a PPARγ1-PAX8 nucleic acid molecule or a polypeptide, excluding disorder previously treated with PPARγ ligands (i.e., carcinoma). In one embodiment, the medicament is formulated in a dose and/or a delivery formulation particularly tailored to the treatment of thyroid follicular carcinoma and/or delivery to thyroid tissue.

Generally, doses of active compounds of the present invention would be from about 0.01 mg/kg per day to 1000 mg/kg per day. It is expected that doses ranging from 50–500 mg/kg will be suitable. A variety of administration routes are available. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. In some embodiments of the invention, the mode of administration is direct injection into the thyroid tissue. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule. When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694–1712; incorporated by reference). Those of skill in the art can readily determine the various parameters and conditions for producing antibody or peptide aerosols without resort to undue experimentation.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The PAX8-PPARγ1 or PPARγ1-PAX8 nucleic acid molecules, polypeptides or fragments thereof, as well as binding agents (including antisense molecules) may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Various techniques may be employed for introducing nucleic acid molecules of the invention into cells, depending on whether the nucleic acid molecules are introduced in vitro or in vivo in a host. Such techniques include transfection of nucleic acid-$CaPO_4$ precipitates, transfection of nucleic acid molecules associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acid molecules of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acid molecules into cells, as is known by those skilled in the art. Such systems even permit oral delivery of nucleic acid molecules.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

TABLE 1

Blast Results

SEQ ID NO:1

X90563; U79012; U63415; NM_005037.1; D83233.1; AF033103; AF033343;
AF033342; AF103946; AF059245; AJ006757; AJ006756; Y12419; Y12420;
U84893; X69699; S77904; NM_003466.1; U09138; U01841; U10374;
AF156666.1; AB019561; AF156665.1; AB011365; Y12882; U01664; Z30972;
S77905; S77906; X83591; X83592; AF013266; X57487; X94246;
AJ243133.1; AB005525; AJ243132.1; AB005526; AB005521; AB005524;
AB005522; X99594; NM_003990.1; NM_003989.1; NM_003988.1;
NM_003987.1; L25597; NM_000278.1; Y07617; AB005523; X55781;
AF179301.1; AF072549; NM_008782.1; X99595; AF072548; U45247; L09747;
AF072547; X99593; M96944; AB004249.1; M84163; AF118835; AB026496.1;
X99596; AF072550; AF072556; AF080573; Z97020; Y10121; Y10119;
AJ000667; U45246; L09746; AJ243956.1; AF053763.1; AF053762.1;
Y10122; AJ000666; AJ000669; AJ010503.1; AJ243131.1; AF067541;
AF067540; AF067539; AF067538; AF067537; AF067536; AF067535;
AF067534; AF067533; AF067532; AF067531; AF067530; Y07619; S74349;
NM_005036.1; L28116; AW242425.1; AB026496.1; AF175309.1; AW243356.1;
AW242739.1; AC020288.1; AF164512.1; AC015538.5; AC016483.4;
AC016018.5; AC019853.1; AC019114.1; AC018660.1; AC011672.2;
 AA673643; AI037566; AA717831; AA543722; AI154850; AI593260.1;
AI153002; AA796121; AA511029; AA267605; AA755709; W34083;
AI893887.1; AV076174.1; AI563788.1; AA597048; AV076055.1;
AW047070.1; AW012170.1; AI323000; AA038121; AI527867; AW107536.1;
AW012320.1; AI607695.1; AI317423; AI049299; AA473464; AA260949;
AA239828; AA048439; W35988; AI787639.1; AA501151; AA625223;
AI123591; AI200451; AA088420; H21596; AA314023; AI767379.1;
AI863514.1; AA053612; AI749134.1; AI863526.1; AI339791; AI280973;
AI280895; AA496551; AA053166; AA088517; AA558472; N85138;
AI732763.1; AA581078; AI355115; AW242425.1; AI148692; AA456888.1;
AI762480.1; AA298089; F13615; AA457044.1; AA736382; AA428473;
AA401262; AA506421; AA373868; AW243356.1; AW242739.1; AI683729.1;
AI420066.1; AI092288; AI079139; AI031556; AI022569; AA570000;
W07822; AW196134.1; AW172461.1; AW157484.1; AW139642.1; AW136668.1;
AW079088.1; AW073152.1; AL047655.2; AI983814.1; AI951552.1;
AI926910.1; AI924256.1; AI921835.1; AI913495.1; AI826099.1;
AI808954.1; AI784341.1; AI766272.1; AI764964.1; AI763011.1;
AI640347.1; AI582706.1; AI422902.1; AI417854.1; AI417718.1;
AI380060.1; AI368582; AI267956; AI262488; AI240162; AI223842;
AI220775; AI167363; AI096397; AI041896; AI032279; AA995307;

TABLE 1-continued
Blast Results

AA988343; AA927984; AA878607; AA789028; AA555324; AA485951;
AA464391; AA448966; AA085806; AA084636; AA075306; AA031673; N94332;
N30837; H89337; H89336; T99335; AI012992; AI453959.1; AI235251;
AI111890; AV383052.1; AI497117; AW144737.1; AF122170.1; AA051948;
D33879; AI958368.1; AI717162.1; AA875381; C91798; AA539030; C67965;
D27929; AR030509.1; E08677; I73722; AR030510.1; I28454; I73479;
I09483; I09479; I09510; I28450; E12854; I09484; I09480; I09511;
A27686.1; I08702; I57970; A37795.1; AR068702.1; AR067944.1;
AR067943.1; AR064435.1; AR064434.1; AR064433.1; AR064432.1;
AR064431.1; AR064430.1; AR064429.1; AR062469.1; AR062468.1;
AR062467.1; A60211.1; I90010; I83401; I51914; E06984; E02138;
I33400; I27615; I15007; A29797.1; A03787.1; A21285.1; I47707;
I06223; I07208; I07147; I08089; I08116; I08115; I08673; I09137;
I09269; I09268; I09252; I09251; I09250; I09237; I09302; I09301;
I09308; AC016333.1; AC016683.1; AL032818.2; AC020288.1; AC007328.4;
AC006107; AC015538.5; AC016018.5; AC004898; AQ415323; AQ018690;
AQ262814; AQ700244.1; AQ231184; AQ849999.1; AQ815715.1; AL097028.1;
AQ688441.1; AQ687227.1; AQ576656.1; AL074352.1; AQ051374.2;
AQ327956; AQ322230.1; AQ245922; AQ039676; AQ037325; B74732;
AL016480; B31956; U79012; U63415; NM_005037.1; D83233.1; AF033103;
AF033343; AF033342; X69699; NM_003466.1; AF103946; AF059245;
AJ006757; AJ006756; Y12419; Y12420; U84893; S77904; U09138; U01841;
U10374; AF156666.1; AB019561; AF156665.1; AB011365; Y12882; U01664;
Z30972; S77905; S77906; X83591; X83592; X57487; X94246; AF013266;
AJ243133.1; AB005525; AJ243132.1; AB005526; AB005521; AB005524;
AB005522; X99594; NM_003990.1; NM_003989.1; NM_003988.1;
NM_003987.1; L25597; NM_000278.1; Y07617; AB005523; X55781;
AF179301.1; AF072549; NM_008782.1; X99595; AF072548; U45247; L09747;
AF072547; X99596; X99593; M96944; AB004249.1; M84163; AF118835;
AB026496.1; AF072550; AF072556; AF080573; Z97020; Y10121; Y10119;
AJ000667; U45246; L09746; AJ243956.1; AF053763.1; AF053762.1;
Y10122; AJ000666; AJ000669; AJ010503.1; AJ243131.1; AF067541;
AF067540; AF067539; AF067538; AF067537; AF067536; AF067535;
AF067534; AF067533; AF067532; AF067531; AF067530; Y07619; S74349;
NM_005036.1; L28116; AW242425.1; AB026496.1; AF175309.1; AW243356.1;
AW242739.1; AC020288.1; AF164512.1; AC015538.5; AC016483.4;
AC016018.5; AR030509.1; E08677; I73722; AR030510.1; I28454; I73479;
I09483; I09479; I09510; I28450; E12854; I09484; I09480; I09511;

TABLE 1-continued

Blast Results

A27686.1; I08702; I57970; A37795.1; AR068702.1; AR067944.1;
AR067943.1; AR064435.1; AR064434.1; AR064433.1; AR064432.1;
AR064431.1; AR064430.1; AR064429.1; AR062469.1; AR062468.1;
AR062467.1; A60211.1; I90010; I83401; I51914; E06984; E02138;
I33400; I27615; I23473; I15007; A29797.1; A03787.1; A21285.1;
I47707; I06223; I07208; I07147; I08089; I08116; I08115; I08673;
I09137; I09269; I09268; I09252; I09251; I09250; I09237; I09302;
I09301; I09308; AA673643; AI037566; AA717831; AA543722; AI154850;
AI593260.1; AI153002; AA796121; AA511029; AA267605; AA755709;
W34083; AI893887.1; AV076174.1; AI563788.1; AA597048; AV076055.1;
AW047070.1; AW012170.1; AI323000; AA038121; AI527867; AW107536.1;
AW012320.1; AI607695.1; AI317423; AI049299; AA473464; AA260949;
AA239828; AA048439; W35988; AI787639.1; AA501151;
AA625223; AI123591; AA496551; AI200451; AA088420; H21596; AA314023;
AI767379.1; AI863514.1; AA053612; AI749134.1; AI863526.1; AI339791;
AI280973; AI280895; AA053166; AA088517; AA558472; N85138;
AI732763.1; AA581078; AI355115; AW242425.1; AI148692; AA453686;
AA456888.1; AI762480.1; AA298089; F13615; N40051; AA457044.1;
AA736382; AA428473; AA401262; AA506421; AI375926; AA373868;
AA256006; AW243356.1; AW242739.1; AI683729.1; AI420066.1; AI092288;
AI079139; AI031556; AI022569; AA570000; W07822; AW157484.1;
AW073152.1; AL047655.2; AI983075.1; AI951552.1; AI921835.1;
AI919542.1; AI913495.1; AI829634.1; AI826099.1; AI808954.1;
AI767135.1; AI763011.1; AI640347.1; AI582706.1; AI524538;
AI474820.1; AI422902.1; AI417854.1; AI375237; AI368582; AI267956;
AI262488; AI223842; AI220775; AI190942; AI183863; AI167363;
AI041896; AI005367; AA995307; AA988343; AA927984; AA868369;
AA860366; AA789028; AA555324; AA502877; AA485951; AA464391;
AA233178; AA156460; AA084636; AA035202; AA031673; N30837; H89337;
H92020; H89336; R71623; T99335; T11305; AI012992; AI453959.1;
AI235251; AI111890; AV383052.1; AI497117; AW144737.1; AF122170.1;
AA051948; D33879; AI958368.1; AI717162.1; AA875381; C91798;
AA754119; AA539030; C67965; D27929; AQ415323; U82199; AQ018690;
AQ262814; AQ700244.1; AQ231184; AQ849999.1; AQ815715.1; AL097028.1;
AQ688441.1; AQ687227.1; AQ576656.1; AL074352.1; AQ051374.2;
AQ327956; AQ322230.1; AQ245922; AQ039676; AQ037325; B74732;
AL016480; B31956;
AC016333.1; AC016683.1; AL032818.2; AC020288.1; AC007328.4;
AC006107; AC016018.5; AC004898

TABLE 1-continued

Blast Results

SEQ ID NO:3

X90563; U79012; U63415; NM_005037.1; D83233.1; AF033103; AF033343;
AF033342; X69699; NM_003466.1; AF103946; AF059245; AJ006757;
AJ006756; Y12419; Y12420; U84893; S77904; U09138; U01841; U10374;
AF156666.1; AB019561; AF156665.1; AB011365; Y12882; U01664; Z30972;
S77905; S77906; X83591; X83592; X57487; X94246; AF013266;
AJ243133.1; AB005525; AJ243132.1; AB005526; AB005521; AB005524;
AB005522; X99594; NM_003990.1; NM_003989.1; NM_003988.1;
NM_003987.1; L25597; NM_000278.1; Y07617; AB005523; X55781;
AF179301.1; AF072549; NM_008782.1; X99595; AF072548; U45247; L09747;
AF072547; X99596; X99593; M96944; AB004249.1; M84163; AF118835;
AB026496.1; AF072550; AF072556; AF080573; Z97020; Y10121; Y10119;
AJ000667; U45246; L09746; AJ243956.1; AF053763.1; AF053762.1;
Y10122; AJ000666; AJ000669; AJ010503.1; AJ243131.1; AF067541;
AF067540; AF067539; AF067538; AF067537; AF067536; AF067535;
AF067534; AF067533; AF067532; AF067531; AF067530; Y07619; S74349;
NM_005036.1; L28116; AW242425.1; AB026496.1; AF175309.1; AW243356.1;
AW242739.1; AC020288.1; AF164512.1; AC015538.5; AC016483.4;
AC016018.5; AR030509.1; E08677; I73722; AR030510.1; I28454; I73479;
I09483; I09479; I09510; I28450; E12854; I09484; I09480; I09511;
A27686.1; I08702; I57970; A37795.1; AR068702.1; AR067944.1;
AR067943.1; AR064435.1; AR064434.1; AR064433.1; AR064432.1;
AR064431.1; AR064430.1; AR064429.1; AR062469.1; AR062468.1;
AR062467.1; A60211.1; I90010; I83401; I51914; E06984; E02138;
I33400; I27615; I23473; I15007; A29797.1; A03787.1; A21285.1;
I47707; I06223; I07208; I07147; I08089; I08116; I08115; I08673;
I09137; I09269; I09268; I09252; I09251; I09250; I09237; I09302;
I09301; I09308; AA673643; AI037566; AA717831; AA543722; AI154850;
AI593260.1; AI153002; AA796121; AA511029; AA267605; AA755709;
W34083; AI893887.1; AV076174.1; AI563788.1; AA597048; AV076055.1
AW047070.1; AW012170.1; AI323000; AA038121; AI527867; AW107536.1
AW012320.1; AI607695.1; AI317423; AI049299; AA473464; AA260949;
AA239828; AA048439; W35988; AI787639.1; AA501151; AA625223;
AI123591; AA496551; AI200451; AA088420; H21596; AA314023;
AI767379.1; AI863514.1; AA053612; AI749134.1; AI863526.1; AI339791;
AI280973; AI280895; AA053166; AA088517; AA558472; N85138;
AI732763.1; AA581078; AI355115; AW242425.1; AI148692; AA453686;
AA456888.1; AI762480.1; AA298089; F13615; N40051; AA457044.1;

TABLE 1-continued

Blast Results

AA736382; AA428473; AA401262; AA506421; AI375926; AA373868;
AA256006; AW243356.1; AW242739.1; AI683729.1; AI420066.1; AI092288;
AI079139; AI031556; AI022569; AA570000; W07822; AW157484.1;
AW073152.1; AL047655.2; AI983075.1; AI951552.1; AI921835.1;
AI919542.1; AI913495.1; AI829634.1; AI826099.1; AI808954.1;
AI767135.1; AI763011.1; AI640347.1; AI582706.1; AI524538;
AI474820.1; AI422902.1; AI417854.1; AI375237; AI368582; AI267956;
AI262488; AI223842; AI220775; AI190942; AI183863; AI167363;
AI041896; AI005367; AA995307; AA988343; AA927984; AA868369;
AA860366; AA789028; AA555324; AA502877; AA485951; AA464391;
AA233178; AA156460; AA084636; AA035202; AA031673; N30837; H89337;
H92020; H89336; R71623; T99335; T11305; AI012992; AI453959.1;
AI235251; AI111890; AV383052.1; AI497117; AW144737.1; AF122170.1;
AA051948; D33879; AI958368.1; AI717162.1; AA875381; C91798;
AA754119; AA539030; C67965; D27929; AQ415323; U82199; AQ018690;
AQ262814; AQ700244.1; AQ231184; AQ849999.1; AQ815715.1; AL097028.1;
AQ688441.1; AQ687227.1; AQ576656.1; AL074352.1; AQ051374.2;
AQ327956; AQ322230.1; AQ245922; AQ039676; AQ037325; B74732;
AL016480; B31956; AC016333.1; AC016683.1; AL032818.2; AC020288.1;
AC007328.4; AC006107; AC016018.5; AC004898

SEQ ID NO:5
X90563; U79012; U63415; NM_005037.1; D83233.1; AF033103; AF033343;
AF033342; X69699; NM_003466.1; AF103946; AF059245; AJ006757;
AJ006756; Y12419; Y12420; U84893; S77904; U09138; U01841; U10374;
AF156666.1; AB019561; AF156665.1; AB011365; Y12882; U01664; Z30972;
S77905; S77906; X83591; X83592; X57487; X94246; AF013266;
AJ243133.1; AB005525; AJ243132.1; AB005526; AB005521; AB005524;
AB005522; X99594; NM_003990.1; NM_003989.1; NM_003988.1;
NM_003987.1; L25597; NM_000278.1; Y07617; AB005523; X55781;
AF179301.1; AF072549; NM_008782.1; X99595; AF072548; U45247; L09747;
AF072547; X99596; X99593; X99597; M96944; AB004249.1; M84163;
AF118835; AB026496.1; AF072550; AF072556; AF080573; Z97020; Y10121;
Y10119; AJ000667; U45246; L09746; AJ243956.1; AF053763.1;
AF053762.1; Y10122; AJ000666; AJ010503.1; AJ243131.1; AF067541;
AF067540; AF067539; AF067538; AF067537; AF067536; AF067535;
AF067534; AF067533; AF067532; AF067531; AF067530; Z79997; Y07619;
S74349; NM_005036.1;
AW242425.1; AB026496.1; AF175309.1; AW243356.1; AW242739.1;
AC020288.1; AC008754.3; AC019506.1; AF164512.1; AC015538.5;

TABLE 1-continued

Blast Results

AC015854.2; AC016018.5;

AI012992; AI453959.1; AI235251; AI111890; AV383052.1; AI497117;
AW144737.1; AF122170.1; AA051948; D33879; AI958368.1; AI717162.1;
AA875381; C91798; AA754119; AA539030; C67965; D27929; AR030509.1;
E08677; I73722; AR030510.1; I28454; I73479; I09483; I09479; I09510;
I28450; E12854; I09484; I09480; I09511; A27686.1; I08702; I57970;
A37795.1;

AA673643; AI037566; AA717831; AA543722; AI154850; AI593260.1;
AI153002; AA796121; AA511029; AA267605; AA755709; W34083;
AI893887.1; AV076174.1; AI563788.1; AA597048; AV076055.1;
AW047070.1; AW012170.1; AI323000; AA038121; AI527867; AW107536.1;
AW012320.1; AI607695.1; AI317423; AI049299; AA473464; AA260949;
AA239828; AA048439; W35988; AI787639.1; AA501151; AA625223;
AA496551; AI123591; AI200451; AA088420; H21596; AA314023;
AI767379.1; AI863514.1; AA053612; AI749134.1; AI863526.1; AI339791;
AI280973; AI280895; AA053166; AA088517; AA453686; AA558472; N85138;
AI732763.1; AA581078; AI355115; N40051; AW242425.1; AI375926;
AA256006; AI148692; AA456888.1; AI762480.1; AA298089; F13615;
AA447755; AA457044.1; AA736382; AA428473; AA401262; AA506421;
AA373868; AW243356.1; AW242739.1; AI683729.1; AI420066.1; AI092288;
AI079139; AI031556; AI022569; AA570000; W07822; AC016333.1;
AC016683.1; AL032818.2; AC009582.1; AC020288.1; AC007328.4;
AC006107; AC008754.3; AC019506.1; AC015854.2; AC016018.5; AQ415323;
U82199; AQ018690; AQ262814; AQ700244.1; AQ231184; AQ849999.1;
AQ815715.1; AL097028.1; AQ688441.1; AQ687227.1; AQ632355.1;
AQ576656.1; AL074352.1; AQ547577.1; AQ051374.2; AQ327956;
AQ322230.1; AQ245922; AQ039676; AQ037325; AQ020203; B74732;
AL016480; B31956

SEQ ID NO:22

X90563; U79012; U63415; NM_005037.1; D83233.1; AF033103; AF033343;
AF033342; S77904; X69699; AF103946; AF059245; AJ006757; AJ006756;
S77905; S77906; Y12419; Y12420; U84893; NM_003466.1; U09138; U01841;
U10374; AF156666.1; AB019561; AF156665.1; AB011365; Y12882; U01664;
Z30972; X83592; X83591; X57487; AF013266; X94246; AJ243133.1;
AB005525; AJ243132.1; AB005526; AB005521; AB005524; AB005522;
X99594; NM_003990.1; NM_003989.1; NM_003988.1; NM_003987.1; L25597;
NM_000278.1; Y07617; AB005523; X55781; AF179301.1; AF072549;
NM_008782.1; X99590.1; X99595; AF072548; U45247; L09747; AF072547;

TABLE 1-continued

Blast Results

X99593; X99597; M96944; AB004249.1; M84163; AF118835; AB026496.1;
X99596; AF072550; AF072556; AF080573; Z97020; Y10121; Y10119;
AJ000667; U45246; L09746; AJ243956.1; AF053763.1; AF053762.1;
Y10122; AJ000666; AJ010503.1; AJ243131.1; AF067541; AF067540;
AF067539; AF067538; AF067537; AF067536; AF067535; AF067534;
AF067533; AF067532; AF067531; AF067530; Y07619; S74349; NM_005036.1;
AW242425.1; AB026496.1; AF175309.1; AW243356.1; AW242739.1;
AC020288.1; AC008754.3; AC019506.1; AF164512.1; AC015538.5;
AC015854.2; AC016018.5; AA673643; AI037566; AA717831; AA543722;
AI154850; AI593260.1; AI153002; AA796121; AA511029; AA267605;
AA755709; W34083; AI893887.1; AV076174.1; AI563788.1; AA597048;
AV076055.1; AW047070.1; AW012170.1; AI323000; AA038121; AI527867;
AW107536.1; AW012320.1; AI607695.1; AI317423; AI049299; AA473464;
AA260949; AA239828; AA048439; W35988; AI787639.1; AA501151;
AA625223; AI123591; AI200451; AA088420; H21596; AA314023;
AI767379.1; AI863514.1; AA053612; AI749134.1; AI863526.1; AI339791;
AI280973; AI280895; AA496551; AA053166; AA088517; AA558472; N85138;
AI732763.1; AA581078; AI355115; AW242425.1; AI375926; AA256006;
N40051; AI148692; AA453686; AA456888.1; AI762480.1; AA298089;
F13615; AA447755; AA457044.1; AA736382; AA428473; AA401262;
AA506421; AA373868; AW243356.1; AW242739.1; AI683729.1; AI420066.1;
AI092288; AI079139; AI031556; AI022569; AA570000; W07822; AI012992;
AI453959.1; AI235251; AI111890; AV383052.1; AI497117; AW144737.1;
AF122170.1; AA051948; D33879; AI958368.1; AI717162.1; AA875381;
C91798; AA539030; C67965; D27929;
AR030509.1; E08677; I73722; AR030510.1; I28454; I73479; I09483;
I09479; I09510; I28450; E12854; I09484; I09480; I09511; A27686.1;
I08702; I57970; A37795.1; AQ415323; AQ018690; AQ262814; AQ700244.1;
AQ231184; AQ849999.1; AQ815715.1; AL097028.1; AQ688441.1;
AQ687227.1; AQ632355.1; AQ576656.1; AL074352.1; AQ547577.1;
AQ051374.2; AQ327956; AQ322230.1; AQ245922; AQ106819; AQ039676;
AQ037325; AQ020203; B74732; AL016480; B31956;
AC016333.1; AC016683.1; AL032818.2; AC009582.1; AC020288.1;
AC007328.4; AC006107; AC008754.3; AC019506.1; AC015854.2; AC016018.5

SEQ ID NO:36

NM_003466.1, L19606.1, X69699.1, NM_013952.1, S77904.1, X83591.1,
NM_013951.1, S77905.1, NM_013953.1, NM_011040.1, X57487.1, X94246.1,
NM_013992.1, S77906.2, X83592.1, AF130778.1, X99596.1, X99597.1,
NM_015869.1, U79012.1, AF033103.1, U63415.1, D83233.1, AB005520.1,

TABLE 1-continued

Blast Results

X99598.1, AF103946.1, AF059245.1, AJ006757.1, NM_011146.1, Y12882.1,
U09138.1, NM_013124.1, AF179301.1, AF156666.1, AF072549.1,
AF072556.1, AB019561.1, Y12420.1, AJ010504.1, AC004770.1,
AE004331.1, NM_014804.1, AE003762.1, AJ231086.1, AP001111.1,
D28596.1, AB018296.1, AC069251.5, AC006322.2, AC007528.5,
AL353812.13, AL136087.12, AF023877.1, AL079303.3, AD000091.1,
AJ271980.1, AL035427.17, Y13284.1, Y13101.1, X61361.1, AV605731.1,
AP002754.1, AC015987.3, AC018670.3, AV609343.1, BE480002.1,
AC025553.3, AC069513.8, AC073221.2, AC026332.5, AC074240.1,
AC073773.2, AC025282.4, AC073498.2, AC021734.2, AC055742.7,
AL353899.10, AL160161.3, AV596715.1, AV593886.1, BB433022.1,
BB347389.1, AA496551.1, AA453686.1, AW653703.1, AI375926.1,
N40051.1, AA256006.1, AW580428.1, AA447755.1, BE207571.1,
BE019930.1, AI697310.1, AW660282.1, AA862526.1, AV605731.1,
AI154850.1, BB256732.1, AV609343.1, BE480002.1, AV596715.1,
AV593886.1, BB433022.1, BB347389.1, BB249119.1, AW876803.1,
AW697042.1, AA673643.1, H92020.1, A59488.1, I45766.1, I23473.1,
A82273.1, A76958.1, A62673.1, A51133.1, AR060975.1, AR053408.1,
AR053401.1, AR052808.1, AR052807.1, AR051987.1, AR044683.1,
AR036574.1, AR036573.1, AR036572.1, AR028465.1, AR012622.1,
AR009500.1, I75051.1, I67748.1, I55624.1, I52161.1, I36923.1,
I27682.1, I24013.1, A73577.1, A77970.1, A74991.1, A43169.1,
A39900.1, A37261.1, I08156.1, I08166.1, E13123.1, E03349.1,
E03348.1, E01630.1, AC016683.5, AC024704.3, AC016333.5, AC025581.2,
AC025689.3, AP002754.1, AP002380.1, AC015987.3, AC018670.3,
AC015916.3, AC039056.4, AC024083.2, AC015854.3, AC019506.1,
AC025553.3, AC069513.8, AC073221.2, AC073110.1, AC026332.5,
AC074240.1, AC073773.2, AC025282.4, AC073498.2, AC021734.2,
AC055742.7, AC010090.5, AC073676.1, AC048373.2, AC011553.3,
AC011492.5, AC009099.6, AC023128.2, AC021594.3, AC025111.2,
AC011575.3, AL353899.10, AL160161.3, AP002378.1, AP001641.2.

SEQ ID NO:37

NM_003466.1; NM_013951.1; L19606.1; S77905.1; NM_013953.1;
NM_013952.1; S77904.1; X69699.1; X83591.1; NM_011040.1; X57487.1;
X94246.1; NM_013992.1; S77906.2; X99597.1; NM_015869.1; U79012.1;
AF033103.1; U63415.1; D83233.1; X83592.1; AB005520.1; X99598.1;
AF103946.1; AF059245.1; AJ006757.1; NM_011146.1; Y12882.1; U09138.1;
NM_013124.1; AF156666.1; AF072549.1; AF072556.1; AB019561.1;

TABLE 1-continued

Blast Results

Y12420.1; AC004770.1; AE004331.1; NM_014804.1; AE003762.1;
AJ231086.1; AP001111.1; D28596.1; AB018296.1; AC069251.5;
AC006322.2; AC007528.5; AL353812.13; AL136087.12; AF023877.1;
AL079303.3; AD000091.1; AJ271980.1; AL035427.17; Y13284.1;
AC011229.2; AC006075.1; AC005950.1; AC005186.1; AV605731.1;
AP002754.1; AC015987.3; AV609343.1; AC025553.3; AC069513.8;
AC073221.2; AC073773.2; AC025282.4; AC073498.2; AC021734.2;
AC055742.7; AL353899.10; AL160161.3; AV596715.1; AV593886.1;
AC073211.4; AC009452.14; AC021060.9; AC016512.3; AC027290.8;
AL136099.9; AL355979.3; AW580428.1; AI375926.1; AA256006.1;
N40051.1; AA496551.1; AW653703.1; AA453686.1; AA447755.1;
BE207571.1; BE019930.1; AI697310.1; AA862526.1; AV605731.1;
AI154850.1; BB256732.1; AV609343.1; AV596715.1; AV593886.1;
AW876803.1; AW697042.1; AA673643.1; BE514030.1; BE409242.1;
BE396469.1; BE213729.1; BE252673.1; BB199469.1; AW596832.1;
AW415650.1; AW348796.1; AW279427.1; AI809783.1; AI807557.1;
AV093355.1; AI743532.1; AI578215.1; AI467839.1; AI443115.1;
D43354.1; AA882240.1; AA438616.1; AA687785.1; C77889.1; AA614822.1;
C72897.1; AA292282.1; H33771.1; Z17403.1; A59488.1; A82273.1;
A76958.1; A62673.1; A51133.1; AR060975.1; AR053408.1; AR053401.1;
AR052808.1; AR052807.1; AR051987.1; AR044683.1; AR036574.1;
AR036573.1; AR036572.1; AR028465.1; AR012622.1; AR009500.1;
I75051.1; I67748.1; I55624.1; I52161.1; I36923.1; I27682.1;
I24013.1; A73577.1; A77970.1; A74991.1; A43169.1; A39900.1;
A37261.1; I08156.1; I08166.1; E13123.1; E03349.1; E03348.1;
E01630.1; AC024704.3; AC016683.5; AC016333.5; AC025581.2;
AC025689.3; AP002754.1; AP002380.1; AC015987.3; AC015916.3;
AC024083.2; AC015854.3; AC019506.1; AC073773.2; AC021734.2;
AC073676.1; AC011492.5; AC009099.6; AC025111.2; AP002378.1

SEQ ID NO:38

NM_003466.1; NM_013951.1; L19606.1; NM_013992.1; S77905.1;
NM_013953.1; NM_013952.1; S77906.2; S77904.1; X69699.1; X83591.1;
X94246.1; NM_011040.1; X57487.1; NM_015869.1; U79012.1; AF033103.1;
U63415.1; D83233.1; AB005520.1; X99598.1; X83592.1; AF103946.1;
AF059245.1; AJ006757.1; NM_011146.1; Y12882.1; U09138.1;
NM_013124.1; AF156666.1; AF072549.1; AF072556.1; AB019561.1;
Y12420.1; D28596.1; AC069251.5; AC006322.2; AD000091.1; AJ271980.1;
AC011229.2; AE003443.1; NM_004689.1; AC005232.1; AC006557.2;
AC006075.1; AF031898.1; AL359399.1; AC000399.1; S82171,1; U59670.1;

TABLE 1-continued

Blast Results

U43753.1; U34811.1; U35113.1; AP001754.1; AP001063.1; AV605731.1;

AC015987.3; AV609343.1; AC025553.3; AC073221.2; AC073498.2;

AC021734.2; AV596715.1; AV593886.1; AC009452.14; AC009169.6;

AC009156.7; AC015658.3; AC027290.8; AL137064.3; BE514030.1;

BE409242.1; BE396469.1; BE252673.1; BE207571.1; BE019930.1;

AI375926.1; AI697310.1; AW580428.1; AA447755.1; AA256006.1;

N40051.1; AW653703.1; AA453686.1; AA496551.1; AA862526.1;

AV605731.1; AI154850.1; AV609343.1; AV596715.1; AV593886.1;

AW876803.1; AW697042.1; AA673643.1; BE514030.1; BE409242.1;

BE396469.1; BE213729.1; BE252673.1; AW596832.1; AW415650.1;

AW348796.1; AW279427.1; AI809783.1; AI807557.1; AV093355.1;

AI743532.1; AI578215.1; AI467839.1; AI443115.1; D43354.1;

AA687785.1; C72897.1; AA292282.1; Z17403.1; A59488.1; A82273.1;

A62673.1; AR053408.1; AR053401.1; AR052808.1; AR052807.1;

AR044683.1; AR036574.1; AR036573.1; AR036572.1; I67748.1; A43169.1;

A39900.1; A37261.1; I08156.1; I08166.1; E13123.1; E03349.1;

E03348.1; E01630.1; AC024704.3; AC016683.5; AC016333.5; AC025581.2;

AC015987.3; AC024083.2; AC025553.3; AC073221.2; AC073110.1;

AC073498.2; AC021734.2; AC073676.1; AC048373.2; AC011492.5;

AP002378.1.

The following examples are included for purposes of illustration and are not intended to limit the scope of the invention.

EXAMPLES

Thyroid follicular tumors were selected for this study based on availability of both thyroidectomy specimens and frozen tumor tissues. The diagnoses of all thyroid tumors were rendered by staff pathologists at the Brigham and Women's Hospital or Children's Hospital, Boston, Mass., using World Health Organization and current standard practice criteria (Chr. Hedinger, *Histologic Typing of Thyroid Tumours* (Springer-Verlag Berlin Heidelberg, ed. 2, 1988); J. Rosai, M. Carcangiu, R. DeLellis, *Atlas of Tumor Pathology: Tumors of the Thyroid Gland* (Armed Forces Institute of Pathology, Washington, D.C., 1992). All follicular carcinomas, and not follicular adenomas, exhibited vascular and/or full thickness capsular invasion by tumor cells. The follicular carcinoma patients included 6 adults (ages 25–69) and two children (ages 11 and 13) with tumors (2.2–6 cm) lacking local invasion or metastases.

Figure 1B:
FIG. 1B is a photograph of cells stained by in situ hybridization with probes specific for regions centromeric and telomeric to the 3p25 breakpoint.
Figure 1C:
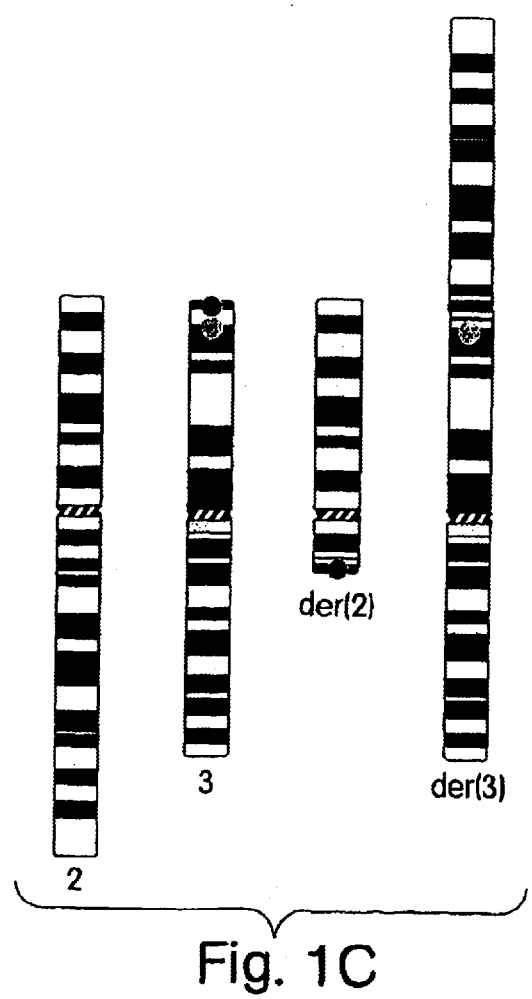
FIG. 1C is a schematic showing the banding of wild type and translocated chromosomes 2 and 3, with probes specific for regions centromeric and telomeric to the 3p25 breakpoint indicated as circles.
Figure 2A:
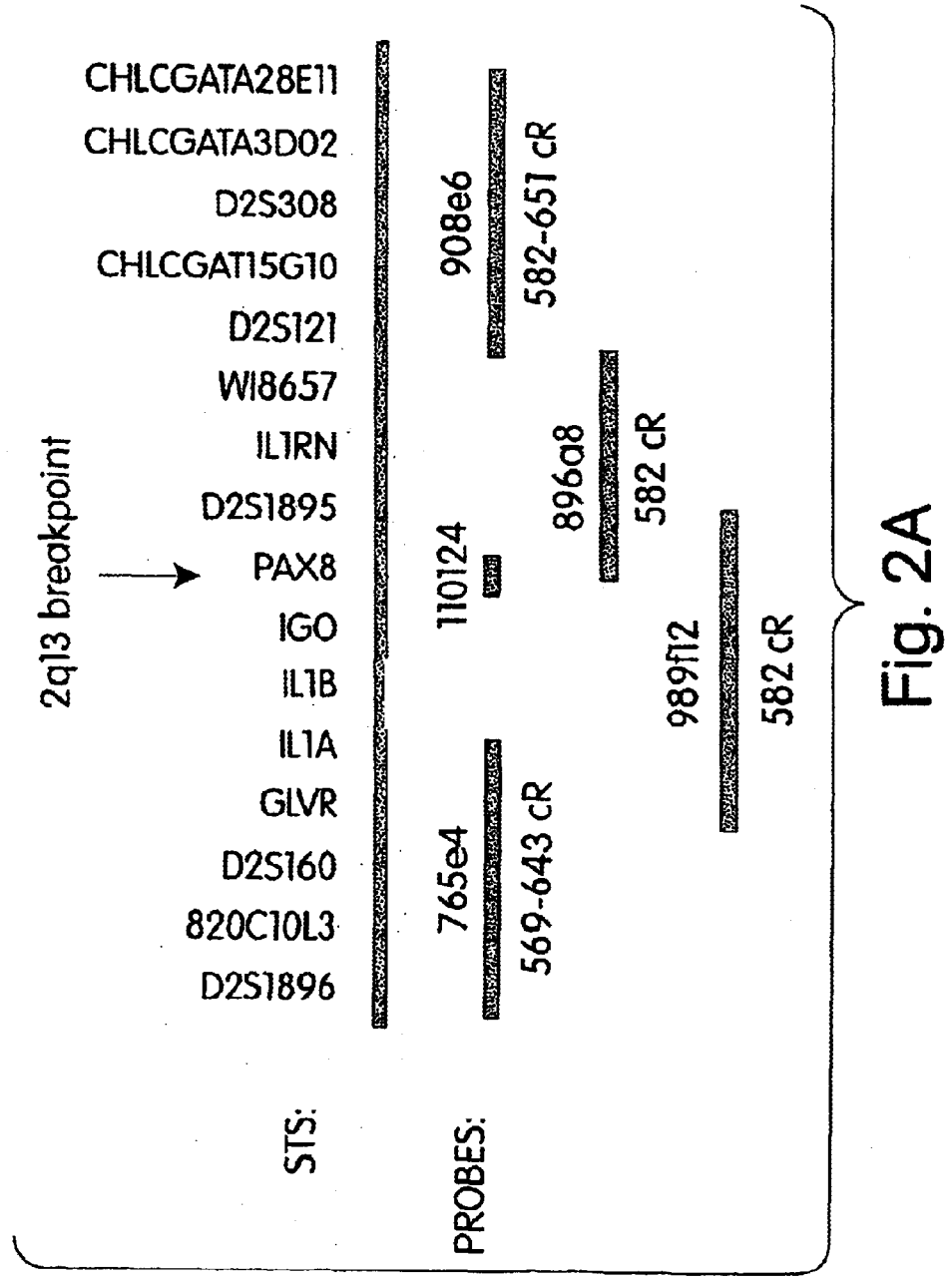
FIG. 2A is a schematic showing the location of the 2q13 breakpoint, including the PAX8 locus, and the hybridization pattern of probes specific for regions centromeric and telomeric to the 2q13 breakpoint.
Figure 2B:
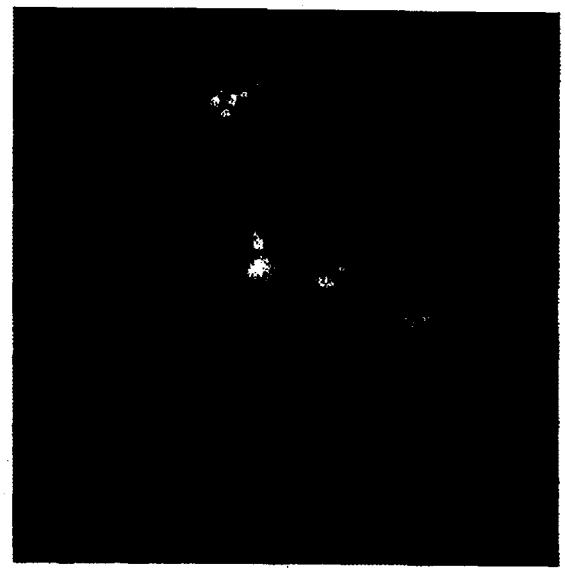
FIG. 2B is a photograph of cells stained by in situ hybridization with probes specific for regions centromeric and telomeric to the 2q13 breakpoint.
Figure 2C:
FIG. 2C is a schematic showing the banding of wild type and translocated chromosomes 2 and 3, with probes specific for regions centromeric and telomeric to the 2q13 breakpoint indicated as circles.

To define the biochemical nature of t(2;3)(q13;p25) observed in follicular thyroid carcinoma, the 3p25 and the 2q13 translocation breakpoints were mapped using dual color fluorescence in situ hybridization (FISH) with yeast artificial (YAC) and bacterial artificial (BAC) chromosome probes on touch preparations of interphase follicular carcinoma nuclei. The 3p25 breakpoint interval was narrowed to less than a 600 kb region bordered by YACs 753f7 (telomeric) and 903e6 (centromeric) (FIG. 1A). Hybridization with flanking YACs 753f7 and 932f3 confirmed 3p25 rearrangement in tumor but not normal epithelial or stromal cells (FIG. 1B). The 2q13 breakpoint region was localized within two overlapping YACs, 989f12 and 896a8 (FIG. 2A), to a locus containing PAX8, a transcription factor essential for thyroid follicular cell development. To test for involvement of PAX8 in t(2;3)(q13;p25), BAC 110L24 was isolated from a human genomic BAC library by PCR with PAX8 cDNA primers. BAC 110L24 crossed the 2q13 breakpoint and co-hybridized with 31)25 YAC 753f7 (FIG. 2B), suggested formation of a novel PAX8-containing fusion oncogene. PPARγ-containing BAC, 321f13 from Cal Tech BAC library, also crossed the 3p25 breakpoint and co-hybridized with 2q13 YAC 989f12. Interphase FISH was performed as in (S. Xiao et al, *Am. J. Pathol.* 147, 896 (1995)) with modifications (C. Hoffman and F. Winston, *Gene* 57, 267 (1987); D. Sinnett, C. Richer, Baccichet, *Biotechniques* 24, 752 (1998)).

RACE, RT-PCR, and Northern blots were performed with total RNA isolated from thyroid tissues by either guanidine thiocyanate/cesium chloride or by the TEIzol reagent (Life Technologies). For RACE and RT-PCR, cDNA synthesis was performed on 1 ug total RNA at 42° C. for 25 min using oligoT-m13 primers (Takara, Shiga, Japan). SMART RACE was used to generate full length PAX8-PPARγ1 cDNA clones (Clontech). 5' PAX8 primers included 5'-GCCACCAAGTCCCTGAGTCC-3' (SEQ ID NO:28), 5'-GCATTGACTCACAGAGCAGCA-3' (SEQ ID NO:17), 5'-GCTCAACAGCACCCTGGA-3' (SEQ ID NO:18), 5'-GCAACCTCTCGACTCACCAG-3' (SEQ ID NO:19), 5'-GACCTACGGGAGGAAGCCC-3' (SEQ ID NO:29), and 5'-GCGGACCCAAGCAGTGAG-3' (SEQ ID NO:30). 3' PPARγ primers included: 5'-CAAAGGAGTGGGAG TGGTCT-3'(SEQ ID NO:20), 5'-CATTACGGAG AGATCCACGG-3' (SEQ ID NO:21), and 5'-TTTCTT ATGGTCAGATTTTCC-3' (SEQ ID NO:31). PCR products were gel purified and/or subcloned and sequenced using large dye terminator chemistries on automated 310 or 377 DNA sequencers (Applied Biosystems). Full length human PPARγ or PAX8 cDNAs probes were used for Northern blots.

Figure 3A:
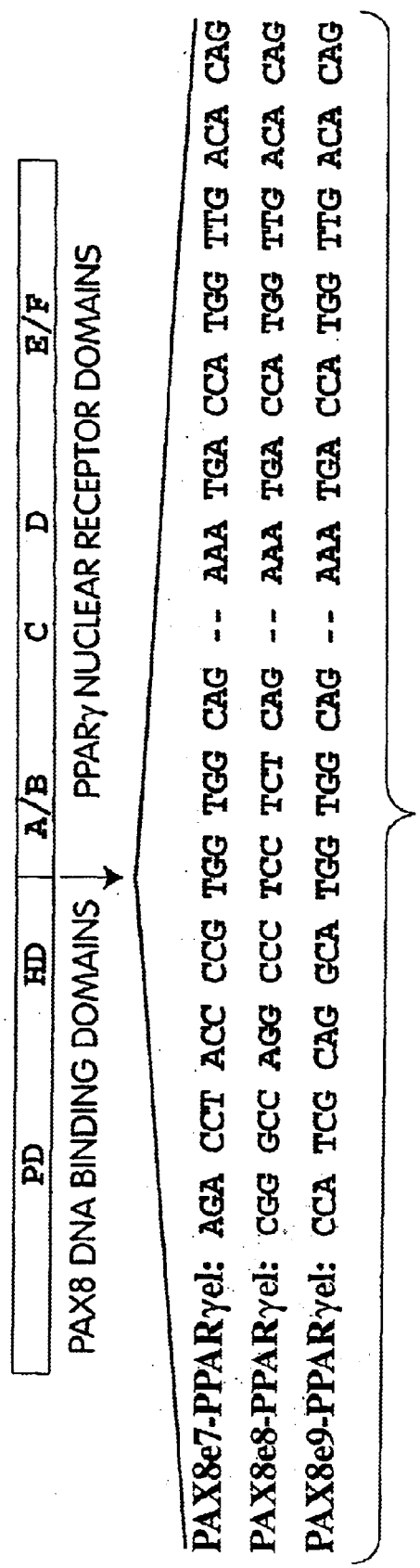
FIG. 3A illustrates the structure and nucleotide sequence of three PAX8-PPARγ1 nucleic acid fusion junctures.

To identify the second partner in this fusion oncogene, rapid amplification of cDNA ends (RACE) was performed using PAX8 primers. Sequence of RACE products specific to follicular carcinoma versus follicular adenoma or normal thyroid tissues showed fusion of PAX8 to the nuclear receptor PPARγ (FIG. 3A). PPARγ had been mapped previously to the 3p25 breakpoint interval, supporting its involvement in t(2;3)(q13;p25). RT-PCR sequencing of PAX8-PPARγ1 nucleic acid molecules amplified from follicular carcinomas revealed fusion of wild type PAX8 exons 1–7, 1–8, or 1–9 to PPARγ exons 1–6. The transactivation domains of PAX8 (exons 10–12) and the 28 amino-terminal amino acids of PPARγ2 (exon B) were excluded. The resulting chimeric oncoprotein (theoretical molecular weight 87–97 kDa) is predicted to encode the paired and partial homeobox domains of PAX8 fused to the DNA binding, ligand binding, RXR dimerization and transactivation domains of (i.e., domains A–F) of PPARγ1 (FIG. 3A). cDNA breakpoint sequences in three additional follicular carcinoma cases demonstrated fusion of PAX8 exons 7, 8, or 9 with PPARγ exon 1 (FIG. 3A). These alternatively spliced forms were co-expressed in all cases (see FIG. 4A).

Figure 3B:
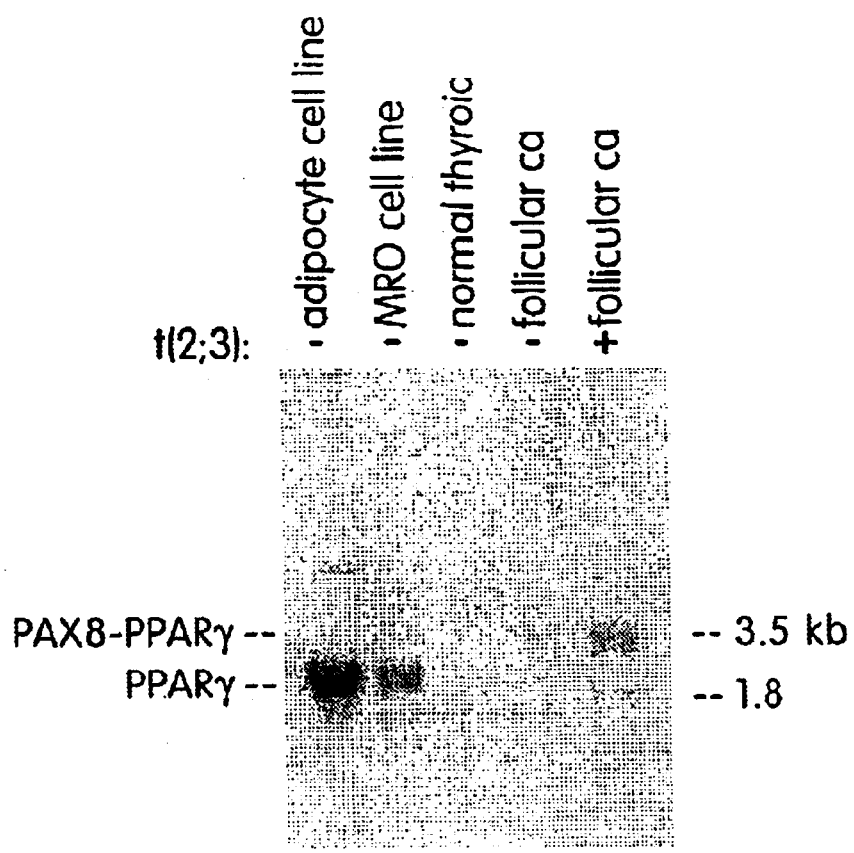
FIG. 3B illustrates the expression of the PAX8-PPARγ1 nucleic acid molecule in follicular carcinoma cells.
Figure 3C:
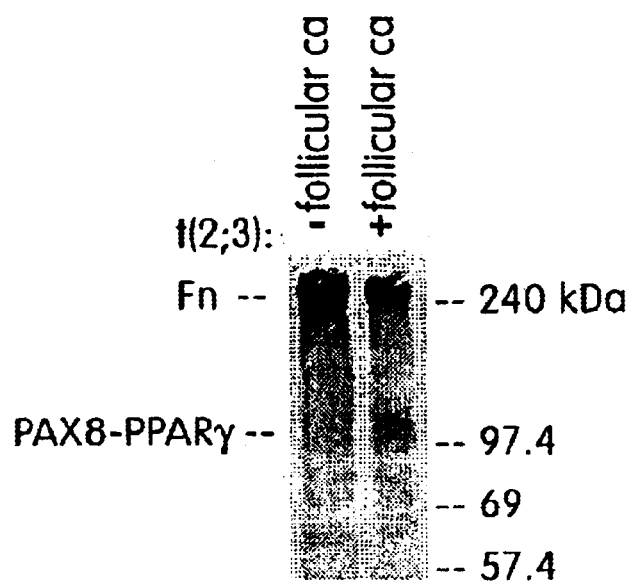
FIG. 3C illustrates the expression of the PAX8-PPARγ1 polypeptide in follicular carcinoma cells.

Expression of PAX8-PPARγ1 in human thyroid follicular carcinoma was investigated at the mRNA and protein levels. A 2.9–3.0 kb putative PAX8-PPARγ1 transcript was identified in t(2;3)-positive but not t(2;3)-negative follicular carcinoma tissues using a PPARγ cDNA probe on northern blots containing total RNA (FIG. 3B). In contrast, only the wild type PPARγ transcript (1.8 kb) was detected in Moser colonic adenocarcinoma and MRO thyroid carcinoma cells and in normal thyroid tissues (FIG. 3B), all lacking t(2;3). Hybridization with a PAX8 cDNA probe confirmed the 2.9–3.0 kb transcript was PAX8-PPARγ1. The 2.9–3.0 kb fusion transcript migrated closely to the wild type transcript of PAX8 (3.1 kb). A putative PAX8-PPARγ1 fusion oncoprotein (98 kDa) was immunoprecipitated with an anti-PPARγ monoclonal antibody from lysates of a t(2;3)-positive follicular carcinoma culture metabolically radiolabeled with ($^{35}$S)methionine and ($^{35}$S)cysteine but not from lysates of a t(2;3)-negative follicular adenoma culture in the same experiment (FIG. 3C). The above experiments provide strong evidence at the DNA, mRNA, and protein levels that a novel PAX8-PPARγ1 fusion oncogene/oncoprotein is associated with thyroid follicular carcinoma. Metabolic radiolabeling, immunoprecipitation, and SDS-PAGE were performed as in (T. Kroll et al., *J. Biol. Chem.* 269, 9270 (1994)) using Easy tag EXPRESS protein labeling mix (NEN-Dupont). Immunoprecipitations were performed with the PPARγ monoclonal antibody E8 (#SC-7273) and corresponding blocking peptide (#SC-7273P) (Santa Cruz). Fibronectin was precipitated by virtue of its non-immunospecific association with protein-A sepharose. Primary thyroid follicular adenoma and follicular carcinoma cultures were obtained by mechanical dissociation and collagenase treatment of tumor fragments in F10 medium, 5% fetal calf serum. Attached cells were cultured in F10 medium containing 5% fetal calf serum and mitomycin C.

The prevalence of PAX8-PPARγ1 in human thyroid follicular neoplasms was examined by RT-PCR and immunohistochemistry. RT-PCR with nested primers (in exons 6 and 7 of PAX8 and exon 1 of PPARγ) generated predicted products in 5 of 8 follicular carcinomas (FIGS. 4A and 4C), but not in 20 follicular adenomas, 10 papillary carcinomas or 10 multi-nodular hyperplasias (FIG. 4C). Immunohistochemistry on paraffin-embedded human thyroid tissues showed that 7 of the 8 follicular carcinomas exhibited strong nuclear immunoreactivity for PPARγ, whereas the 20 follicular adenomas, 10 papillary carcinomas, 10 multi-nodular hyperplasias and normal thyroid tissues exhibited only sparse nuclear and cytoplasmic immunoreactivity (FIGS. 4B and 4C). Immunoreactivity was inhibited by pre-incubation of the antibody with a PPARγ synthetic peptide against which it was raised (FIG. 4B). These findings argue that PAX8-PPARγ is specific for follicular carcinoma amongst common thyroid follicular neoplasms.

Immunohistochemistry was performed on paraffin-embedded human thyroid tissues using microwave antigen retrieval for 30 min at 199° F. in 10 mM citrate buffer, pH 6. Sections were incubated with the PPARγ monoclonal antibody E8. The LSAB avidin-biotin-complex and DAB (Dako) was used for immune complex detection.

Three of the 8 follicular carcinomas generated no RT-PCR product (FIGS. 4A and 4C). One RT-PCR negative case contained t(2;3)(q13;p25) by cytogenetics and was immunoreactive for PPARγ suggesting it contained a different PAX8-PPARγ1 genomic (and thus mRNA) breakpoint. The second RT-PCR negative case was immunoreactive for PPARγ and exhibited 3p25 but not 2q13 rearrangements based on FISH, raising the possibility that it contained an alternate translocation involving PPARγ and a non-PAX8 partner. The third RT-PCR negative case exhibited no evidence of t(2;3)(q13;p25) by FISH or immunohistochemistry, suggesting it had arisen independent of PAX8-PPARγ1. In summary, 7 of the 8 thyroid follicular carcinomas exhibited evidence of PPARγ rearrangement, and 6 of the 8 follicular carcinomas exhibited evidence of PAX8-PPARγ1 fusion. In contrast, PAX8-PPARγ1 was undetectable in 40 other thyroid tumors.

These experiments show that t(2;3)(q13;p25) and PAX8-PPARγ1 fusion define a common oncogenic pathway in human thyroid follicular carcinoma. PAX8-PPARγ1 is the first nuclear receptor fusion oncogene identified in a human solid tumor and the second in a human cancer. It likely plays an essential role in thyroid follicular carcinogenesis. Interestingly, activities of PPARγ appear to reduce growth and promote differentiation in human carcinomas arising in the breast, colon, and prostate. Furthermore, point mutations in the PPARγ ligand binding domain identified in some colonic carcinomas raise the possibility that alterations in PPARγ function contribute to development or progression of this cancer. These data are consistent with this possibility.

PAX8-PPARγ1 is useful both as a novel molecular marker and in therapeutic strategies for follicular carcinoma. It appears both sensitive and specific for discriminating follicular carcinomas from benign tumors. Because many thyroid operations are performed to exclude the possibility of malignancy, improved identification of carcinomas in preoperative biopsies is predicted to reduce the number of thyroid surgeries, increase the percentage of malignancies resected, and reduce the overall cost of treating patients with thyroid nodules. PPARγ ligands may modulate PAX8-PPARγ1 activity and tumor growth in follicular carcinoma patients. This type of approach is first line therapy for patients with acute promyelocytic leukemia (APML), the other human cancer which a nuclear receptor fusion oncogene has been identified. In APML, treatment with a nuclear receptor ligand all-trans retinoic acid induces remission in nearly every patient harboring the PML-RAR (retinoic acid receptor α) translocation. PPARγ ligands with anti-tumorigenic activity could benefit patients with disseminated and/or locally invasive follicular carcinoma as an adjunct or alternative to radio-iodine therapy.

Figure 5:
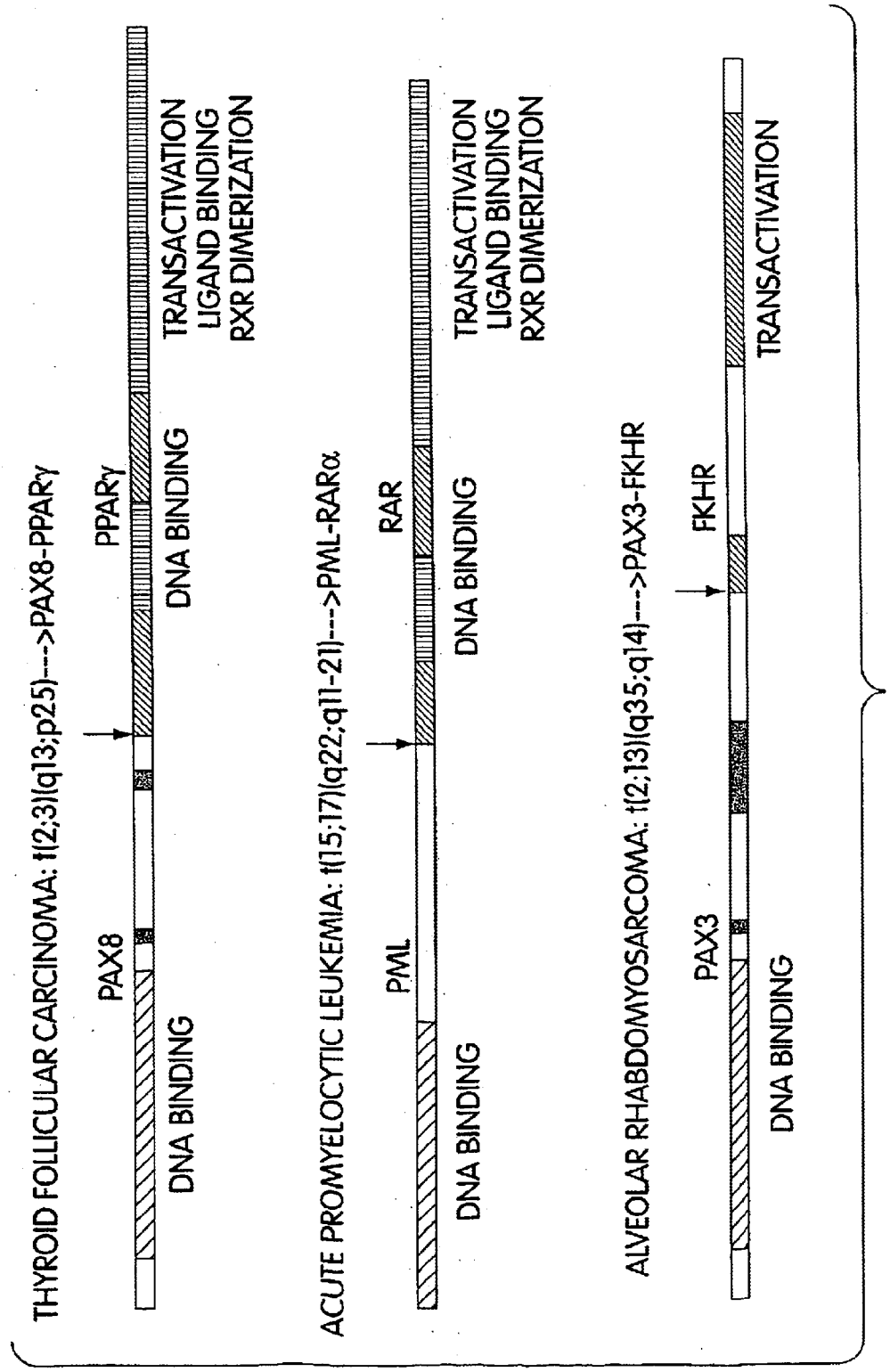
FIG. 5 is a schematic of the PAX8-PPARγ1 polypeptide with comparison to PML-RARα polypeptide and PAX3-FKHR polypeptide.

PAX8-PPARγ1 {t(2;3)(q13;p25)} in human thyroid follicular carcinoma exhibits extensive structural similarity to PAX3-FKHR {t(2;13)(q35;q14)} in human alveolar rhabdomyosarcoma and to PML-RARγ {t(15;17)(q22;q11–21)} in human acute promyelogenous leukemia. On one hand, both PAX8-PPARγ1 and PAX3-FKHR contribute PAX paired and (complete or partial) homeobox DNA binding but not transactivation domains to their respective oncoproteins (FIG. 5). On the other hand, both PAX8-PPARγ1 and PML-RARα contribute most of nuclear receptor domains A/B, C (DNA binding), D (co-repressor binding), and E/F (ligand binding, ligand-dependent transactivation, RXR dimerization) to their respective oncoproteins (FIG. 5). Such homologies argue strongly that conserved molecular cytogenetic mechanisms underlie these diverse human cancers.

Figure 6A:
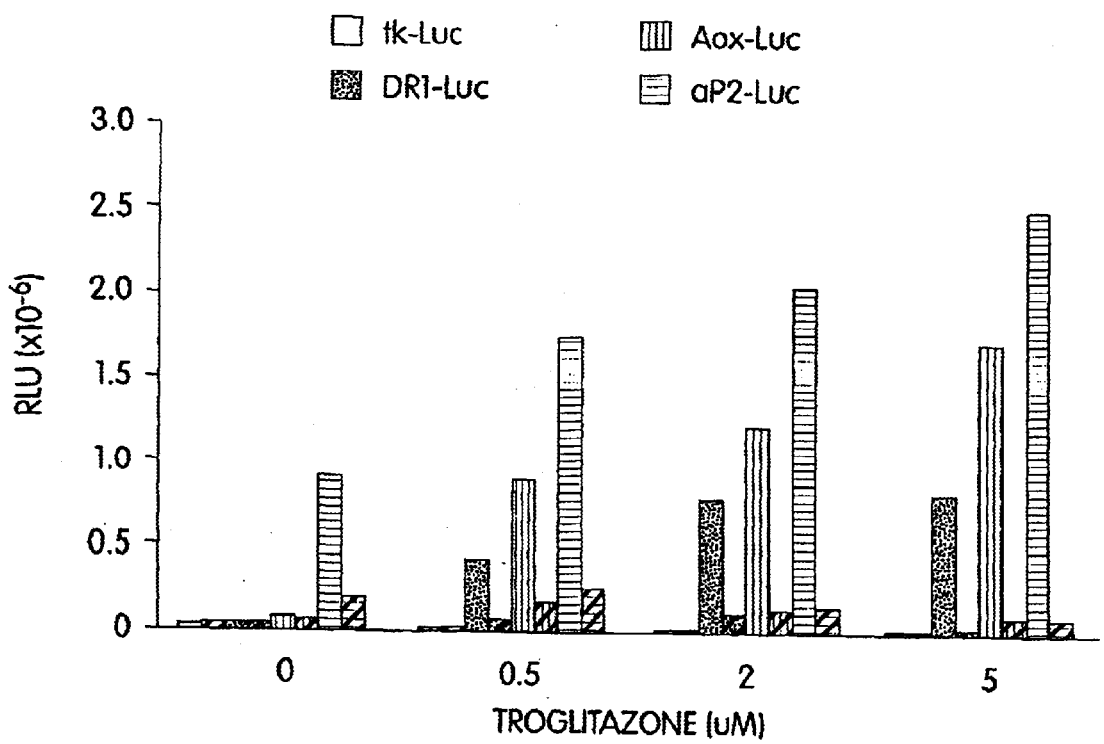
FIG. 6A is a histogram showing the response of PPARγ and PAX8-PPARγ1 to troglitazone induced transactivation.
Figure 6B:
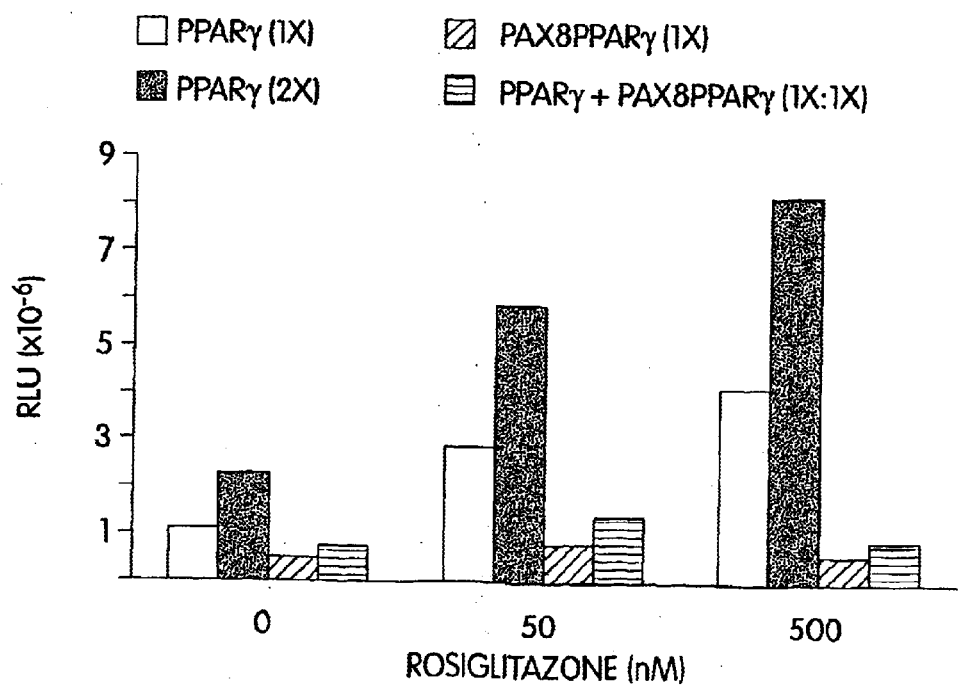
FIG. 6B is a histogram showing the response of PPARγ to rosiglitazone induced transactivation in the presence and absence of PAX8-PPARγ1.

To analyze the biologic function of PAX8-PPARγ1, its ability to transactivate PPARγ response elements (PPREs) in U2OS cell was studied. PAX8-PPARγ1 (hatched bars) was ineffective compared to PPARγ1 (solid bars) in promoting troglitazone-induced transcriptional activation of luciferase reporters at a multimerized, perfect DR1 site (DR1, columns 3 and 4 of each set), at a multimerized PPRE derived from the acyl CoA oxidase gene (Aox, columns 5 and 6 of each set), and at a native PPRE from the aP2 enhancer (aP2-columns 7 and 8 of each set) (FIG. 6A). A luciferase reporter lacking a PPRE (columns 1 and 2 of each set) served as a control (RLU, relative light units). Co-expression of PAX8-PPARγ1 and PPARγ1 (in a 1:1 ratio, in column 4 of each set) led to complete inhibition of rosiglitazone-induced transactivation by PPARγ1 on the aP2 enhancer (FIG. 6B), hence PAX8-PPARγ1 may function at least in part as a dominant negative suppressor of wild-type PPARγ activities. Column 1 of each set represents expression of 1× PPARγ, column 2 of each set represents expression of 2 PPARγ and column 3 represents expression of PAX8-PPARγ1 (1×).

Transactivation assays were performed in U2OS cells as in (P. Sarraf et al. *Mol. Cell* 3, 799 (1999)) using Fugene VI (Roche). Full length PAX-PPARγ1 cDNAs with Kozak sequences were TA cloned or ligated into the pCR3.1CMV expression vector (In Vitrogen). Most experiments were performed with a PAX-PPARγ1 form containing exons 1–7 plus 9 of PAX8 and exons 1–6 of PPARγ1. The luciferase reporters are as in (R. Brun et al. *Genes Develop*. 10, 974 (1996)). Duplicate or triplicate samples were used for each condition and the standard deviation of the mean for all conditions was less than 20%.

EQUIVALENTS

It will be understood that various modifications may be made to the embodiments disclosed herein. Therefore, the above description should not be construed as limiting, but merely as exemplifications of preferred embodiments. Those skilled in the art will envision other modifications within the scope of the claims appended hereto.

All references, patents and patent applications disclosed herein are incorporated by reference in their entirety.

We claim:

1. A method of identifying the presence of a PAX8-PPARγ1 or a PPARγ1-PAX8 molecule in a sample, the method comprising: detecting with a nucleic acid probe for a PAX8-PPARγ1 or a PPARγ1-PAX8 nucleic acid molecule the presence of a PAX8-PPARγ1 or a PPARγ1-PAX8 molecule in the sample.

2. The method of claim 1, wherein the detecting comprises:

contacting the sample with at least two nucleic acid amplification primers, wherein a first nucleic acid amplification primer is capable of hybridizing to a PAX8 nucleic acid molecule and a second nucleic acid amplification primer is capable of hybridizing to a PPARγ1 nucleic acid molecule, amplifying a primed nucleic acid molecule which hybridizes to the first and the second nucleic acid amplification primers, and detecting the presence of an amplified nucleic acid molecule in the sample.

3. The method of claim 1, wherein the detecting comprises:

contacting the sample with at least two nucleic acid probes, wherein a first nucleic acid probe is capable of hybridizing to a PAX8 nucleic acid molecule and a second nucleic acid probe is capable of hybridizing to a PPARγ1 nucleic acid molecule, and detecting the presence of a nucleic acid molecule in the sample which hybridizes to both the first and the second nucleic acid probes.

4. The method of claim 1, wherein the detecting comprises:

contacting the sample with a nucleic acid probe which is capable of hybridizing to a PAX8-PPARγ1 nucleic acid fusion juncture, and detecting the presence of a nucleic acid molecule in the sample which hybridizes to the nucleic acid probe.

5. The method of claim 4, wherein the PAX8-PPARγ1 nucleic acid fusion juncture comprises a sequence selected from the group consisting of SEQ ID NO:7, SEQ ID NO:9 and SEQ ID NO:11.

6. The method of claim 1, wherein the detecting comprises amplifying the PAX8-PPARγ1 or PPARγ1-PAX8 nucleic acid.

7. The method of claim 1, wherein the sample is a thyroid tissue sample.

8. The method of claim 7, wherein the thyroid tissue sample is from a patient suspected of having a thyroid cancer.

* * * * *